United States Patent [19]
Brown et al.

[11] Patent Number: 5,689,052
[45] Date of Patent: Nov. 18, 1997

[54] SYNTHETIC DNA SEQUENCES HAVING ENHANCED EXPRESSION IN MONOCOTYLEDONOUS PLANTS AND METHOD FOR PREPARATION THEREOF

[75] Inventors: Sherri Marie Brown, Chesterfield; Duff Allen Dean, St. Louis; Michael Ernest Fromm, Chesterfield; Patricia Rigden Sanders, Chesterfield, all of Mo.

[73] Assignee: Monsanto Company, St. Louis, Mo.

[21] Appl. No.: 530,492

[22] Filed: Sep. 19, 1995

Related U.S. Application Data

[63] Continuation of Ser. No. 172,333, Dec. 22, 1993, abandoned.
[51] Int. Cl.$^6$ .............................. A01H 5/00; C12N 15/11; C12N 15/82
[52] U.S. Cl. ................. 800/205; 800/250; 800/DIG. 56; 536/23.71; 935/10; 935/30
[58] Field of Search ........................... 435/172.3, 172.1, 435/69.8, 69.7; 536/23.1, 23.71; 530/350; 935/10, 30, 35; 800/205, 250

[56] References Cited

U.S. PATENT DOCUMENTS 5,082,767  1/1992  Hafsield et al. ........................... 435/6

FOREIGN PATENT DOCUMENTS

| 0359472 | 3/1990 | European Pat. Off. ......... C12N 15/32 |
| WO 93/07278 | 4/1993 | European Pat. Off. .................. 536/27 |
| 90/100076 | 9/1990 | WIPO ............................ C12N 15/82 |

OTHER PUBLICATIONS

Murray et al. (1989) *Codon Usage in plant genes*. Nucleic Acids Research vol. 17, No. 2, pp. 477–498.

Spencer et al. (1992) *Segregation of transgenes in maize*. Plant Molecular Biology vol. 18, pp. 201–210.

Potrykus, I. (1990) *Gene Transfer ti Cereals: An Assessment*. Bio/Technology, pp. 535–542.

*Primary Examiner*—Gary Benzion
*Attorney, Agent, or Firm*—Arnold, White, & Durkee

[57] ABSTRACT

A method for modifying a foreign nucleotide sequence for enhanced accumulation of its protein product in a monocotyledonous plant and/or increasing the frequency of obtaining transgenic monocotyledonous plants which accumulate useful amounts of a transgenic protein by reducing the frequency of the rare and semi-rare monocotyledonous codons in the foreign gene and replacing them with more preferred monocotyledonous codons is disclosed. In addition, a method for enhancing the accumulation of a polypeptide encoded by a nucleotide sequence in a monocotyledonous plant and/or increasing the frequency of obtaining transgenic monocotyledonous plants which accumulate useful amounts of a transgenic protein by analyzing the coding sequence in successive six nucleotide fragments and altering the sequence based on the frequency of appearance of the six-mers as to the frequency of appearance of the rarest 284, 484, and 664 six-mers in monocotyledonous plants is provided. Also disclosed are novel structural genes which encode insecticidal proteins of B. t. k. and monocotyledonous (e.g. maize) plants containing such novel structural genes.

10 Claims, 31 Drawing Sheets

| | | | | | | |
|---|---|---|---|---|---|---|
| GLY | GGG | 14 % | | ILE | ATA | 7 % |
| | GGA | 12 % | | | ATT | 27 % |
| | GGT | 24 % | | | ATC | 67 % |
| | GGC | 50 % | | | | |
| | | | | THR | ACG | 23 % |
| GLU | GAG | 85 % | | | ACA | 12 % |
| | GAA | 15 % | | | ACT | 19 % |
| | | | | | ACC | 46 % |
| ASP | GAT | 30 % | | | | |
| | GAC | 70 % | | TRP | TGG | 100 % |
| VAL | GTG | 36 % | | CYS | TGT | 20 % |
| | GTA | 5 % | | | TGC | 80 % |
| | GTT | 20 % | | | | |
| | GTC | 39 % | | TYR | TAT | 15 % |
| | | | | | TAC | 85 % |
| ALA | GCG | 23 % | | | | |
| | GCA | 10 % | | LEU | TTG | 11 % |
| | GCT | 27 % | | | TTA | 1 % |
| | GCC | 40 % | | | CTG | 37 % |
| | | | | | CTA | 3 % |
| ARG | AGG | 26 % | | | CTT | 17 % |
| | AGA | 8 % | | | CTC | 32 % |
| | CGG | 9 % | | | | |
| | CGA | 3 % | | PHE | TTT | 22 % |
| | CGT | 13 % | | | TTC | 78 % |
| | CGC | 41 % | | | | |
| | | | | GLN | CAG | 80 % |
| SER | AGT | 6 % | | | CAA | 20 % |
| | AGC | 27 % | | | | |
| | TCG | 17 % | | HIS | CAT | 27 % |
| | TCA | 6 % | | | CAC | 73 % |
| | TCT | 14 % | | | | |
| | TCC | 29 % | | PRO | CCG | 27 % |
| | | | | | CCA | 22 % |
| LYS | AAG | 89 % | | | CCT | 19 % |
| | AAA | 11 % | | | CCC | 31 % |
| ASN | AAT | 21 % | | END | TAG | 38 % |
| | AAC | 79 % | | | TAA | 19 % |
| | | | | | TGA | 43 % |
| MET | ATG | 100 % | | | | |

FIG. 1

TATAGA TTAAAC GTAATA AGTAAC ATTAAA TAATAC CGTAGA TAGATC GAGTAA ATAGA
TAGATA TATAGT TAGAAC GTAATC TTTAGA TTAATA TTAGTA ATAATA CACTTA CGTAT
TAGGTA GACTTA TAATAG TAGTTA GCGTAG TTTAAA TTATAG ATAAAA TAGTCT AATTA
CTTAGT TCGTAT GTTAGT TTAGAT TTAGGT TTAAAT TAGGGT GTATAC ATTAGA TCTAG
CACGTA CCGATA TACGTA CGAATA TAATTA TATACG GTTATA TAGGCG TATGTA TTAAC
CGGATA TAATCG AATTTA GTATAG TATAAA ATTACG ATAGAA ACTTAG ACGTAA CGAAT
GTATCG TAAATT TTAGGG TAATCT CTAATT TAATAT CTAGTT TAGAAT TAACGT GTAAC
TAAGAC CGTAAC TTAGAC TAGTAC TAAAGC TTAGTC TAGTTC TGTAGA AATAGA GTAGT
TAGTAG CGATTA ATACCG TAAGTA CGGTAG GCGTTA GTAACG AGCGTA TATTAG GTCTT
ATAACG ATCGTA AGTCTT ACTTTA TCTTAG TCTTTA TAGACT TAAATA TAAACG TAAAC
TAGATT GTAGAA GTCTAG CTTAAA CGTACT TAGTAA AGTTAG TTAAAA ATACGT CAGTA
CTTAGG TAAAAA AGTAAT CTATAA TAATTT CGCTAA GTAGAT TAGTGT CATAAT ATAGT
CGTTAT TTAGTT TAAAAT CGTAAT TAACAC ATTAAC CTTAAC TGTAAC GTAGAC AATAA
CTAGAC TAAAAC AAACGC TTACGC ATAGGC ATAGTC CTAATC AAAACG TAGGTC GTTAC
CTTAGA GAGTAG GTAGGA TATGCG ACGGTA TCGTAG ACTGTA CCGTAG GAATTA CCTTA
AAATTA CGTTAG GCCTTA GAATAG TTTTTA CAATAG TAACTA TTACGT TTACTA TAAAA
TAGACA GCTAGT TAAGCA GTAGTG TTAGAA GTAATT AGTTAA TAACGG CTTTAA TAACC
GAATAA TTTAGG GCGTAA ATTAGT ATATAA AATCGG TAATAA TAGCCT AATAAA TAGGG
TAGTTT AATACT AATAGT TATACT TTAATT CCTAAT ACTTTT CTAAAT TACGTT CTAGA
TTAACC TAGACC AATTAC AATAGC AGAGTC ATAATC CTAGTC CTTATC TAACGA TACCG
TAGCGA CCTAGA AGAGTA TTTACG ATAGTA CTAGCG CTCGTA GTAGCG CTAGTA TTAGA
TTATTA ATTTAG GTCGTA CTTTAG AACTTA GGTTAG GAGTTA GACTAG GGCTTA GCCTA
CCGTTA TACTAG CGGTTA TAGCGT AGTTTA CGATAG AGTCTA AGTAGT GGTATA ATATA
ACGATA GGTAGT TGTATA TTACAG ACTATA ACACTT CTAATA TATAAG GCTATA CGTAG
GTAACA AGTAAG GGTTAA ATACTT GTTTAA ACTAAG AATTAA ATAACT CCGTAA CGTAA
CCTTAA TGTAGT TCGTAA TAGTTG GACTAA ACGAAT AGGTAA TTAGTG TCATAA ACGTT
GTATAA TAGATG ACGAAA CCGAAT CGTAAA TAGGTG TCTAAA TTAAGT CTAAAA TTTAT
GTAAAA ATTAAT CGTAGG ACGATT TTACGG GTTAAT AATAGG ATAGGT TATAGG TAGTA
GTAGTT GGTAAT CTTTAT GTCTAT

FIG. 2A

```
TATAGA TTAAAC GTAATA AGTAAC ATTAAA TAATAC CGTAGA TAGATC GAGTAA ATAGA
TAGATA TATAGT TAGAAC GTAATC TTTAGA TTAATA TTAGTA ATAATA CACTTA CGTAT
TAGGTA GACTTA TAATAG TAGTTA GCGTAG TTTAAA TTATAG ATAAAA TAGTCT AATTA
CTTAGT TCGTAT GTTAGT TTAGAT TTAGGT TTAAAT TAGGGT GTATAC ATTAGA TCTAG
CACGTA CCGATA TACGTA CGAATA TAATTA TATACG GTTATA TAGGCG TATGTA TTAAC
CGGATA TAATCG AATTTA GTATAG TATAAA ATTACG ATAGAA ACTTAG ACGTAA CGAAT
GTATCG TAAATT TTAGGG TAATCT CTAATT TAATAT CTAGTT TAGAAT TAACGT GTAAC
TAAGAC CGTAAC TTAGAC TAGTAC TAAAGC TTAGTC TAGTTC TGTAGA AATAGA GTAGT
TAGTAG CGATTA ATACCG TAAGTA CGGTAG GCGTTA GTAACG AGCGTA TATTAG GTCTT
ATAACG ATCGTA AGTCTT ACTTTA TCTTAG TCTTTA TAGACT TAAATA TAAACG TAAAC
TAGATT GTAGAA GTCTAG CTTAAA TAGTAA AGTTAG TTAAAA ATACGT CAGTAA CTTAG
TAAAAA AGTAAT CTATAA TAATTT CGCTAA GTAGAT TAGTGT CATAAT ATAGTT CGTTA
TTAGTT TAAAAT CGTAAT TAACAC ATTAAC CTTAAC TGTAAC GTAGAC AATAAC CTAGA
TAAAAC AAACGC TTACGC ATAGGC ATAGTC CTAATC AAAACG TAGGTC GTTACG CTTAG
GAGTAG GTAGGA TATGCG ACGGTA TCGTAG ACTGTA CCGTAG GAATTA CCTTAG AAATT
CGTTAG GCCTTA GAATAG TTTTTA CAATAG TAACTA TTACGT TTACTA TAAAAG TAGAC
GCTAGT TAAGCA GTAGTG TTAGAA GTAATT AGTTAA TAACGG CTTTAA TAACCT GAATA
TTTAGG GCGTAA ATTAGT ATATAA AATCGG TAATAA TAGCCT AATAAA TAGGGG TAGTT
AATACT AATAGT TATACT TTAATT CCTAAT ACTTTT CTAAAT TACGTT CTAGAT TTAAC
TAGACC AATTAC AATAGC AGAGTC ATAATC CTAGTC CTTATC TAACGA TACCGA TAGCG
CCTAGA AGAGTA TTTACG ATAGTA CTAGCG CTCGTA GTAGCG CTAGTA TTAGAG TTATT
ATTTAG GTCGTA CTTTAG AACTTA GGTTAG GAGTTA GACTAG GGCTTA GCCTAG CCGTT
TACTAG CGGTTA TAGCGT AGTTTA CGATAG AGTCTA AGTAGT GGTATA ATATAG ACGAT
GGTAGT TGTATA TTACAG ACTATA ACACTT CTAATA TATAAG GCTATA CGTAGT GTAAC
AGTAAG GGTTAA ATACTT GTTTAA ACTAAG AATTAA ATAACT CCGTAA CGTAAG CCTTA
TGTAGT TCGTAA TAGTTG GACTAA ACGAAT AGGTAA TTAGTG TCATAA ACGTTT GTATA
TAGATG ACGAAA CCGAAT CGTAAA TAGGTG TCTAAA TTAAGT CTAAAA TTTATG GTAAA
ATTAAT CGTAGG ACGATT TTACGG GTTAAT AATAGG ATAGGT TATAGG TAGTAT GTAGT
```

FIG. 2B

```
GGTAAT CTTTAT GTCTAT TAACCC GTAGCC TAGTCC AGTCAC TAACCG ACTTAC CATAC
TTATAC CACTCG TAGAGC TAGTCG GTTTAC GTAGAG TTAAGC TAGAGT CGTAGC ATAGA
GTATGC ACGCTT TAGGGC TAAGAG TAATTC TTTAGT AGTGTC TAGGAG TTACGA TTAAC
ATTCGA AAGTAG TAGAGA TATATT GATAGA ATGTAG GGTAGA TAAGCT ACTAGA AGGTA
GTAAGA TCTAGT TTATGA TTGTAG CGCGTA TTATCT TTCGTA GATTAG ACGTTA TTTAT
ACATTA GTTTAG TATTTA ACTCAT CTCTTA ATCTAG CCTTTA GATAGT CGTTTA CCATA
GGTCTA TTTAAT TTTATA TTAAAG AATATA TCGATT TATATA ATAGTG TATACA TGTAA
TAATCA AAACGG TAGTCA TACAGT TATTAA ATACGG ACTTAA CACGAT GTGTAA GTTAG
TCTTAA TATGTT TACTAA TCTAGG CTCTAA GATAAT AACTAA GTAGGG GTCTAA CTAAG
CGATAA CTAGGG AGTAAA TCCGAT GGTAAA TACTGT TCTAAT TACGGT GTGTAT GTAGG
TATAAT TAAGGT ATTTAT GTAAAT TTTTAT AATTAT CGATAT TTATAT ATAGCC TAATC
ATACGC GTTAAC ATTAGC CATAAC AGTAGC TTTTAC TTACCG GTAAGC TAGACG ATAAA
ACGTAG GTATTC GGGTAG CTATAC GTGTAG CTAGGC GCTTAG GTAGTC CGCTAG TTAGG
CTCTAG TAAGTC GCATAG TTAATC TAGAAG TGTATC GTTAAG TTGCGA TAACTG CATAG
TAAATG GTTAGA TAGCGG ATAAGA CTTACT TTAGGA AGTAGG TCCGTA TTTACT AGTGT
GGTAGG TGTGTA CGTATT GATTTA ATTAGG ATTTTA CTCGAT GGTTTA CATAGG CAATT
GCGATT TAGCTA TAAGGG TCGCTA TAGGAT AATCTA GGGGGG GCGATA CGTTTT ATTAT
CGGTAT CCTATA TCGTTT GTCATA GCGTAT GGAATA TAAGTT TGAATA ATGTAT TAGGC
TTTCGT TACGAA ACTTAT CATTAA CTTTTT CGTTAA CTGTAT TTTTAA ATGCGT CCCTA
TCTTAT GCATAA CGATTT TTCTAA CACTAT TAGAAA GTAAGT ACTAAA TTGAAT CATAA
AAAAGT ACCTAT CTATAT CCCTAT
```

FIG. 2C

```
TATAGA TTAAAC GTAATA AGTAAC ATTAAA TAATAC CGTAGA TAGATC GAGTAA ATAGA
TAGATA TATAGT TAGAAC GTAATC TTTAGA TTAATA TTAGTA ATAATA CACTTA CGTAT
TAGGTA GACTTA TAATAG TAGTTA GCGTAG TTTAAA TTATAG ATAAAA TAGTCT AATTA
CTTAGT TCGTAT GTTAGT TTAGAT TTAGGT TTAAAT TAGGGT GTATAC ATTAGA TCTAG
CACGTA CCGATA TACGTA CGAATA TAATTA TATACG GTTATA TAGGCG TATGTA TTAAC
CGGATA TAATCG AATTTA GTATAG TATAAA ATTACG ATAGAA ACTTAG ACGTAA CGAAT
GTATCG TAAATT TTAGGG TAATCT CTAATT TAATAT CTAGTT TAGAAT TAACGT GTAAC
TAAGAC CGTAAC TTAGAC TAGTAC TAAAGC TTAGTC TAGTTC TGTAGA AATAGA GTAGT
TAGTAG CGATTA ATACCG TAAGTA CGGTAG GCGTTA GTAACG AGCGTA TATTAG GTCTT
ATAACG ATCGTA AGTCTT ACTTTA TCTTAG TCTTTA TAGACT TAAATA TAAACG TAAAC
TAGATT GTAGAA GTCTAG CTTAAA CGTACT TAGTAA AGTTAG TTAAAA ATACGT CAGTA
CTTAGG TAAAAA AGTAAT CTATAA TAATTT CGCTAA GTAGAT TAGTGT CATAAT ATAGT
CGTTAT TTAGTT TAAAAT CGTAAT TAACAC ATTAAC CTTAAC TGTAAC GTAGAC AATAA
CTAGAC TAAAAC AAACGC TTACGC ATAGGC ATAGTC CTAATC AAACG TAGGTC GTTAC
CTTAGA GAGTAG GTAGGA TATGCG ACGGTA TCGTAG ACTGTA CCGTAG GAATTA CCTTA
AAATTA CGTTAG GCCTTA GAATAG TTTTTA CAATAG TAACTA TTACGT TTACTA TAAAA
TAGACA GCTAGT TAAGCA GTAGTG TTAGAA GTAATT AGTTAA TAACGG CTTTAA TAACC
GAATAA TTTAGG GCGTAA ATTAGT ATATAA AATCGG TAATAA TAGCCT AATAAA TAGGG
TAGTTT AATACT AATAGT TATACT TTAATT CCTAAT ACTTTT CTAAAT TACGTT CTAGA
TTAACC TAGACC AATTAC AATAGC AGAGTC ATAATC CTAGTC CTTATC TAACGA TACCG
TAGCGA CCTAGA AGAGTA TTTACG ATAGTA CTAGCG CTCGTA GTAGCG CTAGTA TTAGA
TTATTA ATTTAG GTCGTA CTTTAG AACTTA GGTTAG GAGTTA GACTAG GGCTTA GCCTA
CCGTTA TACTAG CGGTTA TAGCGT AGTTTA CGATAG AGTCTA AGTAGT GGTATA ATATA
ACGATA GGTAGT TGTATA TTACAG ACTATA ACACTT CTAATA TATAAG GCTATA CGTAG
GTAACA AGTAAG GGTTAA ATACTT GTTTAA ACTAAG AATTAA ATAACT CCGTAA CGTAA
CCTTAA TGTAGT TCGTAA TAGTTG GACTAA ACGAAT AGGTAA TTAGTG TCATAA ACGTT
GTATAA TAGATG ACGAAA CCGAAT CGTAAA TAGGTG TCTAAA TTAAGT CTAAAA TTTAT
GTAAAA ATTAAT CGTAGG ACGATT TTACGG GTTAAT AATAGG ATAGGT TATAGG TAGTA
GTAGTT GGTAAT CTTTAT GTCTAT TAACCC GTAGCC TAGTCC AGTCAC TAACCG ACTTA
CATACG TTATAC CACTCG TAGAGC TAGTCG GTTTAC GTAGAG TTAAGC TAGAGT CGTAG
ATAGAG GTATGC ACGCTT TAGGGC TAAGAG TAATTC TTTAGT AGTGTC TAGGAG TTACG
TTAACT ATTCGA AAGTAG TAGAGA TATATT GATAGA ATGTAG GGTAGA TAAGCT ACTAG
AGGTAG GTAAGA TCTAGT TTATGA TTGTAG CGCGTA TTATCT TTCGTA GATTAG ACGTT
TTTATT ACATTA GTTTAG TATTTA ACTCAT CTCTTA ATCTAG CCTTTA GATAGT CGTTT
CCATAG GGTCTA TTTAAT TTTATA TTAAAG AATATA TCGATT TATATA ATAGTG TATAC
TGTAAT TAATCA AAACGG TAGTCA TACAGT TATTAA ATACGG ACTTAA CACGAT GTGTA
GTTAGG TCTTAA TATGTT TACTAA TCTAGG CTCTAA GATAAT AACTAA GTAGGG GTCTA
```

FIG. 2D

```
CTAAGT CGATAA CTAGGG AGTAAA TCCGAT GGTAAA TACTGT TCTAAT TACGGT GTGTA'
GTAGGT TATAAT TAAGGT ATTTAT GTAAAT TTTTAT AATTAT CGATAT TTATAT ATAGC
TAATCC ATACGC GTTAAC ATTAGC CATAAC AGTAGC TTTTAC TTACCG GTAAGC TAGAC
ATAAAC ACGTAG GTATTC GGGTAG CTATAC GTGTAG CTAGGC GCTTAG GTAGTC CGCTA
TTAGGC CTCTAG TAAGTC GCATAG TTAATC TAGAAG TGTATC GTTAAG TTGCGA TAACT
CATAGA TAAATG GTTAGA TAGCGG ATAAGA CTTACT TTAGGA AGTAGG TCCGTA TTTAC
AGTGTA GGTAGG TGTGTA CGTATT GATTTA ATTAGG ATTTTA CTCGAT GGTTTA CATAG
CAATTA GCGATT TAGCTA TAAGGG TCGCTA TAGGAT AATCTA GGGGGG GCGATA CGTTT
ATTATA CGGTAT CCTATA TCGTTT GTCATA GCGTAT GGAATA TAAGTT TGAATA ATGTA
TAGGCA TTTCGT TACGAA ACTTAT CATTAA CTTTTT CGTTAA CTGTAT TTTTAA ATGCG
CCCTAA TCTTAT GCATAA CGATTT TTCTAA CACTAT TAGAAA GTAAGT ACTAAA TTGAA
CATAAA AAAAGT ACCTAT CTATAT CCCTAT TTAGCC ATAACC CTATCC TAACGC TTACA
TATCGC ACGAAC CTTAGC ACTAAC ACTTTC GATAAC ACTAGC CTAAAC TTTTTC ATAGA
TAGCCG ACGGTC AATCCG GTAAAC AATACG AGACTC CTTACG CGTTAC GATACG TAAAT
GAAACG GAATAC CTATCG CGTATC GATTCG CCTATC TTTTAG ATACGA AAATAG TAGTG
GGATAG ATAGGA CTATAG TCAGTA AAACAG AAGTTA TAGCAG TCGTTA TTTAAG GCATT
GATAAG GTGTTA CTTAAG CGCTTA TCTAAG CTTTTA CGAAAG TCATTA TAATTG TGATT
TAAACT GTATTA CGATTG TATCTA TAGGCT AAACTA TATCGG AGTATA TACTCT GATAT
ATTCGG CTTATA GAATCT TCTATA GTAAGG TTCATA TGTATT GCAATA ACCGAT TACGC
AAAATT TTAGCA ACGTAT CTAGAA ACACGT AAGTAA AGTTAT ATTTAA TACTTT ACATA
TACTAT CCATAA TCACGT GTTAAA GCCTAT CGAAAA CGCTTT CGCTAT TTGAGT TAGCA
CATAGT ATGAAT TTATGT CTAGGT TAGCCC CTAGCC TAAACC TTATCC TTTACC TAGCA
ATACAC TATCAC ACTCAC TTTAAC TATAAC AGTGAC CGAAAC AATCGC TCGTAC TGTAG
CATTAC ATAAGC AGATAC GTAGGC GATTAC TATTTC CGATAC TGAGTC AATCTC TGAAT
AAACGA AGTAGA TACGGA TGCGTA ACCGTA GCGGTA TTTGTA TGGTTA CTGTTA TGTTT
GTTTTA AGCTTA ATATTA ACGCTA ATTCTA TAAGCG ATACTA CATTCG AATTCA CTGTA
TAGCCA CATTAG TCCGAA TTCTAG AACGAA TCATAG CTCGAA GTAATG ATGTAA TAGAG
GATTAA TAATGG GCTTAA TAGTGG ACCTAA ATAGGG GGATAA AGACTT CCGAAA CTAAC
TATCTT TTAGCT GTGATT GCGAAT CGCATT GTGAAT ACTAGT ACTAAT ATAATT ATAAA
ATAAGT CACTTT ATATGT ATCGGT
```

FIG. 2E

```
   1  CCATGGACAA CAACCCAAAC ATCAACGAGT GCATCCCGTA CAACTGCCTC
  51  AGCAACCCTG AGGTCGAGGT GCTCGGCGGT GAGCGCATCG AGACCGGTTA
 101  CACCCCCATC GACATCTCCC TCTCCCTCAC GCAGTTCCTG CTCAGCGAGT
 151  TCGTGCCAGG CGCTGGCTTC GTCCTGGGCC TCGTGGACAT CATCTGGGGC
 201  ATCTTTGGCC CCTCCCAGTG GGACGCCTTC CTGGTGCAAA TCGAGCAGCT
 251  CATCAACCAG AGGATCGAGG AGTTCGCCAG GAACCAGGCC ATCAGCCGCC
 301  TGGAGGGCCT CAGCAACCTC TACCAAATCT ACGCTGAGAG CTTCCGCGAG
 351  TGGGAGGCCG ACCCCACTAA CCCAGCTCTC CGCGAGGAGA TGCGCATCCA
 401  GTTCAACGAC ATGAACAGCG CCCTGACCAC CGCCATCCCA CTCTTCGCCG
 451  TCCAGAACTA CCAAGTCCCG CTCCTGTCCG TGTACGTCCA GGCCGCCAAC
 501  CTGCACCTCA GCGTGCTGAG GGACGTCAGC GTGTTTGGCC AGAGGTGGGG
 551  CTTCGACGCC GCCACCATCA ACAGCCGCTA CAACGACCTC ACCAGGCTGA
 601  TCGGCAACTA CACCGACCAC GCTGTCCGCT GGTACAACAC TGGCCTGGAG
 651  CGCGTCTGGG GCCCTGATTC TAGAGACTGG ATTCGCTACA ACCAGTTCAG
 701  GCGCGAGCTG ACCCTCACCG TCCTGGACAT TGTGTCCCTC TTCCCGAACT
 751  ACGACTCCCG CACCTACCCG ATCCGCACCG TGTCCCAACT GACCCGCGAA
 801  ATCTACACCA ACCCCGTCCT GGAGAACTTC GACGGTAGCT TCAGGGGCAG
 851  CGCCCAGGGC ATCGAGGGCT CCATCAGGAG CCCACACCTG ATGGACATCC
 901  TCAACAGCAT CACTATCTAC ACCGATGCCC ACCGCGGCGA GTACTACTGG
 951  TCCGGCCACC AGATCATGGC CTCCCCGGTC GGCTTCAGCG GCCCCGAGTT
1001  TACCTTTCCT CTCTACGGCA CGATGGGCAA CGCCGCTCCA CAACAACGCA
1051  TCGTCGCTCA GCTGGGCCAG GGCGTCTACC GCACCCTGAG CTCCACCCTG
1101  TACCGCAGGC CCTTCAACAT CGGTATCAAC AACCAGCAGC TGTCCGTCCT
1151  GGATGGCACT GAGTTCGCCT ACGGCACCTC CTCCAACCTG CCCTCCGCTG
```

FIG. 3A

```
603  GGCAACTACACCGACCACGCTGTCCGCTGGTACAACACTGGCCTGGAGCG 652
     |||||||| || || ||  |||||  ||||||||||| || ||  | |||||
601  GGCAACTATACAGATCATGCTGTACGCTGGTACAATACGGGATTAGAGCG 650

653  CGTCTGGGGCCCTGATTCTAGAGACTGGATTCGCTACAACCAGTTCAGGC 702
     || ||||||  || ||||||||||||| |||||  | || || || || ||
651  TGTATGGGGACCGGATTCTAGAGATTGGATAAGATATAATCAATTTAGAA 700

703  GCGAGCTGACCCTCACCGTCCTGGACATTGTGTCCCTCTTCCCGAACTAC 752
     | ||  | ||| || || ||  | || || || || || || ||||||||
701  GAGAATTAACACTAACTGTATTAGATATCGTTTCTCTATTTCCGAACTAT 750

753  GACTCCCGCACCTACCCGATCCGCACCGTGTCCCAACTGACCCGCGAAAT 802
     ||    | ||| || || || || || || || |||||| | ||  | |||||
751  GATAGTAGAACGTATCCAATTCGAACAGTTTCCCAATTAACAAGAGAAAT 800

803  CTACACCAACCCCGTCCTGGAGAACTTCGACGGTAGCTTCAGGGGCAGCG 852
     || || |||||  ||  | || || || || || ||||| || | ||| |
801  TTATACAAACCCAGTATTAGAAAATTTTGATGGTAGTTTTCGAGGCTCGG 850

853  CCCAGGGCATCGAGGGCTCCATCAGGAGCCCACACCTGATGGACATCCTC 902
     | ||||||||  || || ||    || ||||| |||||  |||||| || ||
851  CTCAGGGCATAGAAGGAAGTATTAGGAGTCCACATTTGATGGATATACTT 900

903  AACAGCATCACTATCTACACCGATGCCCACCGCGGCGAGTACTACTGGTC 952
     || || || || || ||||| || ||||| || | || || || || |||||
901  AATAGTATAACCATCTATACGGATGCTCATAGAGGAGAATATTATTGGTC 950

953  CGGCCACCAGATCATGGCCTCCCCGGTCGGCTTCAGCGGCCCCGAGTTTA 1002
     || || || || ||||| || || || || ||   || || || || | 
951  AGGGCATCAAATAATGGCTTCTCCTGTAGGGTTTTCGGGGCCAGAATTCA 1000

1003 CCTTTCCTCTCTACGGCACGATGGGCAACGCCGCTCCACAACAACGCATC 1052
     | |||||| || || || || |||||  || || |||||||||||||| ||
1001 CTTTTCCGCTATATGGAACTATGGGAAATGCAGCTCCACAACAACGTATT 1050

1053 GTCGCTCAGCTGGGCCAGGGCGTCTACCGCACCCTGAGCTCCACCCTGTA 1102
     || ||||| || || || ||||||||| ||  | ||  | |||||| | ||
1051 GTTGCTCAACTAGGTCAGGGCGTGTATAGAACATTATCGTCCACCTTATA 1100

1103 CCGCAGGCCCTTCAACATCGGTATCAACAACCAGCAGCTGTCCGTCCTGG 1152
     | || || || || || || || || || |||| || ||||  || ||
1101 TAGAAGACCTTTTAATATAGGGATAAATAATCAACAACTATCTGTTCTTG 1150

1153 ATGGCACTGAGTTCGCCTACGGCACCTCCTCCAACCTGCCCTCCGCTGTC 1202
     | || || || || || || || || || |||||||| ||  |||| |||||||
1151 ACGGGACAGAATTTGCTTATGGAACCTCCTCAAATTTGCCATCCGCTGTA 1200
```

FIG. 3B

```
1203 TACCGCAAGAGCGGCACGGTGGATTCCCTGGACGAGATCCCACCACAGAA 1252
     ||| | || ||||| ||||| ||||| ||||| || || || ||||||||
1201 TACAGAAAAAGCGGAACGGTAGATTCGCTGGATGAAATACCGCCACAGAA 1250

1253 CAACAATGTGCCCCCCAGGCAGGGTTTTTCCCACAGGCTCAGCCACGTGT 1302
     ||||| ||||| || ||||| || |||    || |  | ||||| || |
1251 TAACAACGTGCCACCTAGGCAAGGATTTAGTCATCGATTAAGCCATGTTT 1300

1303 CCATGTTCCGCTCCGGCTTCAGCAACTCGTCCGTGAGCATCATCAGAGCT 1352
     | ||||| || || ||||| || ||           || || || || ||||||
1301 CAATGTTTCGTTCAGGCTTTAGTAATAGTAGTGTAAGTATAATAAGAGCT 1350

1353 CCTATGTTCTCCTGGATTCATCGCAGCGCGGAGTTCAACAATATCATTCC 1402
     |||||||||| ||||| ||||| || || || || || |||||  |||||
1351 CCTATGTTCTCTTGGATACATCGTAGTGCTGAATTTAATAATATAATTCC 1400

1403 GTCCTCCCAAATCACCCAAATCCCCCTCACCAAGTCCACCAACCTGGGCA 1452
     || || |||||  || ||||| ||  |  || || || || || ||  |||
1401 TTCATCACAAATTACACAAATACCTTTAACAAAATCTACTAATCTTGGCT 1450

1453 GCGGCACCTCCGTGGTGAAGGGCCCAGGCTTCACGGGCGGCGACATCCTG 1502
     || || || || || || || ||||| || || || || || || || ||
1451 CTGGAACTTCTGTCGTTAAAGGACCAGGATTTACAGGAGGAGATATTCTT 1500

1503 CGCAGGACCTCCCCGGGCCAGATCAGCACCCTCCGCGTCAACATCACCGC 1552
     || || || || || |||||||| ||| | | || || || || || ||
1501 CGAAGAACTTCACCTGGCCAGATTTCAACCTTAAGAGTAAATATTACTGC 1550

1553 TCCCCTGTCCCAGAGGTACCGCGTCAGGATTCGCTACGCTAGCACCACCA 1602
     || | || || || || || || || || |||||||||||   ||||| |
1551 ACCATTATCACAAAGATATCGGGTAAGAATTCGCTACGCTTCTACCACAA 1600

1603 ACCTGCAATTCCACACCTCCATCGACGGCAGGCCGATCAATCAGGGTAAC 1652
     |  | |||||||| || || || ||||| || || || ||||||||| ||
1601 ATTTACAATTCCATACATCAATTGACGGAAGACCTATTAATCAGGGGAAT 1650

1653 TTCTCCGCCACCATGTCCAGCGGCAGCAACCTCCAATCCGGCAGCTTCCG 1702
     || || || || |||   || || || || ||  | || ||||| ||||| |
1651 TTTTCAGCAACTATGAGTAGTGGGAGTAATTTACAGTCCGGAAGCTTTAG 1700

1703 CACCGTGGGTTTCACCACCCCCTTCAACTTCTCCAACGGCTCCAGCGTTT 1752
     || || ||||| || || || || ||||| || || || || || || |
1701 GACTGTAGGTTTTACTACTCCGTTTAACTTTTCAAATGGATCAAGTGTAT 1750

1753 TCACCCTGAGCGCCCACGTGTTCAATTCCGGCAATGAGGTGTACATTGAC 1802
     | || | || || || || || |||||||| |||||||| || || || ||
1751 TTACGTTAAGTGCTCATGTCTTCAATTCAGGCAATGAAGTTTATATAGAT 1800
```

FIG. 3C

```
  1 ATGGACAACA ACGTCTTGAA CTCTGGTAGA ACAACCATCT GCGACGCATA
 51 CAACGTCGTG GCTCACGATC CATTCAGCTT CGAACACAAG AGCCTCGACA
101 CTATTCAGAA GGAGTGGATG GAATGGAAAC GTACTGACCA CTCTCTCTAC
151 GTCGCACCTG TGGTTGGAAC AGTGTCCAGC TTCCTTCTCA AGAAGGTCGG
201 CTCTCTCATC GGAAAACGTA TCTTGTCCGA ACTCTGGGGT ATCATCTTTC
251 CATCTGGGTC CACTAATCTC ATGCAAGACA TCTTGAGGGA GACCGAACAG
301 TTTCTCAACC AGCGTCTCAA CACTGATACC TTGGCTAGAG TCAACGCTGA
351 GTTGATCGGT CTCCAAGCAA ACATTCGTGA GTTCAACCAG CAAGTGGACA
401 ACTTCTTGAA TCCAACTCAG AATCCTGTGC CTCTTTCCAT CACTTCTTCC
451 GTGAACACTA TGCAGCAACT CTTCCTCAAC AGATTGCCTC AGTTTCAGAT
501 TCAAGGCTAC CAGTTGCTCC TTCTTCCACT CTTTGCTCAG GCTGCCAACA
551 TGCACTTGTC CTTCATACGT GACGTGATCC TCAACGCTGA CGAATGGGGA
601 ATCTCTGCAG CCACTCTTAG GACATACAGA GACTACTTGA GGAACTACAC
651 TCGTGATTAC TCCAACTATT GCATCAACAC TTATCAGACT GCCTTTCGTG
701 GACTCAATAC TAGGCTTCAC GACATGCTTG AGTTCAGGAC CTACATGTTC
751 CTTAACGTGT TTGAGTACGT CAGCATTTGG AGTCTCTTCA AGTACCAGAG
801 CTTGATGGTG TCCTCTGGAG CCAATCTCTA CGCCTCTGGC AGTGGACCAC
851 AGCAAACTCA GAGCTTCACA GCTCAGAACT GGCCATTCTT GTATAGCTTG
901 TTCCAAGTCA ACTCCAACTA CATTCTCAGT GGTATCTCTG GGACCAGACT
```

FIG. 4A

```
 951  CTCCATAACC TTTCCCAACA TTGGTGGACT TCCAGGCTCC ACTACAACCC
1001  ATAGCCTTAA CTCTGCCAGA GTGAACTACA GTGGAGGTGT CAGCTCTGGA
1051  TTGATTGGTG CAACTAACTT GAACCACAAC TTCAATTGCT CCACCGTCTT
1101  GCCACCTCTG AGCACACCGT TGTGAGGTC CTGGCTTGAC AGCGGTACTG
1151  ATCGCGAAGG AGTTGCTACC TCTACAAACT GGCAAACCGA GTCCTTCCAA
1201  ACCACTCTTA GCCTTCGGTG TGGAGCTTTC TCTGCACGTG GGAATTCAAA
1251  CTACTTTCCA GACTACTTCA TTAGGAACAT CTCTGGTGTT CCTCTCGTCA
1301  TCAGGAATGA AGACCTCACC CGTCCACTTC ATTACAACCA GATTAGGAAC
1351  ATCGAGTCTC CATCCGGTAC TCCAGGAGGT GCAAGAGCTT ACCTCGTGTC
1401  TGTCCATAAC AGGAAGAACA ACATCTACGC TGCCAACGAG AATGGCACCA
1451  TGATTCACCT TGCACCAGAA GATTACACTG GATTCACCAT CTCTCCAATC
1501  CATGCTACCC AAGTGAACAA TCAGACACGC ACCTTCATCT CCGAAAAGTT
1551  CGGAAATCAA GGTGACTCCT TGAGGTTCGA GCAATCCAAC ACTACCGCTA
1601  GGTACACTTT GAGAGGCAAT GGAAACAGCT ACAACCTTTA CTTGAGAGTT
1651  AGCTCCATTG GTAACTCCAC CATCCGTGTT ACCATCAACG ACGTGTTTA
1701  CACAGTCTCT AATGTGAACA CTACAACGAA CAATGATGGC GTTAACGACA
1751  ACGGAGCCAG ATTCAGCGAC ATCAACATTG CAACATCGT GGCCTCTGAC
1801  AACACTAACG TTACTTTGGA CATCAATGTG ACCCTCAATT CTGGAACTCC
1851  ATTTGATCTC ATGAACATCA TGTTTGTGCC AACTAACCTC CCTCCATTGT
1901  ACTAATGAGA TCTAAGCTT
```

FIG. 4B

```
   1  AGATCTCCAT GGACAACAAC CCAAACATCA ACGAATGCAT TCCATACAAC
  51  TGCTTGAGTA ACCCAGAAGT TGAAGTACTT GGTGGAGAAC GCATTGAAAC
 101  CGGTTACACT CCCATCGACA TCTCCTTGTC CTTGACACAG TTTCTGCTCA
 151  GCGAGTTCGT GCCAGGTGCT GGGTTCGTTC TCGGACTAGT TGACATCATC
 201  TGGGGTATCT TTGGTCCATC TCAATGGGAT GCATTCCTGG TGCAAATTGA
 251  GCAGTTGATC AACCAGAGGA TCGAAGAGTT CGCCAGGAAC CAGGCCATCT
 301  CTAGGTTGGA AGGATTGAGC AATCTCTACC AAATCTATGC AGAGAGCTTC
 351  AGAGAGTGGG AAGCCGATCC TACTAACCCA GCTCTCCGCG AGGAAATGCG
 401  TATTCAATTC AACGACATGA ACAGCGCCTT GACCACAGCT ATCCCATTGT
 451  TCGCAGTCCA GAACTACCAA GTTCCTCTCT TGTCCGTGTA CGTTCAAGCA
 501  GCTAATCTTC ACCTCAGCGT GCTTCGAGAC GTTAGCGTGT TTGGGCAAAG
 551  GTGGGGATTC GATGCTGCAA CCATCAATAG CCGTTACAAC GACCTTACTA
 601  GGCTGATTGG AAACTACACC GACCACGCTG TTCGTTGGTA CAACACTGGC
 651  TTGGAGCGTG TCTGGGGTCC TGATTCTAGA GATTGGATTA GATACAACCA
 701  GTTCAGGAGA GAATTGACCC TCACAGTTTT GGACATTGTG TCTCTCTTCC
 751  CGAACTATGA CTCCAGAACC TACCCTATCC GTACAGTGTC CCAACTTACC
 801  AGAGAAATCT ATACTAACCC AGTTCTTGAG AACTTCGACG GTAGCTTCCG
 851  TGGTTCTGCC CAAGGTATCG AAGGCTCCAT CAGGAGCCCA CACTTGATGG
 901  ACATCTTGAA CAGCATAACT ATCTACACCG ATGCTCACAG AGGAGAGTAT
 951  TACTGGTCTG ACACCAGAT CATGGCCTCT CCAGTTGGAT TCAGCGGGCC
1001  CGAGTTTACC TTTCCTCTCT ATGGAACTAT GGGAAACGCC GCTCCACAAC
1051  AACGTATCGT TGCTCAACTA GGTCAGGGTG TCTACAGAAC CTTGTCTTCC
1101  ACCTTGTACA GAAGACCCTT CAATATCGGT ATCAACAACC AGCAACTTTC
1151  CGTTCTTGAC GGAACAGAGT TCGCCTATGG AACCTCTTCT AACTTGCCAT
1201  CCGCTGTTTA CAGAAAGAGC GGAACCGTTG ATTCCTTGGA CGAAATCCCA
```

FIG. 5A

```
1251  CCACAGAACA ACAATGTGCC ACCCAGGCAA GGATTCTCCC ACAGGTTGAG
1301  CCACGTGTCC ATGTTCCGTT CCGGATTCAG CAACAGTTCC GTGAGCATCA
1351  TCAGAGCTCC TATGTTCTCA TGGATTCATC GTAGTGCTGA GTTCAACAAT
1401  ATCATTCCTT CCTCTCAAAT CACCCAAATC CCATTGACCA AGTCTACTAA
1451  CCTTGGATCT GGAACTTCTG TCGTGAAAGG ACCAGGCTTC ACAGGAGGTG
1501  ATATTCTTAG AAGAACTTCT CCTGGCCAGA TTAGCACCCT CAGAGTTAAC
1551  ATCACTGCAC CACTTTCTCA AGATATCGT GTCAGGATTC GTTACGCATC
1601  TACCACTAAC TTGCAATTCC ACACCTCCAT CGACGGAAGG CCTATCAATC
1651  AGGGTAACTT CTCCGCAACC ATGTCAAGCG GCAGCAACTT GCAATCCGGC
1701  AGCTTCAGAA CCGTCGGTTT CACTACTCCT TTCAACTTCT CTAACGGATC
1751  AAGCGTTTTC ACCCTTAGCG CTCATGTGTT CAATTCTGGC AATGAAGTGT
1801  ACATTGACCG TATTGAGTTT GTGCCTGCCG AAGTTACCCT CGAGGCTGAG
1851  TACAACCTTG AGAGAGCCCA GAAGGCTGTG AACGCCCTCT TTACCTCCAC
1901  CAATCAGCTT GGCTTGAAAA CTAACGTTAC TGACTATCAC ATTGACCAAG
1951  TGTCCAACTT GGTCACCTAC CTTAGCGATG AGTTCTGCCT CGACGAGAAG
2001  CGTGAACTCT CCGAGAAAGT TAAACACGCC AAGCGTCTCA GCGACGAGAG
2051  GAATCTCTTG CAAGACTCCA ACTTCAAAGA CATCAACAGG CAGCCAGAAC
2101  GTGGTTGGGG TGGAAGCACC GGGATCACCA TCCAAGGAGG CGACGATGTG
2151  TTCAAGGAGA ACTACGTCAC CCTCTCCGGA ACTTTCGACG AGTGCTACCC
2201  TACCTACTTG TACCAGAAGA TCGATGAGTC CAAACTCAAA GCCTTCACCA
2251  GGTATCAACT TAGAGGCTAC ATCGAAGACA GCCAAGACCT TGAAATCTAC
2301  TCGATCAGGT ACAATGCCAA GCACGAGACC GTGAATGTCC CAGGTACTGG
2351  TTCCCTCTGG CCACTTTCTG CCCAATCTCC CATTGGGAAG TGTGGAGAGC
2401  CTAACAGATG CGCTCCACAC CTTGAGTGGA ATCCTGACTT GGACTGCTCC
2451  TGCAGGGATG GCGAGAAGTG TGCCCACCAT TCTCATCACT TCTCCTTGGA
```

FIG. 5B

```
2501  CATCGATGTG GGATGTACTG ACCTGAATGA GGACCTCGGA GTCTGGGTCA
2551  TCTTCAAGAT CAAGACCCAA GACGGACACG CAAGACTTGG CAACCTTGAG
2601  TTTCTCGAAG AGAAACCATT GGTCGGTGAA GCTCTCGCTC GTGTGAAGAG
2651  AGCAGAGAAG AAGTGGAGGG ACAAACGTGA GAAACTCGAA TGGGAAACTA
2701  ACATCGTTTA CAAGGAGGCC AAAGAGTCCG TGGATGCTTT GTTCGTGAAC
2751  TCCCAATATG ATCAGTTGCA AGCCGACACC AACATCGCCA TGATCCACGC
2801  CGCAGACAAA CGTGTGCACA GCATTCGTGA GGCTTACTTG CCTGAGTTGT
2851  CCGTGATCCC TGGTGTGAAC GCTGCCATCT TCGAGGAACT TGAGGGACGT
2901  ATCTTTACCG CATTCTCCTT GTACGATGCC AGAAACGTCA TCAAGAACGG
2951  TGACTTCAAC AATGGCCTCA GCTGCTGGAA TGTGAAAGGT CATGTGGACG
3001  TGGAGGAACA GAACAATCAG CGTTCCGTCC TGGTTGTGCC TGAGTGGGAA
3051  GCTGAAGTGT CCCAAGAGGT TAGAGTCTGT CCAGGTAGAG GCTACATTCT
3101  CCGTGTGACC GCTTACAAGG AGGGATACGG TGAGGGTTGC GTGACCATCC
3151  ACGAGATCGA GAACAACACC GACGAGCTTA AGTTCTCCAA CTGCGTCGAG
3201  GAAGAAATCT ATCCCAACAA CACCGTTACT TGCAACGACT ACACTGTGAA
3251  TCAGGAAGAG TACGGAGGTG CCTACACTAG CCGTAACAGA GGTTACAACG
3301  AAGCTCCTTC CGTTCCTGCT GACTATGCCT CCGTGTACGA GGAGAAATCC
3351  TACACAGATG GCAGACGTGA GAACCCTTGC GAGTTCAACA GAGGTTACAG
3401  GGACTACACA CCACTTCCAG TTGGCTATGT TACCAAGGAG CTTGAGTACT
3451  TTCCTGAGAC CGACAAAGTG TGGATCGAGA TCGGTGAAAC CGAGGGAACC
3501  TTCATCGTGG ACAGCGTGGA GCTTCTCTTG ATGGAGGAAT AATGAGATCT
3551  ATCGATCCAT GGAGGCCTGA ATT
```

FIG. 5C

```
   1 AGATCTCCAT GGACAACAAC CCAAACATCA ACGAATGCAT TCCATACAAC
  51 TGCTTGAGTA ACCCAGAAGT TGAAGTACTT GGTGGAGAAC GCATTGAAAC
 101 CGGTTACACT CCCATCGACA TCTCCTTGTC CTTGACACAG TTTCTGCTCA
 151 GCGAGTTCGT GCCAGGTGCT GGGTTCGTTC TCGGACTAGT TGACATCATC
 201 TGGGGTATCT TTGGTCCATC TCAATGGGAT GCATTCCTGG TGCAAATTGA
 251 GCAGTTGATC AACCAGAGGA TCGAAGAGTT CGCCAGGAAC CAGGCCATCT
 301 CTAGGTTGGA AGGATTGAGC AATCTCTACC AAATCTATGC AGAGAGCTTC
 351 AGAGAGTGGG AAGCCGATCC TACTAACCCA GCTCTCCGCG AGGAAATGCG
 401 TATTCAATTC AACGACATGA ACAGCGCCTT GACCACAGCT ATCCCATTGT
 451 TCGCAGTCCA GAACTACCAA GTTCCTCTCT TGTCCGTGTA CGTTCAAGCA
 501 GCTAATCTTC ACCTCAGCGT GCTTCGAGAC GTTAGCGTGT TTGGGCAAAG
 551 GTGGGGATTC GATGCTGCAA CCATCAATAG CCGTTACAAC GACCTTACTA
 601 GGCTGATTGG AAACTACACC GACCACGCTG TTCGTTGGTA CAACACTGGC
 651 TTGGAGCGTG TCTGGGGTCC TGATTCTAGA GATTGGATTA GATACAACCA
 701 GTTCAGGAGA GAATTGACCC TCACAGTTTT GGACATTGTG TCTCTCTTCC
 751 CGAACTATGA CTCCAGAACC TACCCTATCC GTACAGTGTC CCAACTTACC
 801 AGAGAAATCT ATACTAACCC AGTTCTTGAG AACTTCGACG GTAGCTTCCG
 851 TGGTTCTGCC CAAGGTATCG AAGGCTCCAT CAGGAGCCCA CACTTGATGG
 901 ACATCTTGAA CAGCATAACT ATCTACACCG ATGCTCACAG AGGAGAGTAT
 951 TACTGGTCTG ACACCAGAT CATGGCCTCT CCAGTTGGAT TCAGCGGGCC
1001 CGAGTTTACC TTTCCTCTCT ATGGAACTAT GGGAAACGCC GCTCCACAAC
1051 AACGTATCGT TGCTCAACTA GGTCAGGGTG TCTACAGAAC CTTGTCTTCC
1101 ACCTTGTACA GAAGACCCTT CAATATCGGT ATCAACAACC AGCAACTTTC
```

FIG. 9A

| | | | | | |
|---|---|---|---|---|---|
| 1151 | CGTTCTTGAC | GGAACAGAGT | TCGCCTATGG | AACCTCTTCT | AACTTGCCAT |
| 1201 | CCGCTGTTTA | CAGAAAGAGC | GGAACCGTTG | ATTCCTTGGA | CGAAATCCCA |
| 1251 | CCACAGAACA | ACAATGTGCC | ACCCAGGCAA | GGATTCTCCC | ACAGGTTGAG |
| 1301 | CCACGTGTCC | ATGTTCCGTT | CCGGATTCAG | CAACAGTTCC | GTGAGCATCA |
| 1351 | TCAGAGCTCC | TATGTTCTCA | TGGATTCATC | GTAGTGCTGA | GTTCAACAAT |
| 1401 | ATCATTCCTT | CCTCTCAAAT | CACCCAAATC | CCATTGACCA | AGTCTACTAA |
| 1451 | CCTTGGATCT | GGAACTTCTG | TCGTGAAAGG | ACCAGGCTTC | ACAGGAGGTG |
| 1501 | ATATTCTTAG | AAGAACTTCT | CCTGGCCAGA | TTAGCACCCT | CAGAGTTAAC |
| 1551 | ATCACTGCAC | CACTTTCTCA | AAGATATCGT | GTCAGGATTC | GTTACGCATC |
| 1601 | TACCACTAAC | TTGCAATTCC | ACACCTCCAT | CGACGGAAGG | CCTATCAATC |
| 1651 | AGGGTAACTT | CTCCGCAACC | ATGTCAAGCG | GCAGCAACTT | GCAATCCGGC |
| 1701 | AGCTTCAGAA | CCGTCGGTTT | CACTACTCCT | TTCAACTTCT | CTAACGGATC |
| 1751 | AAGCGTTTTC | ACCCTTAGCG | CTCATGTGTT | CAATTCTGGC | AATGAAGTGT |
| 1801 | ACATTGACCG | TATTGAGTTT | GTGCCTGCCG | AAGTTACCTT | CGAAGCCGAG |
| 1851 | TACGACCTGG | AGAGAGCCCA | GAAGGCTGTC | AATGAGCTCT | TCACGTCCAG |
| 1901 | CAATCAGATC | GGCCTGAAGA | CCGACGTCAC | TGACTACCAC | ATCGACCAAG |
| 1951 | TCTCCAACCT | CGTGGAGTGC | CTCTCCGATG | AGTTCTGCCT | CGACGAGAAG |
| 2001 | AAGGAGCTGT | CCGAGAAGGT | GAAGCATGCC | AAGCGTCTCA | GCGACGAGAG |
| 2051 | GAATCTCCTC | CAGGACCCCA | ATTTCCGCGG | CATCAACAGG | CAGCTCGACC |
| 2101 | GCGGCTGGCG | CGGCAGCACC | GACATCACGA | TCCAGGGCGG | CGACGATGTG |
| 2151 | TTCAAGGAGA | ACTACGTGAC | TCTCCTGGGC | ACTTTCGACG | AGTGCTACCC |
| 2201 | TACCTACTTG | TACCAGAAGA | TCGATGAGTC | CAAGCTCAAG | GCTTACACTC |
| 2251 | GCTACCAGCT | CCGCGGCTAC | ATCGAAGACA | GCCAAGACCT | CGAGATTTAC |

FIG. 9B

```
2301  CTGATCCGCT ACAACGCCAA GCACGAGACC GTCAACGTGC CCGGTACTGG
2351  TTCCCTCTGG CCGCTGAGCG CCCCCAGCCC GATCGGCAAG TGTGCCCACC
2401  ACAGCCACCA CTTCTCCTTG GACATCGATG TGGGCTGCAC CGACCTGAAC
2451  GAGGACCTCG GAGTCTGGGT CATCTTCAAG ATCAAGACCC AGGACGGCCA
2501  CGAGCGCCTG GGCAACCTGG AGTTCCTCGA GGGCAGGGCC CCCCTGGTCG
2551  GTGAGGCTCT GGCCAGGGTC AAGAGGGCTG AGAAGAAGTG GAGGGACAAG
2601  CGCGAGAAGC TCGAGTGGGA GACCAACATC GTTTACAAGG AGGCCAAGGA
2651  GAGCGTCGAC GCCCTGTTCG TGAACTCCCA GTACGACCGC CTGCAGGCCG
2701  ACACCAACAT CGCCATGATC CACGCTGCCG ACAAGAGGGT GCACAGCATT
2751  CGCGAGGCCT ACCTGCCTGA GCTGTCCGTG ATCCCTGGTG TGAACGCTGC
2801  CATCTTTGAG GAGCTGGAGG CCGCATCTT TACCGCATTC TCCCTGTACG
2851  ACGCCCGCAA CGTGATCAAG AACGGTGACT CAACAATGG CCTCAGCTGC
2901  TGGAACGTCA AGGGCCACGT GGACGTCGAG GAACAGAACA ACCACCGCTC
2951  CGTCCTGGTC GTCCCAGAGT GGGAGGCTGA GGTCTCCCAA GAGGTCCGCG
3001  TCTGCCCAGG CCGCGGCTAC ATTCTCAGGG TCACCGCTTA CAAGGAGGGC
3051  TACGGTGAGG GCTGTGTGAC CATCCACGAG ATCGAGAACA ACACCGACGA
3101  GCTTAAGTTC TCCAACTGCG TGGAGGAGGA GGTGTACCCA AACAACACCG
3151  TTACTTGCAA CGACTACACC GCCACCCAGG AGGAGTACGA GGGCACCTAC
3201  ACTTCCAGGA ACAGGGGCTA CGATGGTGCC TACGAGAGCA ACAGCAGCGT
3251  TCCTGCTGAC TACGCTTCCG CCTACGAGGA GAAGGCCTAC ACGGATGGCC
3301  GCAGGGACAA CCCTTGCGAG AGCAACCGCG GCTACGGCGA CTACACTCCC
3351  CTGCCCGCCG GCTACGTTAC CAAGGAGCTG GAGTACTTCC CGGAGACTGA
3401  CAAGGTGTGG ATCGAGATCG GCGAGACCGA GGGCACCTTC ATCGTGGACA
3451  GCGTGGAGCT GCTCCTGATG GAGGAGTAGA ATTC
```

FIG. 9C

Construction of CryIIB Synthetic Gene

CryIIA Template

Mutagenesis Oligonucleotides and PCR to make Fragments A - E

FIG. 11

```
  3 ATGGACAACAACCCAAACATCAACGAGTGCATCCCGTACAACTGCCTCAG  52
    |||||  |||||  ||  ||||||||  ||  |||||  ||  ||  ||  ||     |  ||
  1 ATGGATAACAATCCGAACATCAATGAATGCATTCCTTATAATTGTTTAAG  50

53 CAACCCTGAGGTCGAGGTGCTCGGCGGTGAGCGCATCGAGACCGGTTACA 102
    ||||||||  ||  ||  ||   |  ||  ||  ||   |  ||  ||  ||  |||||||
 51 TAACCCTGAAGTAGAAGTATTAGGTGGAGAAAGAATAGAAACTGGTTACA 100

103 CCCCCATCGACATCTCCCTCTCCCTCACGCAGTTCCTGCTCAGCGAGTTC 152
    ||||  |||||  ||  |||   |  ||  ||  |||||  ||  ||   |  ||  ||  ||
101 CCCCAATCGATATTTCCTTGTCGCTAACGCAATTTCTTTTGAGTGAATTT 150

153 GTGCCAGGCGCTGGCTTCGTCCTGGGCCTCGTGGACATCATCTGGGGCAT 202
    ||  ||  ||  |||||  ||  ||   |  ||  ||  ||  ||  ||  ||  |||||  ||
151 GTTCCCGGTGCTGGATTTGTGTTAGGACTAGTTGATATAATATGGGGAAT 200

203 CTTTGGCCCCTCCCAGTGGGACGCCTTCCTGGTGCAAATCGAGCAGCTCA 252
    |||||  |||||  ||  ||||||||  ||  ||  ||  |||||  ||  |||   |  |
201 TTTTGGTCCCTCTCAATGGGACGCATTTCTTGTACAAATTGAACAGTTAA 250

253 TCAACCAGAGGATCGAGGAGTTCGCCAGGAACCAGGCCATCAGCCGCCTG 302
    |   |||||  ||  ||  ||  ||  ||||| ||||||||  |||||         |  |
251 TTAACCAAAGAATAGAAGAATTCGCTAGGAACCAAGCCATTTCTAGATTA 300

303 GAGGGCCTCAGCAACCTCTACCAAATCTACGCTGAGAGCTTCCGCGAGTG 352
    ||  ||  ||  |||||  ||  ||  |||||  |||||  ||       ||   |  |||||
301 GAAGGACTAAGCAATCTTTATCAAATTTACGCAGAATCTTTTAGAGAGTG 350

353 GGAGGCCGACCCCACTAACCCAGCTCTCCGCGAGGAGATGCGCATCCAGT 402
    |||  ||  ||  ||  |||||  |||||     |   ||  ||||||||  ||  ||   |
351 GGAAGCAGATCCTACTAATCCAGCATTAAGAGAAGAGATGCGTATTCAAT 400

403 TCAACGACATGAACAGCGCCCTGACCACCGCCATCCCACTCTTCGCCGTC 452
    ||||  ||||||||||||  |||||  ||  |||||  ||  ||  ||  ||  ||  ||
401 TCAATGACATGAACAGTGCCCTTACAACCGCTATTCCTCTTTTTGCAGTT 450

453 CAGAACTACCAAGTCCCGCTCCTGTCCGTGTACGTCCAGGCCGCCAACCT 502
    ||  ||  ||  |||||  ||  ||   |  ||  ||  ||  ||  ||  ||  ||  ||     |
451 CAAAATTATCAAGTTCCTCTTTTATCAGTATATGTTCAAGCTGCAAATTT 500

503 GCACCTCAGCGTGCTGAGGGACGTCAGCGTGTTTGGCCAGAGGTGGGCT 552
    ||  |      ||  ||||  ||  ||     |||||||  ||  ||||||||  |
501 ACATTTATCAGTTTTGAGAGATGTTTCAGTGTTTGGACAAAGGTGGGGAT 550

553 TCGACGCCGCCACCATCAACAGCCGCTACAACGACCTCACCAGGCTGATC 602
    |  ||  ||||||  ||  ||||||  ||  ||  ||  ||     |  ||  |||||  ||
551 TTGATGCCGCGACTATCAATAGTCGTTATAATGATTTAACTAGGCTTATT 600
```

FIG. 13A

```
603  GGCAACTACACCGACCACGCTGTCCGCTGGTACAACACTGGCCTGGAGCG  652
     |||||||| || || || ||||| |||||||||| || ||  | |||||
601  GGCAACTATACAGATCATGCTGTACGCTGGTACAATACGGGATTAGAGCG  650

653  CGTCTGGGGCCCTGATTCTAGAGACTGGATTCGCTACAACCAGTTCAGGC  702
     || |||||| || |||||||||||| |||||  | || || || || ||
651  TGTATGGGGACCGGATTCTAGAGATTGGATAAGATATAATCAATTTAGAA  700

703  GCGAGCTGACCCTCACCGTCCTGGACATTGTGTCCCTCTTCCCGAACTAC  752
     | ||  | || || || ||  | || || || || || ||  |||||||
701  GAGAATTAACACTAACTGTATTAGATATCGTTTCTCTATTTCCGAACTAT  750

753  GACTCCCGCACCTACCCGATCCGCACCGTGTCCCAACTGACCCGCGAAAT  802
     ||    | || || || || || || || || |||||| | ||  |||||
751  GATAGTAGAACGTATCCAATTCGAACAGTTTCCCAATTAACAAGAGAAAT  800

803  CTACACCAACCCCGTCCTGGAGAACTTCGACGGTAGCTTCAGGGGCAGCG  852
     || || ||||| ||  | || || || || ||||| ||  | |||    |
801  TTATACAAACCCAGTATTAGAAAATTTTGATGGTAGTTTTCGAGGCTCGG  850

853  CCCAGGGCATCGAGGGCTCCATCAGGAGCCCACACCTGATGGACATCCTC  902
     | |||||||| || ||    || ||||| |||||  |||||| || ||
851  CTCAGGGCATAGAAGGAAGTATTAGGAGTCCACATTTGATGGATATACTT  900

903  AACAGCATCACTATCTACACCGATGCCCACCGCGGCGAGTACTACTGGTC  952
     || || || || ||  ||||| || || ||  | || || || ||  |||
901  AATAGTATAACCATCTATACGGATGCTCATAGAGGAGAATATTATTGGTC  950

953  CGGCCACCAGATCATGGCCTCCCCGGTCGGCTTCAGCGGCCCCGAGTTTA  1002
     || || || || |||||| ||||| ||   |||||| || || || || |
951  AGGGCATCAAATAATGGCTTCTCCTGTAGGGTTTTCGGGGCCAGAATTCA  1000

1003 CCTTTCCTCTCTACGGCACGATGGGCAACGCCGCTCCACAACAACGCATC  1052
     | ||||| || || || || ||||| ||||| |||| || ||||| | ||
1001 CTTTTCCGCTATATGGAACTATGGGAAATGCAGCTCCACAACAACGTATT  1050

1053 GTCGCTCAGCTGGGCCAGGGCGTCTACCGCACCCTGAGCTCCACCCTGTA  1102
     || |||||  || || |||||||| || | ||  ||   |||||| | ||
1051 GTTGCTCAACTAGGTCAGGGCGTGTATAGAACATTATCGTCCACCTTATA  1100

1103 CCGCAGGCCCTTCAACATCGGTATCAACAACCAGCAGCTGTCCGTCCTGG  1152
     | || || || || || || || || ||||| || || || || || | |
1101 TAGAAGACCTTTTAATATAGGGATAAATAATCAACAACTATCTGTTCTTG  1150

1153 ATGGCACTGAGTTCGCCTACGGCACCTCCTCCAACCTGCCCTCCGCTGTC  1202
     | || || || || || || || || || ||||||| |||| ||||||||
1151 ACGGGACAGAATTTGCTTATGGAACCTCCTCAAATTTGCCATCCGCTGTA  1200
```

FIG. 13B

```
1203 TACCGCAAGAGCGGCACGGTGGATTCCCTGGACGAGATCCCACCACAGAA 1252
     ||| | || ||||| ||||| ||||| ||||| || || || ||||||||
1201 TACAGAAAAAGCGGAACGGTAGATTCGCTGGATGAAATACCGCCACAGAA 1250

1253 CAACAATGTGCCCCCCAGGCAGGGTTTTTCCCACAGGCTCAGCCACGTGT 1302
     ||||| ||||| || ||||| || |||   || | | ||||| || |
1251 TAACAACGTGCCACCTAGGCAAGGATTTAGTCATCGATTAAGCCATGTTT 1300

1303 CCATGTTCCGCTCCGGCTTCAGCAACTCGTCCGTGAGCATCATCAGAGCT 1352
     | ||||| || || ||||| || ||         || || || || ||||||
1301 CAATGTTTCGTTCAGGCTTTAGTAATAGTAGTGTAAGTATAATAAGAGCT 1350

1353 CCTATGTTCTCCTGGATTCATCGCAGCGCGGAGTTCAACAATATCATTCC 1402
     |||||||||||| ||||| ||||| || || || || || ||||| |||||
1351 CCTATGTTCTCTTGGATACATCGTAGTGCTGAATTTAATAATATAATTCC 1400

1403 GTCCTCCCAAATCACCCAAATCCCCCTCACCAAGTCCACCAACCTGGGCA 1452
     || || ||||| || ||||| || | || || || || || || || |||
1401 TTCATCACAAATTACACAAATACCTTTAACAAAATCTACTAATCTTGGCT 1450

1453 GCGGCACCTCCGTGGTGAAGGGCCCAGGCTTCACGGGCGGCGACATCCTG 1502
     || || || || || || || || ||||| || || || || || || ||
1451 CTGGAACTTCTGTCGTTAAAGGACCAGGATTTACAGGAGGAGATATTCTT 1500

1503 CGCAGGACCTCCCCGGGCCAGATCAGCACCCTCCGCGTCAACATCACCGC 1552
     || || || || || |||||||| ||| | | || || || || || ||
1501 CGAAGAACTTCACCTGGCCAGATTTCAACCTTAAGAGTAAATATTACTGC 1550

1553 TCCCCTGTCCCAGAGGTACCGCGTCAGGATTCGCTACGCTAGCACCACCA 1602
     || | || || || || || || || |||||||||||| ||||| |
1551 ACCATTATCACAAAGATATCGGGTAAGAATTCGCTACGCTTCTACCACAA 1600

1603 ACCTGCAATTCCACACCTCCATCGACGGCAGGCCGATCAATCAGGGTAAC 1652
     |  | |||||||| || || || ||||| || || || ||||||||| ||
1601 ATTTACAATTCCATACATCAATTGACGGAAGACCTATTAATCAGGGGAAT 1650

1653 TTCTCCGCCACCATGTCCAGCGGCAGCAACCTCCAATCCGGCAGCTTCCG 1702
     || || || || |||    || || || ||  | || ||||| ||||| |
1651 TTTTCAGCAACTATGAGTAGTGGGAGTAATTTACAGTCCGGAAGCTTTAG 1700

1703 CACCGTGGGTTTCACCACCCCCTTCAACTTCTCCAACGGCTCCAGCGTTT 1752
     || || ||||| || || || || ||||| || || || || || || |
1701 GACTGTAGGTTTTACTACTCCGTTTAACTTTTCAAATGGATCAAGTGTAT 1750

1753 TCACCCTGAGCGCCCACGTGTTCAATTCCGGCAATGAGGTGTACATTGAC 1802
     | ||  | ||| || || || || || |||||||| |||||| || ||||| ||
1751 TTACGTTAAGTGCTCATGTCTTCAATTCAGGCAATGAAGTTTATATAGAT 1800
```

FIG. 13C

```
1803 CGCATTGAGTTCGTGCCAGCCGAGGTCACCTTCGAAGCCGAGTACGACCT 1852
     |  |||||  ||  ||  ||  ||  ||  ||  |||||  ||  ||  ||  ||  |
1801 CGAATTGAATTTGTTCCGGCAGAAGTAACCTTTGAGGCAGAATATGATTT 1850

1853 GGAGAGAGCCCAGAAGGCTGTCAATGAGCTCTTCACGTCCAGCAATCAGA 1902
     ||  |||||  ||  |||||  ||  ||||||||  ||  ||  ||      ||||||  |
1851 AGAAAGAGCACAAAAGGCGGTGAATGAGCTGTTTACTTCTTCCAATCAAA 1900

1903 TCGGCCTGAAGACCGACGTCACTGACTACCACATCGACCAAGTCTCCAAC 1952
     ||||    |  ||  ||  ||  ||  ||  ||  ||  ||  ||  |||||  |||||
1901 TCGGGTTAAAAACAGATGTGACGGATTATCATATTGATCAAGTATCCAAT 1950

1953 CTCGTGGAGTGCCTCTCCGATGAGTTCTGCCTCGACGAGAAGAAGGAGCT 2002
     |  ||  |||||    |  ||  |||||  ||  ||  ||  ||  ||  ||  ||  |
1951 TTAGTTGAGTGTTTATCTGATGAATTTTGTCTGGATGAAAAAAAGAATT 2000

2003 GTCCGAGAAGGTGAAGCATGCCAAGCGTCTCAGCGACGAGAGGAATCTCC 2052
     ||||||||  ||  ||  |||||  |||||  ||  ||  ||  |||  |||||  |  |
2001 GTCCGAGAAAGTCAAACATGCGAAGCGACTTAGTGATGAGCGGAATTTAC 2050

2053 TCCAGGACCCCAATTTCCGCGGCATCAACAGGCAGCTCGACCGCGGCTGG 2102
     |  ||  ||  ||  ||  ||    |  ||  |||||  ||  ||  ||  |||||  |||||
2051 TTCAAGATCCAAACTTTAGAGGGATCAATAGACAACTAGACCGTGGCTGG 2100

2103 CGCGGCAGCACCGACATCACGATCCAGGGCGGCGACGATGTGTTCAAGGA 2152
       |  ||  ||  ||  ||  ||  ||  |||||  ||  |||||  ||  ||  |||||  ||
2101 AGAGGAAGTACGGATATTACCATCCAAGGAGGCGATGACGTATTCAAAGA 2150

2153 GAACTACGTGACTCTCCTGGGCACTTTCGACGAGTGCTACCCTACCTACT 2202
     |||  |||||  ||  ||  ||||  ||  ||  ||  ||||||||  ||  ||  ||  |
2151 GAATTACGTTACGCTATTGGGTACCTTTGATGAGTGCTATCCAACGTATT 2200

2203 TGTACCAGAAGATCGATGAGTCCAAGCTCAAGGCTTACACTCGCTACCAG 2252
     |  ||  ||  ||  ||  ||||||||  ||    |  ||  ||  ||  ||  ||  |||||
2201 TATATCAAAAAATAGATGAGTCGAAATTAAAAGCCTATACCCGTTACCAA 2250

2253 CTCCGCGGCTACATCGAAGACAGCCAAGACCTCGAGATTTACCTGATCCG 2302
     |    |  ||  ||  ||||||||  ||  ||||||  |  ||  ||  ||    |  ||  ||
2251 TTAAGAGGGTATATCGAAGATAGTCAAGACTTAGAAATCTATTTAATTCG 2300

2303 CTACAACGCCAAGCACGAGACCGTCAACGTGCCCGGTACTGGTTCCCTCT 2352
     ||||||  |||||  |||||  ||  ||  ||  |||||  |||||  ||||||  |  |
2301 CTACAATGCCAAACACGAAACAGTAAATGTGCCAGGTACGGGTTCCTTAT 2350

2353 GGCCGCTGAGCGCCCCCAGCCCGATCGGCAAGTGTGCCCACCACAGCCAC 2402
     |||||||          |||||  ||  ||  |||||  ||  |||||||||  ||      |||
2351 GGCCGCTTTCAGCCCCAAGTCCAATCGGAAAATGTGCCCATCATTCCCAT 2400
```

FIG. 13D

```
2403 CACTTCTCCTTGGACATCGATGTGGGCTGCACCGACCTGAACGAGGACCT 2452
     || |||||||||||||| ||||| || || || ||| | || |||||| |
2401 CATTTCTCCTTGGACATTGATGTTGGATGTACAGACTTAAATGAGGACTT 2450

2453 CGGAGTCTGGGTCATCTTCAAGATCAAGACCCAGGACGGCCACGAGCGCC 2502
     || || ||||| || ||||||||| ||||| || || ||||| ||  | |
2451 AGGTGTATGGGTGATATTCAAGATTAAGACGCAAGATGGCCATGAAAGAC 2500

2503 TGGGCAACCTGGAGTTCCTCGAGGGCAGGGCCCCCCTGGTCGGTGAGGCT 2552
     | || || || || || || ||||| || || || ||  | || || ||
2501 TAGGAAATCTAGAATTTCTCGAAGGAAGAGCACCATTAGTAGGAGAAGCA 2550

2553 CTGGCCAGGGTCAAGAGGGCTGAGAAGAAGTGGAGGGACAAGCGCGAGAA 2602
     || ||  | || || || || ||||| || ||||| || || || || ||
2551 CTAGCTCGTGTGAAAAGAGCGGAGAAAAAATGGAGAGACAAACGTGAAAA 2600

2603 GCTCGAGTGGGAGACCAACATCGTTTACAAGGAGGCCAAGGAGAGCGTCG 2652
     | || ||||| || || || ||||| || ||||| || ||    || |
2601 ATTGGAATGGGAAACAAATATTGTTTATAAGAGGCAAAAGAATCTGTAG 2650

2653 ACGCCCTGTTCGTGAACTCCCAGTACGACCGCCTGCAGGCCGACACCAAC 2702
     | || | || || ||||| || || ||  | | || || || |||||||
2651 ATGCTTTATTTGTAAACTCTCAATATGATAGATTACAAGCGGATACCAAC 2700

2703 ATCGCCATGATCCACGCTGCCGACAAGAGGGTGCACAGCATTCGCGAGGC 2752
     ||||| ||||| || || || || || || || |||||||| || ||
2701 ATCGCGATGATTCATGCGGCAGATAAACGCGTTCATAGCATTCGAGAAGC 2750

2753 CTACCTGCCTGAGCTGTCCGTGATCCCTGGTGTGAACGCTGCCATCTTTG 2802
     || |||||||||||||| ||||| || |||||| || || || || ||||
2751 TTATCTGCCTGAGCTGTCTGTGATTCCGGGTGTCAATGCGGCTATTTTTG 2800

2803 AGGAGCTGGAGGGCCGCATCTTTACCGCATTCTCCCTGTACGACGCCCGC 2852
     | ||  | || || || || || |||||||||||| || || || || |
2801 AAGAATTAGAAGGGCGTATTTTCACTGCATTCTCCCTATATGATGCGAGA 2850

2853 AACGTGATCAAGAACGGTGACTTCAACAATGGCCTCAGCTGCTGGAACGT 2902
     || || || || || || ||||| || || |||||| | ||||||||||
2851 AATGTCATTAAAAATGGTGATTTTAATAATGGCTTATCCTGCTGGAACGT 2900

2903 CAAGGGCCACGTGGACGTCGAGGAACAGAACAACCACCGCTCCGTCCTGG 2952
     || ||  || || || || || |||||||||||||| || |||||| |
2901 GAAAGGGCATGTAGATGTAGAAGAACAAAACAACCACCGTTCGGTCCTTG 2950

2953 TCGTCCCAGAGTGGGAGGCTGAGGTCTCCCAAGAGGTCCGCGTCTGCCCA 3002
     | || || || ||||| ||||||||||| || || || || || || ||
2951 TTGTTCCGGAATGGGAAGCAGAAGTGTCACAAGAAGTTCGTGTCTGTCCG 3000
```

FIG. 13E

```
3003 GGCCGCGGCTACATTCTCAGGGTCACCGCTTACAAGGAGGGCTACGGTGA 3052
     || ||  |||||  ||  ||  |  ||||||  ||  |||||||||||  ||  ||  ||
3001 GGTCGTGGCTATATCCTTCGTGTCACAGCGTACAAGGAGGGATATGGAGA 3050

3053 GGGCTGTGTGACCATCCACGAGATCGAGAACAACACCGACGAGCTTAAGT 3102
     ||  ||  ||  |||||  ||  |||||||||||||||  ||  |||||  ||  ||||
3051 AGGTTGCGTAACCATTCATGAGATCGAGAACAATACAGACGAACTGAAGT 3100

3103 TCTCCAACTGCGTGGAGGAGGAGGTGTACCCAAACAACACCGTTACTTGC 3152
     |    ||||||  ||  ||  |||||  ||  ||  ||||||||||  ||  ||  ||
3101 TTAGCAACTGTGTAGAAGAGGAAGTATATCCAAACAACACGGTAACGTGT 3150

3153 AACGACTACACCGCCACCCAGGAGGAGTACGAGGGCACCTACACTTCCAG 3202
     ||  ||  ||  ||  ||  ||  ||  ||  ||  ||  |||||  ||  ||||||||  |
3151 AATGATTATACTGCGACTCAAGAAGAATATGAGGGTACGTACACTTCTCG 3200

3203 GAACAGGGGCTACGATGGTGCCTACGAGAGCAACAGCAGCGTTCCTGCTG 3252
     ||  |  ||  ||  ||  ||  ||  |||||  ||  |||||           ||  ||  ||||
3201 TAATCGAGGATATGACGGAGCCTATGAAAGCAATTCTTCTGTACCAGCTG 3250

3253 ACTACGCTTCCGCCTACGAGGAGAAGGCCTACACGGATGGCCGCAGGGAC 3302
     |  ||  ||  ||  |||||  ||  ||  ||  ||  ||  ||  |||||  ||  ||  |||
3251 ATTATGCATCAGCCTATGAAGAAAAGCATATACAGATGGACGAAGAGAC 3300

3303 AACCCTTGCGAGAGCAACCGCGGCTACGGCGACTACACTCCCCTGCCCGC 3352
     ||  |||||  ||        |||  |  ||  ||  ||  ||  |||||  ||  ||  ||  ||
3301 AATCCTTGTGAATCTAACAGAGGATATGGGGATTACACACCACTACCAGC 3350

3353 CGGCTACGTTACCAAGGAGCTGGAGTACTTCCCGGAGACTGACAAGGTGT 3402
     |||||  ||  ||  ||  ||    |  ||||||||||  ||  ||  ||  |||||  |
3351 TGGCTATGTGACAAAAGAATTAGAGTACTTCCCAGAAACCGATAAGGTAT 3400

3403 GGATCGAGATCGGCGAGACCGAGGGCACCTTCATCGTGGACAGCGTGGAG 3452
     ||||  ||||||||  ||  ||  ||  ||  ||  |||||||||||||||||||||
3401 GGATTGAGATCGGAGAAACGGAAGGAACATTCATCGTGGACAGCGTGGAA 3450

3453 CTGCTCCTGATGGAGGAGTA 3472
     |  ||  ||  |||||||||  ||
3451 TTACTTCTTATGGAGGAATA 3470
```

FIG. 13F

```
  1  ATGGACAACA ACGTCTTGAA CTCTGGTAGA ACAACCATCT GCGACGCATA
 51  CAACGTCGTG GCTCACGATC CATTCAGCTT CGAACACAAG AGCCTCGACA
101  CTATTCAGAA GGAGTGGATG GAATGGAAAC GTACTGACCA CTCTCTCTAC
151  GTCGCACCTG TGGTTGGAAC AGTGTCCAGC TTCCTTCTCA AGAAGGTCGG
201  CTCTCTCATC GGAAAACGTA TCTTGTCCGA ACTCTGGGGT ATCATCTTTC
251  CATCTGGGTC CACTAATCTC ATGCAAGACA TCTTGAGGGA GACCGAACAG
301  TTTCTCAACC AGCGTCTCAA CACTGATACC TTGGCTAGAG TCAACGCTGA
351  GTTGATCGGT CTCCAAGCAA ACATTCGTGA GTTCAACCAG CAAGTGGACA
401  ACTTCTTGAA TCCAACTCAG AATCCTGTGC CTCTTTCCAT CACTTCTTCC
451  GTGAACACTA TGCAGCAACT CTTCCTCAAC AGATTGCCTC AGTTTCAGAT
501  TCAAGGCTAC CAGTTGCTCC TTCTTCCACT CTTTGCTCAG GCTGCCAACA
551  TGCACTTGTC CTTCATACGT GACGTGATCC TCAACGCTGA CGAATGGGGA
601  ATCTCTGCAG CCACTCTTAG GACATACAGA GACTACTTGA GGAACTACAC
651  TCGTGATTAC TCCAACTATT GCATCAACAC TTATCAGACT GCCTTTCGTG
701  GACTCAATAC TAGGCTTCAC GACATGCTTG AGTTCAGGAC CTACATGTTC
751  CTTAACGTGT TTGAGTACGT CAGCATTTGG AGTCTCTTCA AGTACCAGAG
801  CTTGATGGTG TCCTCTGGAG CCAATCTCTA CGCCTCTGGC AGTGGACCAC
851  AGCAAACTCA GAGCTTCACA GCTCAGAACT GGCCATTCTT GTATAGCTTG
901  TTCCAAGTCA ACTCCAACTA CATTCTCAGT GGTATCTCTG GGACCAGACT
```

FIG. 14A

```
 951  CTCCATAACC TTTCCCAACA TTGGTGGACT TCCAGGCTCC ACTACAACCC
1001  ATAGCCTTAA CTCTGCCAGA GTGAACTACA GTGGAGGTGT CAGCTCTGGA
1051  TTGATTGGTG CAACTAACTT GAACCACAAC TTCAATTGCT CCACCGTCTT
1101  GCCACCTCTG AGCACACCGT TTGTGAGGTC CTGGCTTGAC AGCGGTACTG
1151  ATCGCGAAGG AGTTGCTACC TCTACAAACT GGCAAACCGA GTCCTTCCAA
1201  ACCACTCTTA GCCTTCGGTG TGGAGCTTTC TCTGCACGTG GAATTCAAA
1251  CTACTTTCCA GACTACTTCA TTAGGAACAT CTCTGGTGTT CCTCTCGTCA
1301  TCAGGAATGA AGACCTCACC CGTCCACTTC ATTACAACCA GATTAGGAAC
1351  ATCGAGTCTC CATCCGGTAC TCCAGGAGGT GCAAGAGCTT ACCTCGTGTC
1401  TGTCCATAAC AGGAAGAACA ACATCTACGC TGCCAACGAG AATGGCACCA
1451  TGATTCACCT TGCACCAGAA GATTACACTG GATTCACCAT CTCTCCAATC
1501  CATGCTACCC AAGTGAACAA TCAGACACGC ACCTTCATCT CCGAAAAGTT
1551  CGGAAATCAA GGTGACTCCT TGAGGTTCGA GCAATCCAAC ACTACCGCTA
1601  GGTACACTTT GAGAGGCAAT GGAAACAGCT ACAACCTTTA CTTGAGAGTT
1651  AGCTCCATTG GTAACTCCAC CATCCGTGTT ACCATCAACG GACGTGTTTA
1701  CACAGTCTCT AATGTGAACA CTACAACGAA CAATGATGGC GTTAACGACA
1751  ACGGAGCCAG ATTCAGCGAC ATCAACATTG CAACATCGT GGCCTCTGAC
1801  AACACTAACG TTACTTTGGA CATCAATGTG ACCCTCAATT CTGGAACTCC
1851  ATTTGATCTC ATGAACATCA TGTTTGTGCC AACTAACCTC CCTCCATTGT
1901  ACTAATGAGA TCTAAGCTT
```

FIG. 14B 5,689,052

SYNTHETIC DNA SEQUENCES HAVING ENHANCED EXPRESSION IN MONOCOTYLEDONOUS PLANTS AND METHOD FOR PREPARATION THEREOF

This is a File Wrapper Continuation of application Ser. No. 08/172,333, filed Dec. 22, 1993, now abandoned.

FIELD OF THE INVENTION

This invention generally relates to genetic engineering and more particularly to methods for enhancing the expression of a DNA sequence in a monocotyledonous plant and/or increasing the frequency of obtaining transgenic monocotyledonous plants which accumulate useful amounts of a transgenic protein.

BACKGROUND OF THE INVENTION

One of the primary goals of plant genetic research is to provide transgenic plants which express a foreign gene in an amount sufficient to confer the desired phenotype to the plant. Significant advances have been made in pursuit of this goal, but the expression of some foreign genes in transgenic plants remains problematic. It is believed that numerous factors are involved in determining the ultimate level of expression of a foreign gene in a plant, and the level of mRNA produced in the plant cells is believed to be a major factor that limits the amount of a foreign protein that is expressed in a plant.

It has been suggested that the low levels of expression observed for some foreign proteins expressed in monocotyledonous plants (monocots) may be due to low steady state levels of mRNA in the plant as a result of the nature of the coding sequence of the structural gene. This could be the result of a low frequency of full-length RNA synthesis caused by the premature termination of RNA during transcription or due to unexpected mRNA processing during transcription. Alternatively, full-length RNA could be produced, but then processed by splicing or polyA addition in the nucleus in a fashion that creates a nonfunctional mRNA. It is also possible for the mRNA to be properly synthesized in the nucleus, yet not be suitable for sufficient or efficient translation in the plant cytoplasm.

Various nucleotide sequences affect the expression levels of a foreign DNA sequence introduced into a plant. These include the promoter sequence, intron sequences, the structural coding sequence that encodes the desired foreign protein, 3' untranslated sequences, and polyadenylation sites. Because the structural coding region introduced into the plant is often the only "non-plant" or "non-plant related" sequence introduced, it has been suggested that it could be a significant factor affecting the level of expression of the protein. In this regard, investigators have determined that typical plant structural coding sequences preferentially utilize certain codons to encode certain amino acids in a different frequency than the frequency of usage appearing in bacterial or non-plant coding sequences. Thus it has been suggested that the differences between the typical codon usage present in plant coding sequences as compared to the typical codon usage present in the foreign coding sequence is a factor contributing to the low levels of the foreign mRNA and foreign protein produced in transgenic monocot plants. These differences could contribute to the low levels of mRNA or protein of the foreign coding sequence in a transgenic plant by affecting the transcription or translation of the coding sequence or proper mRNA processing. Recently, attempts have been made to alter the structural coding sequence of a desired polypeptide or protein in an effort to enhance its expression in the plant. In particular, investigators have altered the codon usage of foreign coding sequences in an attempt to enhance its expression in a plant. Most notably, the sequence encoding insecticidal crystal proteins of *B. thuringiensis* (B.t.) has been modified in various ways to enhance its expression in a plant, particularly monocotyledonous plants, to produce commercially viable insect-tolerant plants.

In the European Patent Application No. 0359472 of Adang et al., a synthetic B.t. toxin gene was suggested which utilized codons preferred in highly expressed monocotyledonous or dicotyledonous proteins. In the Adang et al. gene design, the resulting synthetic gene closely resembles a typical plant gene. That is, the native codon usage in the B.t. toxin gene was altered such that the frequency of usage of the individual codons was made to be nearly identical to the frequency of usage of the respective codons in typical plant genes. Thus, the codon usage in a synthetic gene prepared by the Adang et al. design closely resembles the distribution frequency of codon usage found in highly expressed plant genes.

Another approach to altering the codon usage of a B.t. toxin gene to enhance its expression in plants was described in Fischhoff et al., European Patent Application No. 0385962. In Fischhoff et al., a synthetic plant gene was prepared by modifying the coding sequence to remove all ATTTA sequences and certain identified putative polyadenylation signals. Moreover, the gene sequence was preferably scanned to identify regions with greater than four consecutive adenine or thymine nucleotides and if there were more than one of the minor polyadenylation signals identified within ten nucleotides of each other, then the nucleotide sequence of this region was altered to remove these signals while maintaining the original encoded amino acid sequence. The overall G+C content was also adjusted to provide a final sequence having a G+C ratio of about 50%.

PCT Publication No WO 91/16432 of Cornelissen et al. discloses a method of modifying a DNA sequence encoding a B.t. crystal protein toxin wherein the gene was modified by reducing the A+T content by changing the adenine and thymine bases to cytosine and guanine while maintaining a coding sequence for the original protein toxin. The modified gene was expressed in tobacco and potato. No data was provided for maize or any other monocot.

SUMMARY OF THE INVENTION

Briefly, a method for modifying a nucleotide sequence for enhanced accumulation of its protein or polypeptide product in a monocotyledonous plant is provided. Surprisingly, it has been found that by reducing the frequency of usage of rare and semi-rare monocotyledonous codons in a foreign gene to be introduced into a monocotyledonous plant by substituting the rare and semi-rare codons with more preferred monocotyledonous codons, the accumulation of the protein in the monocot plant expressing the foreign gene and/or the frequency of obtaining a transformed monocotyledonous plant which accumulates the insecticidal B.t. crystal protein at levels greater than 0.005 wt % of total soluble protein is significantly improved. Thus, the present invention is drawn to a method for modifying a structural coding sequence encoding a polypeptide to enhance accumulation of the polypeptide in a monocotyledonous plant which comprises determining the amino acid sequence of the polypeptide encoded by the structural coding sequence and reducing the frequency of rare and semi-rare monocotyledonous codons in a coding sequence by substituting the rare and semi-rare monocotyledonous codons in the coding sequence with a more-preferred monocotyledonous codon which codes for the same amino acid.

The present invention is further directed to synthetic structural coding sequences produced by the method of this invention where the synthetic coding sequence expresses its protein product in monocotyledonous plants at levels significantly higher than corresponding wild-type coding sequences.

The present invention is also directed to a novel method comprising reducing the frequency of rare and semi-rare monocotyledonous codons in the nucleotide sequence by substituting the rare and semi-rare codons with a more-preferred monocotyledonous codon, reducing the occurrence of polyadenylation signals and intron splice sites in the nucleotide sequence, removing self-complementary sequences in the nucleotide sequence and replacing such sequences with nonself-complementary nucleotides while maintaining a structural gene encoding the polypeptide, and reducing the frequency of occurrence of 5'-CG-3' dinucleotide pairs in the nucleotide sequence, wherein these steps are performed sequentially and have a cumulative effect resulting in a nucleotide sequence containing a preferential utilization of the more-preferred monocotyledonous codons for monocotyledonous plants for a majority of the amino acids present in the polypeptide.

The present invention is also directed to a method which further includes analyzing the coding sequence in successive six nucleotide fragments (six-mers) and altering the sequence based on the frequency of appearance of the six-mers as compared to the frequency of appearance of the rarest 284, 484 and 664 six-mers in monocotyledonous plants. More particularly, the coding sequence to be introduced into a plant is analyzed and altered in a manner that (a) reduces the frequency of appearance of any of the rarest 284 monocotyledonous six-mers to produce a coding sequence with less than about 0.5% of the rarest 284 six-mers, (b) reduces the frequency of appearance of any of the rarest 484 monocotyledonous six-mers to produce a coding sequence with less than about 1.5% of the rarest 484 six-mers, and (c) reduces the frequency of appearance of any of the rarest 664 monocotyledonous six-mers to produce a coding sequence with less than about 3% of the rarest 664 six-mers.

The present invention is further directed to monocotyledonous plants and seeds containing synthetic DNA sequences prepared by the methods of this invention.

Therefore, it is an object of the present invention to provide synthetic DNA sequences that are capable of expressing their respective proteins at relatively higher levels that the corresponding wild-type DNA sequence and methods for the preparation of such sequences. It is a particular object of this invention to provide synthetic DNA sequences that express a crystal protein toxin gene of B.t. at such relatively high levels.

It is also an object of the present invention to provide a method for improving protein accumulation from a foreign gene transformed into a monocotyledonous plant (particularly maize) and/or improving the frequency of obtaining transformed monocotyledonous plants (particularly maize) which accumulate the insecticidal B.t. crystal protein at levels greater than 0.005 wt. % of total soluble protein, by altering the nucleotide sequence in the coding region of the foreign gene by reducing the frequency of codons that are infrequently utilized in monocotyledonous plant genes and substituting frequently utilized monocotyledonous plant codons therefor.

BRIEF DESCRIPTION OF THE DRAWING FIGURES

FIG. 1 is a table listing the frequency of abundance of each of the codons for each amino acid for typical monocotyledonous plant genes.

FIG. 2a is a list of the most rare 284 six-mers in typical monocotyledonous plant genes.

FIG. 2b and 2c are a list of the most rare 484 six-mers in typical monocotyledonous plant genes.

FIGS. 2d and 2e are a list of the most rare 664 six-mers in typical monocotyledonous plant genes.

FIGS. 3a, 3b and 3c are the DNA sequence of B.t. var. kurstaki (B.t. k.) CryIA(b) modified in accordance with the teachings of the present invention (SEQ ID NO:1).

FIGS. 4a and b are the DNA sequence of the CryIIB insecticidal protein modified in accordance with the teachings of the present invention (SEQ ID NO:2).

FIGS. 5a b and c are the DNA sequence of a synthetic DNA sequence encoding B.t. var. kurstaki CryIA(b)/CryIA (c) modified in accordance with one method of the prior art (SEQ ID NO:3).

Figure 6:
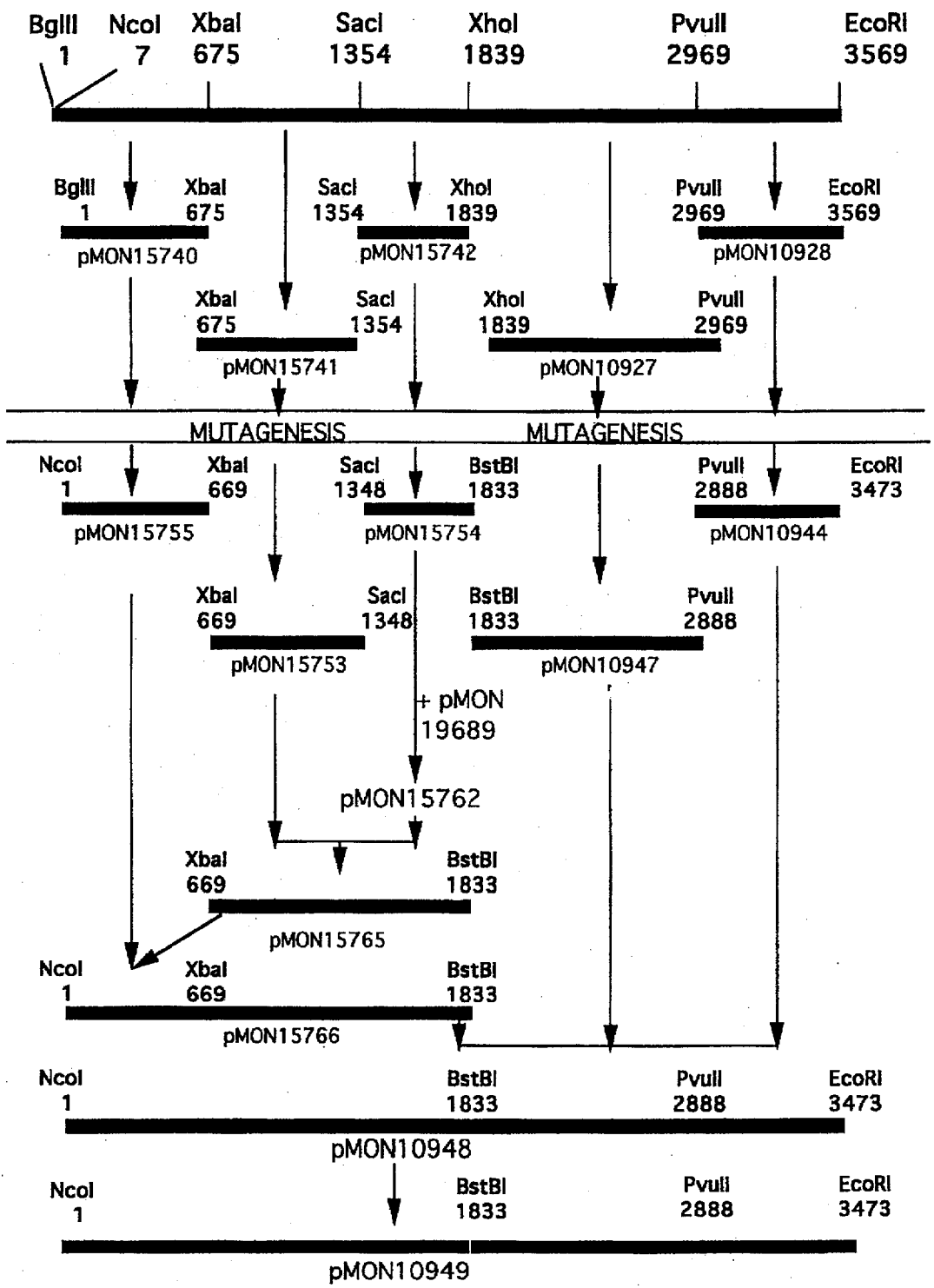
Figure 7:
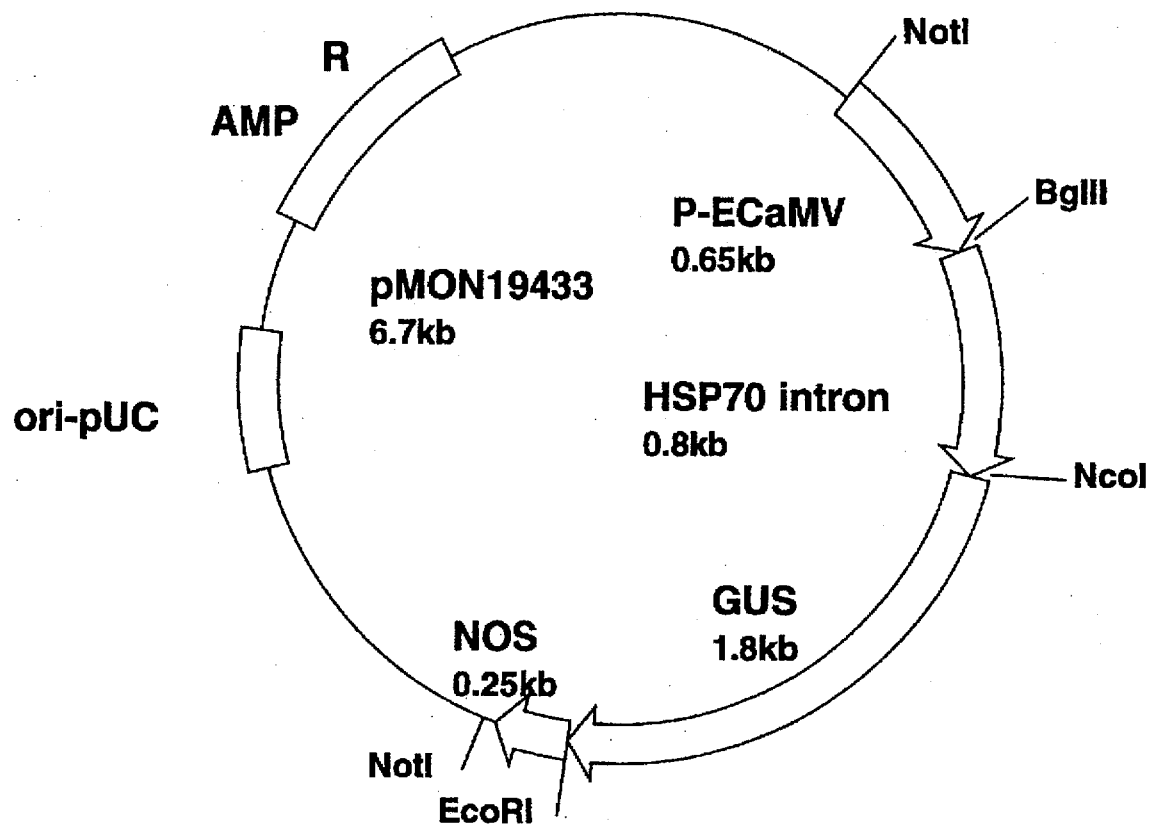

FIG. 6 illustrates the construction of the intact CryIA(b) synthetic gene from subclones and the strategy involved;

FIG. 7 is a plasmid map of pMON19433.

Figure 8:
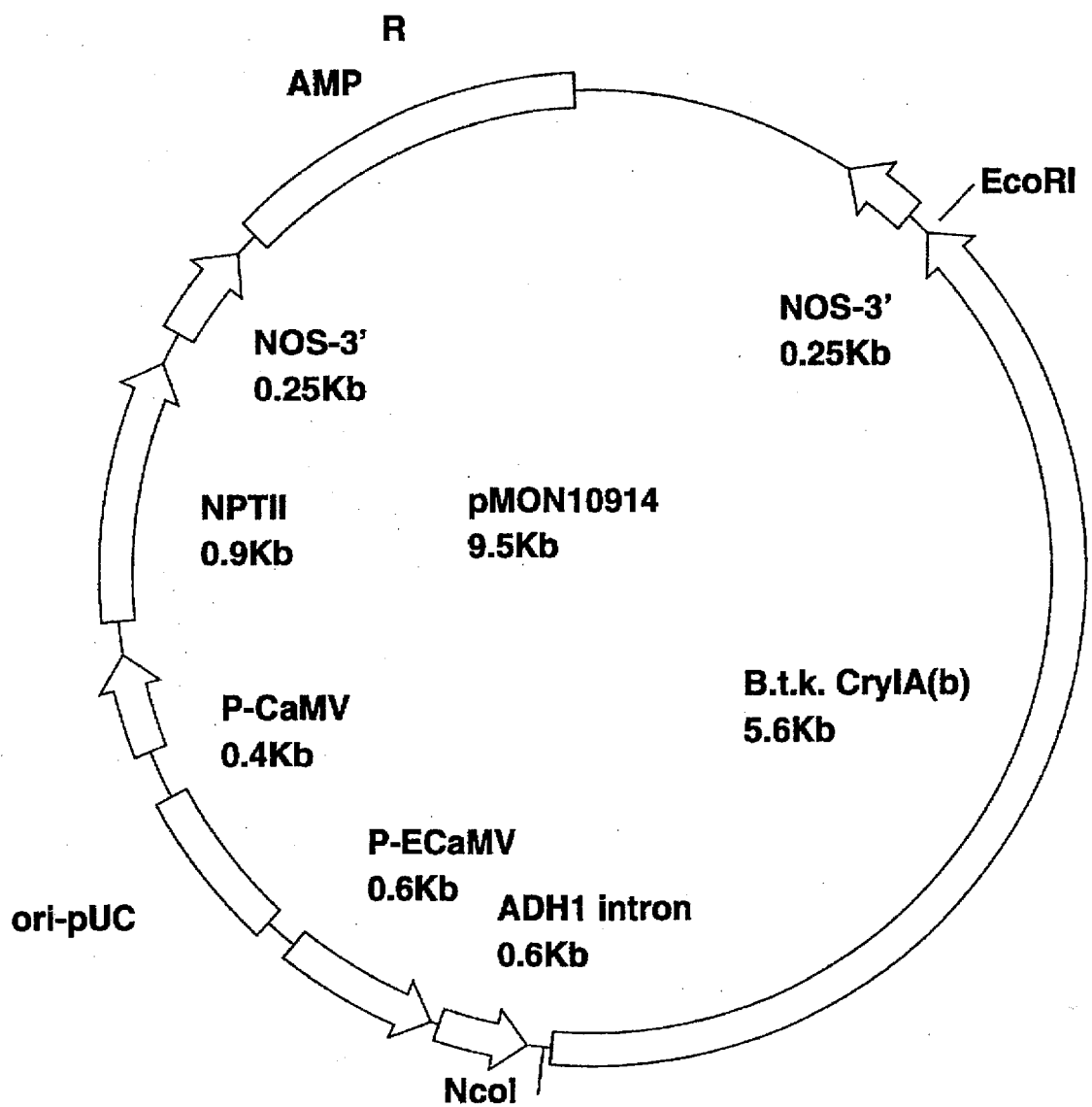

FIG. 8 is a plasmid map of pMON10914.

FIGS. 9a, b and c are the DNA sequence of a B.t. var kurstaki insecticidal protein wherein the front half of the coding sequence is not modified and the back half is modified in accordance with the method of the present invention (SEQ ID NO:105).

Figure 10:
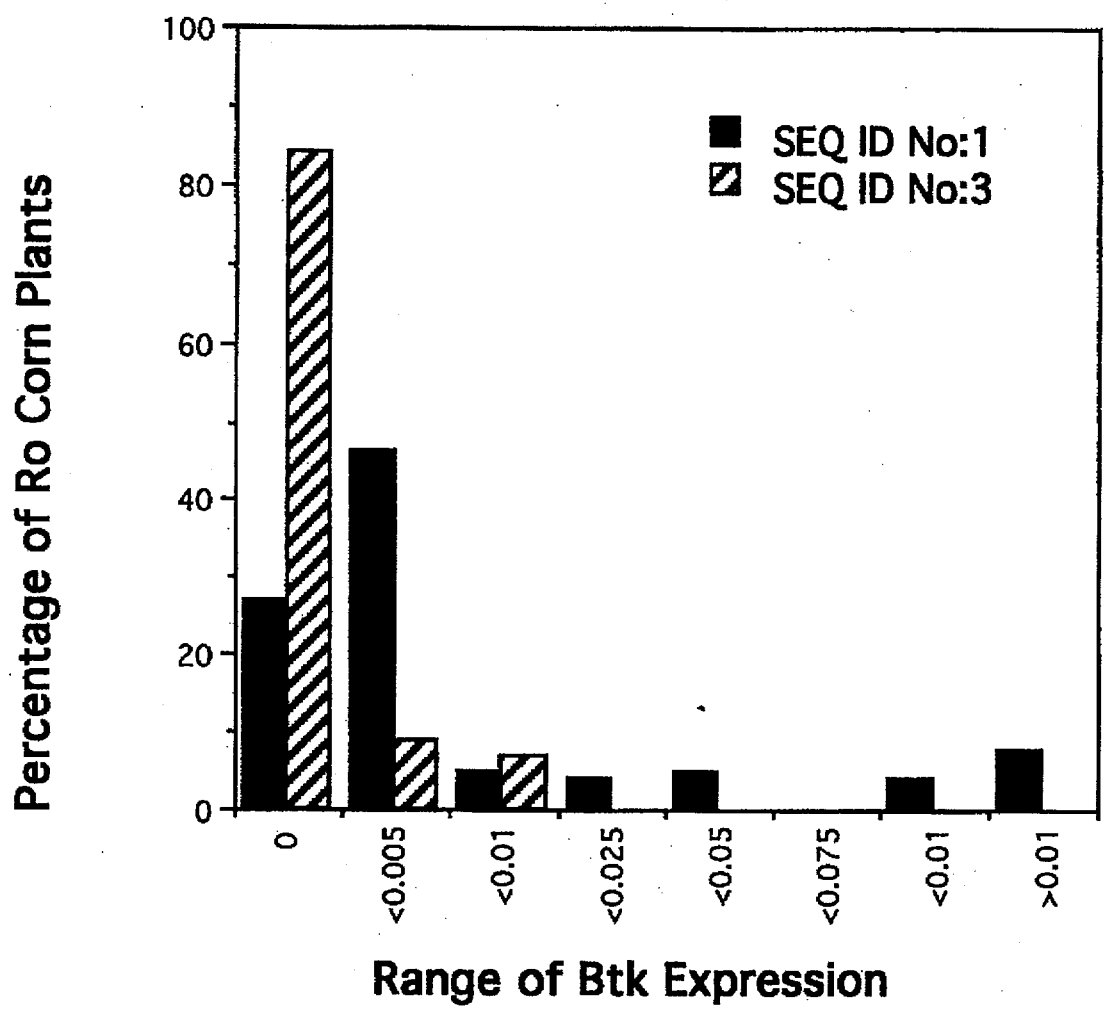

FIG. 10 is a graphical representation of the range of expression of a B.t. DNA sequence modified in accordance with the method of the present invention in R0 corn plants as compared to a B.t. DNA sequence prepared by a method of the prior art.

FIG. 11 illustrates the method of construction of the CryIIB DNA sequence modified in accordance with a second embodiment of the present invention.

Figure 12:
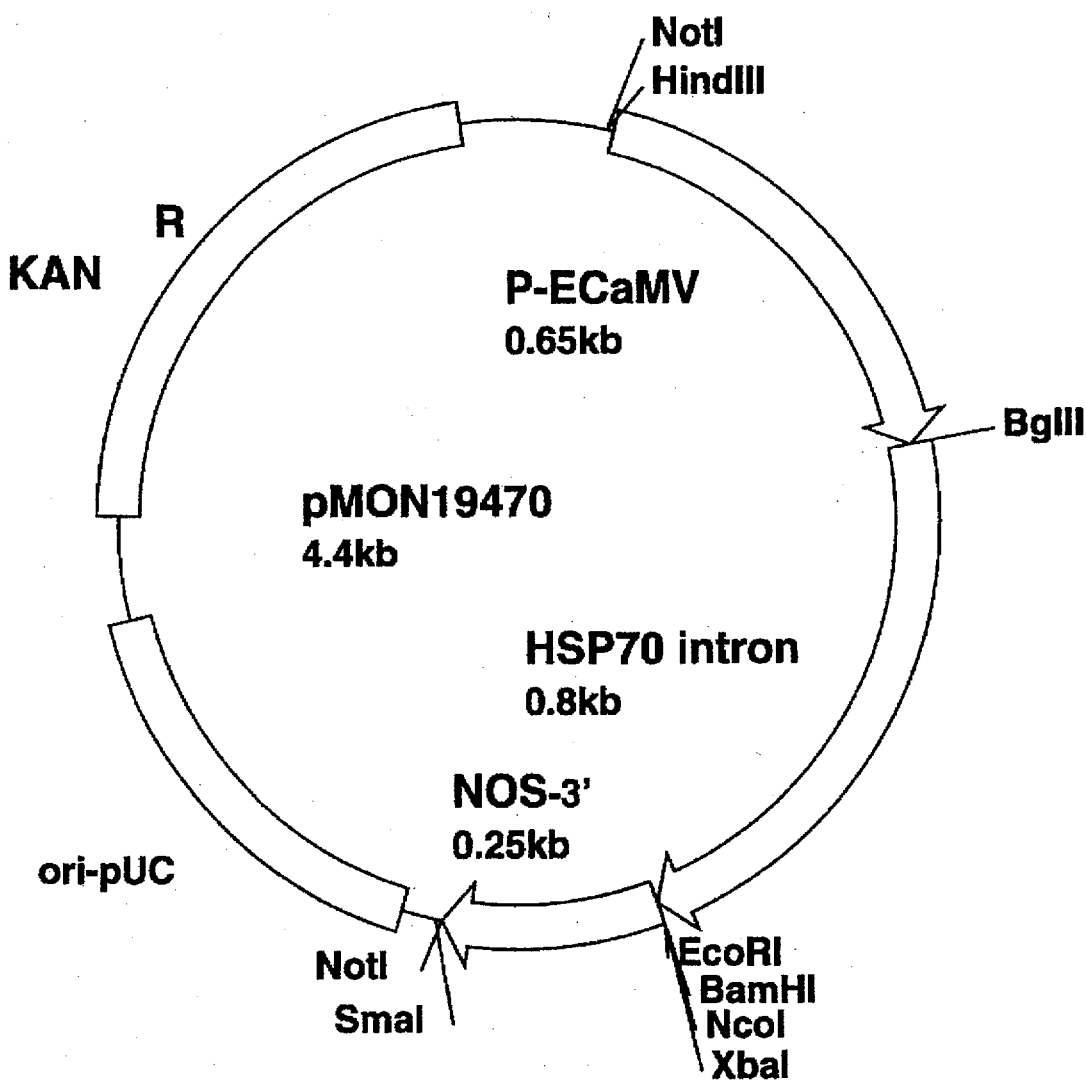

FIG. 12 is a plasmid map of pMON19470.

FIGS. 13a, b, c, d, e and f are a comparison of the wild-type bacterial B. t. k. CryIA(b) DNA coding sequence (SEQ ID NO:164) with the modified B. t. k. CryIA(b) DNA sequence as shown in FIG. 3 and identified as SEQ ID NO:1.

FIGS. 14a and b are the DNA sequence of the CryIIA synthetic DNA sequence which was used as the starting DNA sequence for the preparation of the CryIIB synthetic DNA according to one method of the present invention (SEQ ID NO:106).

DETAILED DESCRIPTION OF THE PREFERRED EMBODIMENTS

The following definitions are provided for clarity of the terms used in the description of this invention.

"Rare monocotyledonous codons" refers to codons which have an average frequency of abundance in monocotyledonous plant genes of less than 10%. That is, for purposes of the present invention the rare monocotyledonous codons include GTA, AGA, CGG, CGA, AGT, TCA, ATA, TTA and CTA.

"Semi-rare monocotyledonous codons" refers to codons which have an average frequency of abundance in monocotyledonous plant genes of between 10%–20%. That is, for purposes of the present invention the semi-rare monocotyledonous codons include GGG, GGA, GAA, GCA, CGT, TCG, TCT, AAA, ACA, ACT, TGT, TAT, TTG, CTT and CCT.

An "average monocotyledonous codon" refers to codons which have an average frequency of greater than about 20%, but are not a "more-preferred monocotyledonous codon." That is, for purposes of the present invention the average monocotyledonous codons include GGT, GAT, GCT, AAT, ATT, ACG, TTT, CAT, CCG, CCA, GCG and CCC.

"More-preferred monocotyledonous codons" refers to the one or two most abundantly utilized monocotyledonous codons for each individual amino acid appearing in monocotyledonous plant genes as set forth in Table I below.

TABLE 1

| Amino Acid | Preferred Codon(s) |
|---|---|
| Gly | GGC |
| Glu | GAG |
| Asp | GAC |
| Val | GTG, GTC |
| Ala | GCC |
| Arg | AGG, CGC |
| Ser | AGC, TCC |
| Lys | AAG |
| Asn | AAC |
| Met | ATG |
| Ile | ATC |
| Thr | ACC |
| Trp | TGG |
| Cys | TGC |
| Tyr | TAC |
| Leu | CTG, CTC |
| Phe | TTC |
| Pro | CCC |
| Gln | CAG |
| His | CAC |
| End | TAG, TGA |

The determination of which codons are the more preferred monocotyledonous codons is done by compiling a list of mostly single copy monocotyledonous genes, where redundant members of multigene families have been removed. Codon analysis of the resulting sequences identifies the codons used most frequently in these genes. The monocot codon frequencies for each amino acid as determined by such an analysis is shown in FIG. 1 and is consistent with reported codon frequency determinations such as in Table 4 of E. E. Murray, et al. "Codon Usage in Plant Genes" NAR 17:477–498 (1989).

It has been discovered that a nucleotide sequence capable of enhanced expression in monocots can be obtained by reducing the frequency of usage of the rare and semi-rare monocotyledonous codons and preferentially utilizing the more-preferred monocotyledonous codons found in monocot plant genes. Therefore, the present invention provides a method for modifying a DNA sequence encoding a polypeptide to enhance accumulation of the polypeptide when expressed in a monocotyledonous plant. In another aspect, the present invention provides novel synthetic DNA sequences, encoding a polypeptide or protein that is not native to a monocotyledonous plant, that is expressed at greater levels in the plant than the native DNA sequence if expressed in the plant.

The invention will primarily be described with respect to the preparation of synthetic DNA sequences (also referred to as "nucleotide sequences, structural coding sequences or genes") which encode the crystal protein toxin of Bacillus thuringiensis (B.t.), but it should be understood that the method of the present invention is applicable to any DNA coding sequence which encodes a protein which is not natively expressed in a monocotyledonous plant that one desires to have expressed in the monocotyledonous plant.

DNA sequences modified by the method of the present invention are effectively expressed at a greater level in monocotyledonous plants than the corresponding non-modified DNA sequence. In accordance with the present invention, DNA sequences are modified to reduce the abundance of rare and semi-rare monocotyledonous codons in the sequence by substituting them with a more-preferred monocotyledonous codon. If the codon in the native sequence is neither rare, semi-rare nor a more-preferred codon, it is generally not changed. This results in a modified DNA sequence that has a significantly lower abundance of rare and semi-rare monocotyledonous codons and a greater abundance of the more-preferred monocotyledonous codons. In addition, the DNA sequence is further modified to reduce the frequency of CG dinucleotide pairs in the modified sequence. Preferably, the frequency of CG dinucleotides is reduced to a frequency of less than about 8% in the final modified sequence. The DNA sequence is also modified to reduce the occurrence of putative polyadenylation sites, intron splice sites and potential mRNA instability sites. As a result of the modifications, the modified DNA sequence will typically contain an abundance of between about 65%–90% of the more-preferred codons.

In order to construct a modified DNA sequence in accordance with the method of the present invention, the amino acid sequence of the desired protein must be determined and back-translated into all the available codon choices for each amino acid. It should be understood that an existing DNA sequence can be used as the starting material and modified by standard mutagenesis methods which are known to those skilled in the art or a synthetic DNA sequence having the desired codons can be produced by known oligonucleotide synthesis methods. For the purpose of brevity and clarity, the invention will be described in terms of a mutagenesis protocol. The amino acid sequence of the protein can be analyzed using commercially available computer software such as the BACKTRANSLATE® program of the GCG Sequence Analysis software Package.

Because most coding sequences of proteins of interest are of a substantial length, generally between 200–3500 nucleotides in length, the DNA sequence that encodes the protein is generally too large to facilitate mutagenesis or complete synthesis in one step. Therefore, it will typically be necessary to break the DNA sequence into smaller fragments of between about 300 bp to 1500 bp in length. To do this and to facilitate subsequent reassembly operations, desired restriction sites in the sequence are identified. The restriction site sequences will, therefore, determine the codon usage at those sites.

The sequence of the native DNA sequence is then compared to the frequency of codon usage for monocotyledonous plants as shown in FIG. 1. Those codons present in the native DNA sequence that are identified as being "rare monocotyledonous codons" are changed to the "more preferred monocotyledonous codon" such that the percentage of rare monocotyledonous codons in the modified DNA sequence is greater than about 0.1% and less than about 0.5% of the total codons in the resulting modified DNA sequence. Semi-rare monocotyledonous codons identified in the native DNA sequence are changed to the more-preferred monocotyledonous codon such that the percentage of semi-rare monocotyledonous codons is greater than about 2.5% and less than about 10% of the total codons in the resulting modified DNA sequence and, preferably less than about 5% of the total codons in the resulting modified DNA sequence. Codons identified in the native DNA sequence that are "average monocotyledonous codons" are not changed.

After the rare and semi-rare monocotyledonous codons have been changed to the more preferred monocotyledonous codon as described above, the DNA sequence is further analyzed to determine the frequency of occurrence of the dinucleotide 5'-CG-3'. This CG dinucleotide is a known DNA methylation site and it has been observed that methylated DNA sequences are often poorly expressed or not expressed at all. Therefore, if the codon changes as described above have introduced a significant number of CG dinucleotide pairs into the modified DNA sequence, the frequency of appearance of 5'-CG-3' dinucleotide pairs is reduced such that the modified DNA sequence has less than about 8% CG dinucleotide pairs, and preferably less than about 7.5% CG dinucleotides pairs. It is understood that any changes to the DNA sequence always preserve the amino acid sequence of the native protein.

The C+G composition of the modified DNA sequence is also important to the overall effect of the expression of the modified DNA sequence in a monocotyledonous plant. Preferably, the modified DNA sequence prepared by the method of this invention has a G+C composition greater than about 50%, and preferably greater than about 55%.

The modified DNA sequence is then analyzed for the presence of any destabilizing ATTTA sequences, putative polyadenylation signals or intron splice sites. If any such sequences are present, they are preferably removed. For purposes of the present invention, putative polyadenylation signals include, but are not necessarily limited to, AATAAA, AATAAT, AACCAA, ATATAA, AATCAA, ATACTA, ATAAA, ATGAAA, AAGCAT, ATTAAT, ATACAT, AAAATA, ATTAAA, AATTAA, AATACA and CATAAA. For purposes of the present invention, intron splice sites include, but are not necessarily limited to WGGTAA (5' intron splice site) and TRYAG (3' intron splice site), where W=A or T, R=A or G, and Y=C or T. When any of the ATTTA, putative polyadenylation signals or intron splice sites are changed, they are preferably replaced with one of the more preferred monocotyledonous codons or one of the average monocotyledonous codons. In essence, after the desired codon changes have been made to the native DNA sequence to produce the modified DNA sequence, the modified DNA sequence is analyzed according to the method described in commonly assigned U.S. patent application Ser. No. 07/476,661 filed Feb. 12, 1990, U.S. patent application Ser. No. 07/315,355 filed Feb. 24, 1989, and EPO 385 962 published Sep. 5, 1990. It is to be understood that while all of the putative polyadenylation signals and intron splice sites are preferably removed from the modified DNA sequence, a modified DNA sequence according to the present invention may include one or more of such sequences and still be capable of providing enhanced expression in monocotyledonous plants.

The resulting DNA sequence prepared according to the above description, whether by modifying an existing native DNA sequence by mutagenesis or by the de novo chemical synthesis of a structural gene, is the preferred modified DNA sequence to be introduced into a monocotyledonous plant for enhanced expression and accumulation of the protein product in the plant.

In a further embodiment of the present invention, an additional analysis is performed on the modified DNA sequence to further enhance its likelihood to provide enhanced expression and accumulation of the protein product in monocotyledonous plants. A list of rare monocotyledonous 6 mer nucleotide sequences is compiled from the same list of mostly single copy monocot genes as previously described for the compilation of the frequency of usage of monocotyledonous codons. A 6mer is six consecutive nucleotides in a sequence and proceeds in a successive fashion along the entire DNA sequence. That is, each adjacent 6mer overlaps the previous 6mer's terminal 5 nucleotides. Thus, the total number of six-mers in a DNA sequence is five less than the number of nucleotides in the DNA sequence. The frequency of occurrence of strings of six-mers was calculated from the list of monocotyledonous genes and the most rare 284, 484, and 664 monocotyledonous six-mers identified. The list of these most rare monocotyledonous six-mers is provided in FIG. 2. The modified DNA sequence is then compared to the lists of the most rare 284, 484, and 664 monocotyledonous six-mers and if one of the rare six-mers appears in the modified DNA sequence, it is removed by changing at least one of the nucleotides in the 6mer, but the amino acid sequence remains intact. Preferably, any such 6mer found in the modified DNA sequence is altered to produce a more preferred codon in the location of the 6mer. Preferably, the total number of the rarest 284 monocotyledonous six-mers in the modified DNA sequence will be less than about 1% of the total six-mers possible in the sequence, and more preferably less than about 0.5%, the total number of the rarest 484 monocotyledonous six-mers in the modified DNA sequence will be less than about 2% of the total six-mers possible in the sequence, and more preferably less than about 1.0%, and the total number of the rarest 664 monocotyledonous six-mers in the modified DNA sequence will be less than about 5% of the total six-mers possible in the sequence, and more preferably less than about 2.5%. It has been found that the removal of these 6mer sequences in this manner is beneficial for increased expression of the DNA sequence in monocotyledonous plants.

The method of the present invention has applicability to any DNA sequence that is desired to be introduced into a monocotyledonous plant to provide any desired characteristic in the plant, such as herbicide tolerance, virus tolerance, insect tolerance, drought tolerance, or enhanced or improved phenotypic characteristics such as improved nutritional or processing characteristics. Of particular importance is the provision of insect tolerance to a monocotyledonous plant by the introduction of a novel gene encoding a crystal protein toxin from B.t. into the plant. Especially preferred are the insecticidal proteins of B.t. that are effective against insects of the order Lepidoptera and Coleoptera, such as the crystal protein toxins of B.t. var. kurstaki CryIA(b) and CryIA(c) and the CryIIB protein.

The modified DNA sequences of the present invention are expressed in a plant in an amount sufficient to achieve the desired phenotype in the plant. That is, if the modified DNA sequence is introduced into the monocotyledonous plant to confer herbicide tolerance, it is designed to be expressed in herbicide tolerant amounts. It is understood that the amount of expression of a particular protein in a plant to provide a desired phenotype to the plant may vary depending upon the species of plant, the desired phenotype, environmental factors, and the like and that the particular amount of expression is determined in the particular situation by routine analysis of varying amounts or levels of expression.

A preferred modified DNA sequence for the control of insects, particularly Lepidopteran type insects, is provided as SEQ ID NO:1 and is shown in FIG. 3. A preferred modified DNA sequence expressing an effective B.t. CryIIB protein is provided as SEQ ID NO:2 and is shown in FIG. 4.

As will be described in more detail in the Examples to follow, the preferred modified DNA sequences were constructed by mutagenesis which required the use of numerous oligonucleotides. Generally, the method of Kunkel, T. A., *Proc. Natl. Acad. Sci, USA* (1985), Vol 82, pp. 488–492, for oligonucleotide mutagenesis of single stranded DNA to introduce the desired sequence changes into the starting DNA sequence was used. The oligonucleotides were designed to introduce the desired codon changes into the starting DNA sequence. The preferred size for the oligonucleotides is around 40–50 bases, but fragments ranging from 17 to 81 bases have been utilized. In most situations, a minimum of 5 to 8 base pairs of homology to the template DNA on both ends of the synthesized fragment are maintained to insure proper hybridization of the primer to the template. Multiple rounds of mutagenesis were sometimes required to introduce all of the desired changes and to correct any unintended sequence changes as commonly occurs in mutagenesis. It is to be understood that extensive sequencing analysis using standard and routine methodology on both the intermediate and final DNA sequences is necessary to assure that the precise DNA sequence as desired is obtained.

The expression of a foreign DNA sequence in a monocotyledonous plant requires proper transcriptional initiation regulatory regions, i.e. a promoter sequence, an intron, and a polyadenylation site region recognized in monocotyledonous plants, all linked in a manner which permits the transcription of the coding sequence and subsequent processing in the nucleus. A DNA sequence containing all of the necessary elements to permit the transcription and ultimate expression of the coding sequence in the monocotyledonous plant is referred to as a "DNA construct." The details of construction of such a DNA construct is well known to those in the art and the preparation of vectors carrying such constructs is also well-known.

Numerous promoters are known or are found to cause transcription of RNA in plant cells and can be used in the DNA construct of the present invention. Examples of suitable promoters include the nopaline synthase (NOS) and octopine synthase (OCS) promoters, the light-inducible promoter from the small subunit of ribulose bis-phosphate carboxylase promoters, the CaMV 35S and 19S promoters, the full-length transcript promoter from Figwort mosaic virus, ubiquitin promoters, actin promoters, histone promoters, tubulin promoters, or the mannopine synthase promoter (MAS). The promoter may also be one that causes preferential expression in a particular tissue, such as leaves, stems, roots, or meristematic tissue, or the promoter may be inducible, such as by light, heat stress, water stress or chemical application or production by the plant. Exemplary green tissue-specific promoters include the maize phosphoenol pyruvate carboxylase (PEPC) promoter, small submit ribulose bis-carboxylase promoters (ssRUBISCO) and the chlorophyll a/b binding protein promoters. The promoter may also be a pith-specific promoter, such as the promoter isolated from a plant TrpA gene as described in International Publication No. W093/07278, published Apr. 15, 1993. Other plant promoters may be obtained preferably from plants or plant viruses and can be utilized so long as it is capable of causing sufficient expression in a monocotyledonous plant to result in the production of an effective amount of the desired protein. Any promoter used in the present invention may be modified, if desired, to alter their control characteristics. For example, the CaMV 35S or 19S promoters may be enhanced by the method described in Kay et al. *Science* (1987) Vol. 236, pp.1299–1302.

The DNA construct prepared for introduction into the monocotyledonous plant also preferably contains an intron sequence which is functional in monocotyledonous plants, preferably immediately 3' of the promoter region and immediately 5' to the structural coding sequence. It has been observed that the inclusion of such a DNA sequence in the monocotyledonous DNA construct enhances the expression of the protein product. Preferably, the intron derived from the first intron of the maize alcohol dehydrogenase gene (MzADH1) as described in Callis et al. *Genes and Devel.* (1987) Vol. 1, pp1183–1200, or the maize hsp70 intron (as described in PCT Publication No. WO93/19189) is used. The HSP70 intron can be synthesized using the polymerase chain reaction from a genomic clone containing a maize HSP70 gene (pMON9502) Rochester et al. (1986) *Embo J.*, 5:451–458.

The RNA produced by a DNA construct of the present invention also contains a 3' non-translated polyadenylation site region recognized in monocotyledonous plants. Various suitable 3' non-translated regions are known and can by obtained from vital RNA, suitable eukaryotic genes or from a synthetic gene sequence. Examples of suitable 3' regions are (a) the 3' transcribed, non-translated regions containing the polyadenylation signal of *Agrobacterium tumefaciens* (Ti) plasmid genes, such as the NOS gene, and (b) plant genes such as the soybean storage protein (7S) genes and the small subunit of the RuBP carboxylase (E9) gene.

The modified DNA sequence of the present invention may be linked to an appropriate amino-terminal chloroplast transit peptide or secretory signal sequence to transport the transcribed sequence to a desired location in the plant cell.

A DNA construct containing a structural coding sequence prepared in accordance with the method of the present invention can be inserted into the genome of a plant by any suitable method. Examples of suitable methods include *Agrobacterium tumefaciens* mediated transformation, direct gene transfer into protoplasts, microprojectile bombardment, injection into protoplasts, cultured cells and tissues or meristematic tissues, and electroporation. Preferably, the DNA construct is transferred to the monocot plant tissue through the use of the microprojectile bombardment process which is also referred to as "particle gun technology." In this method of transfer, the DNA construct is initially coated onto a suitable microprojectile and the microprojectile containing DNA is accelerated into the target tissue by a microprojectile gun device. The design of the accelerating device is not critical so long as it can produce a sufficient acceleration function. The accelerated microprojectiles impact upon the prepared target tissue to perform the gene transfer. The DNA construct used in a microprojectile bombardment method of DNA transfer is preferably prepared as a plasmid vector coated onto gold or tungsten microprojectiles. In this regard, the DNA construct will be associated with a selectable marker gene which allows transformed cells to grow in the presence of a metabolic inhibitor that slows the growth of non-transformed cells. This growth advantage of the transgenic cells permits them to be distinguished, over time, from the slower growing or non-growing cells. Preferred selectable marker genes for monocotyledonous plants include a mutant acetolactate synthase DNA sequence which confers tolerance to sulfonylurea herbicides such as chlorsulfuron, the NPTII gene which confers resistance to aminoglycosidic antibiotics such as kanamycin or G418, or a bar gene (DeBlock et al., 1987, EMBO J. 6:2513–2518; Thompson et al., 1987, EMBO J. 6:2519–2523) for resistance to phosphinothricin or bialaphos. Alternatively, or in conjunction with a selectable marker, a visual screenable marker such as the *E. coli* B-glucuronidase gene or a luciferase gene can be included in the DNA construct to facilitate identification and recovery of transformed cells.

Suitable plants for use in the practice of the present invention include the group of plants referred to as the monocotyledonous plants and include, but are not necessarily limited to, maize, rice and wheat.

The following examples are illustrative in nature and are provided to better elucidate the practice of the present invention and are not to be interpreted in a limiting sense. Those skilled in the art will recognize that various modifications, truncations, additions or deletions, etc. can be made to the methods and DNA sequences described herein without departing from the spirit and scope of the present invention.

EXAMPLE 1

This example is provided to illustrate the construction of a novel DNA sequence encoding the crystal toxin protein from *B. thuringiensis* var. kurstaki CryIA(b) according to the method of the present invention that exhibits enhanced accumulation of its protein product when expressed in maize.

As the starting DNA sequence to be modified in accordance with the method of the present invention, the synthetic CryIA(b)/CryIA(c) DNA sequence as described in European Patent Application Publication No. 0385962 was utilized. This DNA sequence encodes a fusion B.t. kurstaki protein with the insect specificity conferred by the amino-terminal CryIA(b) portion. This DNA has been modified to remove any ATTTA sites and any putative polyadenylation sites and intron splice sites. This sequence is identified as SEQ ID NO:3 and is shown in FIG. 5.

The amino acid sequence of this B.t. sequence was known and all of the available codon choices were determined by analyzing the amino acid sequence using the BACK-TRANSLATE® program of the GCG Sequence Analysis Software Program. Because the B.t. gene is rather large (3569 bp in length) the mutagenesis process was conducted on a plurality of individual, smaller fragments of the starting DNA sequence as will be described below. The codon usage of the starting DNA sequence was then compared to the monocotyledonous codon frequency table as shown in FIG. 1 to determine which codons in the starting DNA sequence are rare or semi-rare monocotyledonous codons and are to be replaced with a more-preferred monocotyledonous codon. While keeping in mind the necessary restriction sites to facilitate religation of the DNA sequence after mutagenesis is complete, the modified DNA sequence design was determined. The modified DNA sequence design was then analyzed for any nucleotide strings of ATTTA or putative polyadenylation sites or intron splice sites. The modified DNA sequence design was then further modified to remove substantially all of such nucleotide strings, although one string of TTTTT, TRYAG, ATTTA, and AAGCAT remained in the design. The modified DNA sequence design was then analyzed for the occurrence of the dinucleotide 5'-CG-3' and, when possible, the modified DNA sequence was designed to remove such dinucleotide pairs, although all of such dinucleotide pairs were not removed. The resulting design is the preferred monocotyledonous CryIA(b) DNA sequence design and this sequence was compared to the starting DNA sequence by a sequence alignment program (Bestfit program of the GCG Sequence Analysis Software Package) to determine the number of mutagenesis primers needed to convert the starting DNA sequence into the modified DNA sequence.

The oligonucleotide mutagenesis primers were synthesized and purified by GENOSYS and the mutagenesis was carried out with the Bio-Rad Muta-Gene Enzyme Pack as described in the manufacturer's instruction manual. Following the mutagenesis reaction, a 10–30 µl aliquot of the ligation mix was transformed into JM101 cells and selected on LBr Cb50. Individual transformed colonies were picked into 96-well microtiter plates containing 150 µl 2XYT Cb50. After overnight growth at 37° C., the cultures were replicated onto S&S Nytran filters on 2XYT-Cb50 plates and allowed to grow overnight at 37° C. The filters were treated with denaturing solution (1.5M NaCl, 0.5M NaOH) for 5 minutes, neutralizing solution (3M NaOAc,pH5.0) for 5 minutes, air dried for 30 minutes, then baked for 1 hour at 80° C.

The desired mutants were identified by differential primer melt-off at 65° C. Mutagenesis oligonucleotides were end-labelled with either $P^{32}$ or DIG-ddUTP. When $P^{32}$ oligonucleotides were used, hybridizations were done overnight at 42° C. in 50% formamide, 3× SSPE, 5× Denhardt's, 0.1%–20% SDS and 100 ug/ml tRNA. Filters were washed in 0.2× SSC, 0.1% SDS for 20 minutes at 65° C. The filters were exposed to X-ray film for 1 hour. Colonies that contained the mutagenesis oligonucleotide retained the probe and gave a dark spot on the X-ray film. Parental colonies not subjected to mutagenesis were included in each screen as negative controls. For non-radioactive probes, the Genius DIG Oligonucleotide 3'-end labelling kit was used (Boehringer-Mannheim Biochemical, Indianapolis, Ind.) as per the manufacturer's instructions. Hybridization conditions were 50% formamide, 5× SSPE, 2% blocking solution, 0.1% N-laurylsarcosine, 0.02% SDS, and 100 µg/ml tRNA. Temperatures for hybridization and filter washes were as previously stated for the radioactive method. Lumi-Phos 530 (Boehringer Mannheim) was used for detection of hybrids, following exposures of 1 hour to X-ray film. DNA from the positive colonies was sequenced to confirm the desired nucleotide sequences. If further changes were needed, a new round of mutagenesis using new oligonucleotides and the above described procedures were carried out.

Plasmids were transformed into the *E. coli* dut-, ung-, BW313 or CJ236 for use as templates for mutagenesis. Fifteen mls of 2XYT media containing 50 µg/ml carbenicillin was inoculated with 300 µl of overnight culture containing one of the plasmids. The culture was grown to an OD of 0.3 and 15 µl of a stock of M13K07 helper phage was added. The shaking culture was harvested after 5 hours. Centrifugation at 10K for 15 minutes removed the bacteria and cell debris. The supernatant was passed through a 45 micron filter and 3.6 ml of 20% PEG/2.5M NaCl was added. The sample was mixed thoroughly and stored on ice for 30 minutes. The supernatant was centrifuged at 11K for 15 minutes. The phage pellet was resuspended in 400 µl Tris-EDTA, pH8.0 (TE buffer) and extracted once with chloroform, twice with phenol:chloroform:isoamyl. Forty µl of 7.5M NH$_4$OAc was added, then 1 ml ethanol. The DNA pellet was resuspended in 100 µl TE.

The method employed in the construction of the modified CryIA(b) DNA sequence is illustrated in FIG. 6. The starting clones containing the starting CryIA(b)/CryIA(c) DNA sequence included pMON10922, which was derived from pMON19433 and is shown in FIG. 7, by replacement of the GUS coding region of pMON19433 with the NcoI-EcoRI restriction fragment from pMON10914, which is shown in FIG. 8 and which contains a pUC plasmid with a CaMV 35S promoter/NptII/NOS 3' cassette and an ECaMV 35S promoter(enhanced CaMV 35S promoter according to the method of Kay et al.)/Adh1 intron/(DNA sequence B. t. k. CryIA(b)/CryIA(c))/NOS 3' cassette, the only sequences used from pMON10914 are between the BglII site (nucleotide #1) at the 5' end of the CryIA(b)/CryIA(c) DNA sequence and the EcoRI site (nucleotide #3569) at the 3' end of the sequence; pMON19470 which consists of the ECaMV 35S promoter, the hsp70 intron and NOS 3' polyA region in a pUC vector containing a NPTII selectable marker; and pMON 19689 which is derived from pMON 10922, the 3' region of the CryIA(b)/CryIA(c) B.t. gene in pMON10922 was excised using XhoI (nucleotide #1839) and EcoRI (nucleotide #3569) and replaced with an oligonucleotide pair having the sequence

5'-TCGAGTGATTCGAATGAG-3'       SEQ ID NO:4, and

5'-AATTCTCATTCGAATCAC-3'       SEQ ID NO:5, which creates XhoI and EcoRI cohesive ends when annealed that were ligated into pMON10922 to form pMON19689, which therefore contains a truncated CryIA(b) DNA sequence.

The five fragments of the starting CryIA(b)/CryIA(c) sequence from pMON10914 used for mutagenesis consisted of the following: pMON15740 which contained the 674 bp fragment from pMON10914 from the BglII to XbaI (nucleotide #675) restriction site cloned into the BamHI and XbaI sites of Bluescript SK+; pMON15741 which contains the sequence from the XbaI site to the SacI site (nucleotide #1354) cloned as a 679 bp XbaI-SacI fragment into the corresponding sites of Bluescript Sk+; pMON15742 which contains nucleotides between #1354-#1839 as a 485 bp SacI/XhoI fragment into the corresponding sites of Bluescript SK+; pMon 10928 which was derived from pMON10922 by excising the PvuII (nucleotide #2969) to EcoRI fragment and inserting it into the EcoRV to EcoRI site of Bluescript SK+; and pMON10927 which was derived from pMON10922 by excising the XhoI to PvuII fragment and inserting it into the XhoI to EcoRV site of pBS SK+.

The desired sequence changes were made to the section of the starting DNA sequence in pMON15741 by the use of oligonucleotide primers BTK15, BTK16, BTK17a and 17b (sequentially) and BTK18–BTK29 as shown in Table 2 below.

TABLE 2

| OLIGO # | SEQUENCE | ID NO: |
|---|---|---|
| BTK15 | TCTAGAGACT GGATTCGCTA CAACCAGTTC AGGCGCGAGC TGACCCTCAC CGTCCTGGAC ATT | SEQ ID NO: 6 |
| BTK16 | ATTGTGTCCC TCTTCCCGAA CTACGACTCC CGCACCTACC C | SEQ ID NO: 7 |
| BTK17a | ACCTACCCGA TCCGCACCGT GTCCCAACTG ACCCGCGAAA TCT | SEQ ID NO: 8 |
| BTK17b | AAATCTACAC CAACCCCGTC CTGGAGAACT TC | SEQ ID NO: 9 |
| BTK18 | AGCTTCAGGG GCAGCGCCCA GGGCATCGAG GGCTCCATC | SEQ ID NO: 10 |
| BTK19 | GCCCACACCT GATGGACATC | SEQ ID NO: 11 |

TABLE 2-continued

| OLIGO # | SEQUENCE | ID NO: |
|---|---|---|
| | CTCAACAGCA TCACTATCTA C | |
| BTK20 | TACACCGATG CCCACCGCGG CGAGTACTAC TGGTCCGGCC ACCAGATC | SEQ ID NO: 12 |
| BTK21 | ATGGGCCTCCC CGGTCGGCTT CAGCGGCCCC GAGTT | SEQ ID NO: 13 |
| BTK22 | CCTCTCTACG GCACGATGGG CAACGCCGC | SEQ ID NO: 14 |
| BTK23 | CAACAACGCA TCGTCGCTCA GCTGGGCCAG GGTGTCTACA G | SEQ ID NO: 15 |
| BTK24 | GCGTCTACCG CACCCTGAGC TCCACCCTGT ACCGCAGGCC CTTCAACATC GGTATC | SEQ ID NO: 16 |
| BTK25 | AACCAGCAGC TGTCCGTCCT GGATGGCACT GAGTTCGC | SEQ ID NO: 17 |
| BTK26 | TTCGCCTACG GCACCTCCTC CAACCTGCCC TCCGCTGTCT ACCGCAAGAG CGG | SEQ ID NO: 18 |
| BTK27 | AAGAGCGGCA CGGTGGATTC CCTGGACGAG ATCCCACC | SEQ ID NO: 19 |
| BTK28 | AATGTGCCCC CCAGGCAGGG TTTTTCCCAC AGGCTCAGCC ACGT | SEQ ID NO: 20 |
| BTK29 | ATGTTCCGCT CCGGCTTCAG CAACTCGTCC GTGAGC | SEQ ID NO: 21 |

Plasmids with the desired changes were identified by colony hybridization with the mutagenesis oligonucleotides at temperatures that prevent hybridization with the original template, but allow hybridization with the plasmids that had incorporated the desired target sequence changes. In some cases unexpected sequence alterations were found. These were corrected by the use of oligonucleotides BTK44–BTK49 as shown in Table 3 below.

TABLE 3

| OLIGO # | SEQUENCE | ID. NO: |
|---|---|---|
| BTK44 | GGGCAGCGCC CAGGGCATCG AGGGCTCCAT CAG | SEQ ID NO: 22 |
| BTK45 | TGCCCACCGC GGCGAGTAC | SEQ ID NO: 23 |
| BTK46 | CCGGTCGGCT TCAGCGGCCC CGAGTTTAC | SEQ ID NO: 24 |
| BTK47 | GGCCAGGGCG TCTACCGCAC CCTGAGCTCC ACCCTGTACC GCAGGCCCTT CAACATCGGT ATC | SEQ ID NO: 25 |
| BTK48 | CTGTCCGTCC TGGATGGCAC TGAGTTCGC | SEQ ID NO: 26 |
| BTK49 | TCAGCAACTC GTCCGTGAGC | SEQ ID NO: 27 |

The final DNA sequence derived from pMON15741 was introduced into pMON15753 and contains the XbaI-SacI restriction fragment carrying nucleotides #669–1348 of the modified monocotyledonous CryIA(b) DNA sequence.

The desired sequence changes were made to the section of the starting DNA sequence in pMON15742 by the use of oligonucleotide primers BTK30–BTK41 as shown in Table 4 below

TABLE 4

| OLIGO # | SEQUENCE | ID NO: |
|---|---|---|
| BTK30 | ATGTTCTCCT GGATTCATCG CAGCGCGGAG TTCAAC | SEQ ID NO: 28 |
| BTK31 | TCATTCCGTC CTCCCAAATC ACCCAAATCC CCCTCACCAA GTC | SEQ ID NO: 29 |
| BTK32 | ACCAAGTCCA CCAACCTGGG CAGCGGCACC TCCGTGGTGA | SEQ ID NO: 30 |

TABLE 4-continued

| OLIGO # | SEQUENCE | ID NO: |
|---|---|---|
| | AGGGCCCAGG CTT | |
| BTK33 | GGCTTCACGG GCGGCGACAT CCTGCGCAGG ACCTCCCCGG GCCAGATCAG CACCCT | SEQ ID NO: 31 |
| BTK34 | GCACCCTCCG CGTCAACATC ACCGCTCCCC TGTCCCAGAG GTAC GTACCGCGTC AGGAT | SEQ ID NO: 32 |
| BTK35 | AGGATTCGCT ACGCTAGCAC CACCAACCTG CAATTC | SEQ ID NO: 33 |
| BTK36 | ATCGACGGCA GGCCGATCAA TCAG | SEQ ID NO: 34 |
| BTK37 | TTCTCCGCCA CCATGTCCAG CGGCAGCAAC CTCCAATCCG G | SEQ ID NO: 35 |
| BTK38 | GCAGCTTCCG CACCGTGGGT TTCACCACCC CCTTCAACTT C | SEQ ID NO: 36 |
| BTK39 | AACTTCTCCA ACGGCTCCAG CGTTTTCACC CTGAGCGCTC A | SEQ ID NO: 37 |
| BTK40 | CTGAGCGCCC ACGTGTTCAA TTCCGGCAAT GAGGTGTACA TTGACCGCAT TGAGTT | SEQ ID NO: 38 |
| BTK41 | ATTGAGTTCG TGCCAGCCGA GGTCACCTTC GAAGGGGGGC C | SEQ ID NO: 39 |

Plasmids with the desired changes were identified by colony hybridization with the mutagenesis oligonucleotides at temperatures that prevent hybridization with the original template, but allow hybridization with the plasmids that had incorporated the desired target sequence changes. In some cases unexpected sequence alterations were found. These were corrected by the use of oligonucleotides BTK42–BTK43 as shown in Table 5 below.

TABLE 5

| OLIGO # | SEQUENCE | ID NO: |
|---|---|---|
| BTK42 | TGAAGGGCCC AGGCTTCACG GGCGGCGACA TCCTGCGCAG GACCTC | SEQ ID NO: 40 |
| BTK43 | CTAGCACCAC CAACCTGCAA TTCCACACCT CCATC | SEQ ID NO: 41 |

The final DNA sequence derived from pMON15742 was introduced into pMON15754 and contains the SacI-BstBI restriction fragment carrying nucleotides #1348–1833 of the modified monocotyledonous CryIA(b) DNA sequence.

The desired sequence changes were made to the section of the starting DNA sequence in pMON15740 by the use of oligonucleotide primers BTK0–BTK14 as shown in Table 6 below.

| OLIGO # | SEQUENCE | ID NO: |
|---|---|---|
| BTK00 | GGGGATCCAC CATGGACAAC | SEQ ID NO: 42 |
| BTK01 | ATCAACGAGT GCATCCCGTA CAACTGCCTC AGCAACCCTG AGGTCGAGGT ACTTGG | SEQ ID NO: 43 |
| BTK02 | GAGGTCGAGG TGCTCGGCGG | SEQ ID NO: 44 |

| OLIGO # | SEQUENCE | ID NO: |
|---|---|---|
| | TGAGCGCATC GAGACCGGTT ACACCCCCAT CG | |
| BTK03 | ACATCTCCCT CTCCCTCACG CAGTTCCTGC TCAG | SEQ ID NO: 45 |
| BTK04 | GTGCCAGGCG CTGGCTTCGT CCTGGGCCTC GTGGACATCA TC | SEQ ID NO: 46 |
| BTK05 | ATCTGGGGCA TCTTTGGCCC CTCCCAGTGG GACGCCTTCC TGGT | SEQ ID NO: 47 |
| BTK06 | GTGCAAATCG AGCAGCTCAT CAACCAGAGG ATCGAGGAGT TCGC | SEQ ID NO: 48 |
| BTK07 | AGGCCATCAG CCGCCTGGAG GGCCTCAGCA ACCTCTACCA AATCTACGCT GAGAGCTT | SEQ ID NO: 49 |
| BTK0B | AGAGCTTCCG CGAGTGGGAG GCCGACCCCA CTAACCC | SEQ ID NO: 50 |
| BTK09 | CGCGAGGAGA TGCGCATCCA GTTCAACGAC | SEQ ID NO: 51 |
| BTK10 | ACAGCGCCCT GACCACCGCC ATCCCACTCT TCGCCGTCCA GAAC | SEQ ID NO: 52 |
| BTK11 | TACCAAGTCC CGCTCCTGTC CGTGTACGTC CAGGCCGCCA ACCTGCACCT CAG | SEQ ID NO: 53 |
| BTK12 | AGCGTGCTGA GGGACGTCAG CGTGTTTGGC CAGAGGTGGG GCTTCGACGC CGCCACCATC AA | SEQ ID NO: 54 |
| BTK13 | ACCATCAACA GCCGCTACAA CGACCTCACC AGGCTGATCG GCAACTACAC | SEQ ID NO: 55 |
| BTK14 | CACGCTGTCC GCTGGTACAA CACTGGCCTG GAGCGCGTCT GGGGCCCTGA TTC | SEQ ID NO: 56 |

Plasmids with the desired changes were identified by colony hybridization with the mutagenesis oligonucleotides at temperatures that prevent hybridization with the original template, but allow hybridization with the plasmids that had incorporated the desired target sequence changes. In some cases unexpected sequence alterations were found. These were corrected by the use of oligonucleotides BTK50–BTK53 as shown in Table 7 below.

TABLE 7

| OLIGO # | SEQUENCE | ID NO: |
|---|---|---|
| BTK50 | GGCGCTGGCT TCGTCCT | SEQ ID NO: 57 |
| BTK51 | CAAATCTACG CTGAGAGCTT | SEQ ID NO: 58 |
| BTK52 | TAACCCAGCT CTCCGCGAGGAG | SEQ ID NO: 59 |
| BTK53 | CTTCGACGCC GCCACCAT | SEQ ID NO: 60 |

The final DNA sequence derived from pMON15740 was introduced into pMON15755 and contains the NcoI-XbaI restriction fragment carrying nucleotides #1–669 of the modified monocotyledonous CryIA(b) DNA sequence.

The desired sequence changes were made to the section of the starting DNA sequence in pMON10927 by the use of oligonucleotide primers BTK50D–BTK53D and BTK54–BTK61, and BTK63—BTK75 as shown in Table 8 below.

TABLE 8

| OLIGO # | SEQUENCE | ID NO: |
|---|---|---|
| BTK50D | GGGCCCCCCT TCGAAGCCGA GTACGACCTG GAGAGAGC | SEQ ID NO: 61 |
| BTK51D | AAGGCTGTCA ATGAGCTCTT CACGTCCAGC AATCAG | SEQ ID NO: 62 |
| BTK52D | CAATCAGATC GGCCTGAAGA | SEQ ID NO: 63 |

TABLE 8-continued

| OLIGO # | SEQUENCE | ID NO: |
|---|---|---|
| BTK53D | CCGACGTCAC TGACTA ACTGACTACC ACATCGACCA AGTCTCCAAC CTCGTGGAGT GCCTCTCCGA TGAGT | SEQ ID NO: 64 |
| BTK54 | ACGAGAAGAA GGAGCTGTCC GAGAAGGTGA AGCATGCCAA GCG | SEQ ID NO: 65 |
| BTK55 | GGAATCTCCT CCAGGACCCC AATTTCCGCG GCATCAACA | SEQ ID NO: 66 |
| BTK56 | CAGGCAGCTC GACCGCGGCT GGCGCGGCAG CACCG | SEQ ID NO: 67 |
| BTK57 | AGCACCGACA TCACGATCCA GGGCGGCGAC GA | SEQ ID NO: 68 |
| BTK58 | AACTACGTGA CTCTCCTGGG CACTTTCGA | SEQ ID NO: 69 |
| BTK59 | GAGTCCAAGC TCAAGGCTTA CACTCGCTAC CAGCTCCGCG GCTACAT | SEQ ID NO: 70 |
| BTK60 | CAAGACCTCG AGATTTACCT GATCCGCTAC AACGCCAAGC A | SEQ ID NO: 71 |
| BTK61 | GAGACCGTCA ACGTGCCCGG TACTGG | SEQ ID NO: 72 |
| BTK62 | CTCTGGCCGC TGAGCGCCCC CAGCCCGATC GGCAAGTGTG | SEQ ID NO: 73 |
| BTK63 | CCCACCACAG CCACCACTTC TC | SEQ ID NO: 74 |
| BTK64 | GATGTGGGCT GCACCGACCT GAACGAGGAC CT | SEQ ID NO: 75 |
| BTK65 | AAGACCCAGG ACGGCCACGA GCGCCTGGGC AACCT | SEQ ID NO: 76 |
| BTK66 | GGCAACCTGG AGTTCCTCGA GGGCAGGGCC CCCCTGGTCG GT | SEQ ID NO: 77 |
| BTK67 | GTCGGTGAGG CTCTGGCCAG GGTCAAGAGG GCTGAGAAGA A | SEQ ID NO: 78 |
| BTK68 | AGGGACAAGC GCGAGAAGCT CGAGTGGGAG ACCAACATCG T | SEQ ID NO: 79 |
| BTK69 | GAGGCCAAGG AGAGCGTCGA CGCCCTGTTC GTG | SEQ ID NO: 80 |
| BTK70 | AACTCCCAGT ACGACCGCCT GCAGGCCGAC AC | SEQ ID NO: 81 |
| BTK71 | ATCCACGCTGCCGACAAGAG GGTGCACA | SEQ ID NO: 82 |
| BTK72 | GCATTCGCGA GGCCTACCTG CCTGAGCTGT CCGTG | SEQ ID NO: 83 |
| BTK73 | GCCATCTTTG AGGAGCTGGA GGGCCGCATC TTTAC | SEQ ID NO: 84 |
| BTK74 | CATTCTCCCT GTACGACGCC CGCAACGTGA TCAAGAA | SEQ ID NO: 85 |
| BTK75 | GGCCTCAGCT GGAATTCCTG | SEQ ID NO: 86 |

Plasmids with the desired changes were identified by colony hybridization with the mutagenesis oligonucleotides at temperatures that prevent hybridization with the original template, but allow hybridization with the plasmids that had incorporated the desired target sequence changes. In some cases unexpected sequence alterations were found. These were corrected by the use of oligonucleotides BTK91 and BTK94 as shown in Table 9 below.

TABLE 9

| OLIGO # | SEQUENCE | ID NO: |
|---|---|---|
| BTK91 | CAAGAGGGCT GAGAAGAAGT GGAGGGACAA G | SEQ ID NO: 87 |
| BTK94 | TACTGGTTCC CTCTGGCCGC TGAGCGCCCC CAGCCCGATC GGCAAGTGTG CCCACCACA | SEQ ID NO: 88 |

The final DNA sequence derived from pMON10927 was introduced into pMON10947 and contains the BstBI-PvuI restriction fragment carrying nucleotides #1833-2888 of the modified monocotyledonous CryIA(b) DNA sequence.

The desired sequence changes were made to the section of the starting DNA sequence in pMON10928 by the use of oligonucleotide primers BTK76–BTK90 as shown in Table 10 below.

TABLE 10

| OLIG # | SEQUENCE | ID NO: |
|---|---|---|
| BTK76 | ATAAGCTTCA GCTGCTGGAA CGTCAAGGGC CACGTGGACG TCGAGGAAC | SEQ ID NO: 89 |
| BTK77 | AGAACAACCA CCGCTCCGTC CTGGTCGTCC CAGAGTGGGA | SEQ ID NO: 90 |
| BTK78 | GAGTGGGAGG CTGAGGTCTC CCAAGA | SEQ ID NO: 91 |
| BTK79 | CAAGAGGTCC GCGTCTGCCC AGGCCGCGGC TACATTCTCA GGGTCACCGC TTA | SEQ ID NO: 92 |
| BTK80 | AAGGAGGGCT ACGGTGAGGGC TGTGTGACCA T | SEQ ID NO: 93 |
| BTK81 | AACTGCGTGG AGGAGGAGGT GTACCCAAAC AACAC | SEQ ID NO: 94 |
| BTK82 | GACTACACCG CCACCCAGGA GGAGTACGAG GGCACCTACA CT | SEQ ID NO: 95 |
| BTK83 | CCTACACTTC CAGGAACAGG GGCTACGATG GTGCCTACGA GAGCAACAGC AGCGTTCCTG | SEQ ID NO: 96 |
| BTK84 | CTGACTACGC TTCCGCCTAC GAGGAGAAGG CCTACAC | SEQ ID NO: 97 |

TABLE 10-continued

| OLIG # | SEQUENCE | ID NO: |
|---|---|---|
| BTK85 | CCTACACGGA TGGCCGCAGG GACAACCCTT G | SEQ ID NO: 98 |
| BTK86 | CTTGCGAGAG CAACCGCGGC TACGGCGACT ACAC | SEQ ID NO: 99 |
| BTK87 | GACTACACTC CCCTGCCCGC CGGCTACGTT ACCA | SEQ ID NO: 100 |
| BTK88 | AGGAGCTGGA GTACTTCCCG GAGACTGACA AGGTGTGGA | SEQ ID NO: 101 |
| BTK89 | TCGAGATCGG CGAGACCGAG GGCACCTTCA T | SEQ ID NO: 102 |
| BTK90 | GTGGAGCTGC TCCTGATGGA GGAGTAGAAT TCCTCTAAGC T | SEQ ID NQ: 103 |

Plasmids with the desired changes were identified by colony hybridization with the mutagenesis oligonucleotides at temperatures that prevent hybridization with the original template, but allow hybridization with the plasmids that had incorporated the desired target sequence changes. In one case an unexpected sequence alteration was found. This was corrected by the use of oligonucleotide BTK92 as shown in Table 11 below.

TABLE 11

| OLIGO # | SEQUENCE | ID NO: |
|---|---|---|
| BTK92 | CTGGTCGTCC CAGAGTGGGA GGCTGAGGTC TCCCAAGAGG TCCGCGTCTG CCCAGGCCG | SEQ ID NO: 104 |

The final DNA sequence derived from pMON10928 was introduced into pMON10944 and contains the PvuII-EcoRI restriction fragment carrying nucleotides #2888–3473 of the modified monocotyledonous CryIA(b) DNA sequence.

pMON15742 was subjected to oligonucleotide mutagenesis with oligonucleotide BTK41 (SEQ ID NO:38) to form pMON15767. The resulting B. t. k. CryIA DNA fragment of pMON15767 was excised with SacI and BstBI and inserted into the SacI and BstBI sites of pMON19689 to form pMON15768 which contains the NcoI-BstBI restriction fragment which contains nucleotides 7–1811 of the starting DNA sequence attached to nucleotides 1806–1833 of the modified DNA sequence.

Intermediate clones were prepared as follows: The SacI-BstBI fragment from pMON15754 was inserted into the SacI-BstBI sites of pMON19689 to form pMON15762 which contains nucleotides 7–1354 of the starting DNA sequence attached to nucleotides 1348–1833 of the modified DNA sequence; the XbaI to BstBI fragment of pMON19689 was excised and replaced with the XbaI to SacI fragment from pMON15753 and the SacI-BstBI fragment from pMON15762 resulting in pMON15765 which contains a truncated B.t. CryIA(b) DNA sequence where approximately the first third of the sequence from NcoI to XbaI of the starting DNA sequence is attached to XbaI-BstBI of the modified DNA sequence. Plasmid pMON15766 was prepared by excising the NcoI-XbaI fragment of pMON15765 and replaced by the NcoI-XbaI fragment from pMON15755 to yield pMON15766. pMON15766 thus encodes a truncated CryIA(b) sequence composed of nucleotides 1–1833 of the modified DNA sequence.

The final full length clones were prepared as follows: pMON10948 which encodes the full length CryIA(b) DNA sequence prepared in accordance with the method of this invention was made by inserting the BstBI to PvuII CryIA(b) fragment from pMON10947 and the PvuII-EcoRI fragment from pMON10944 into the BstBI-EcoRI site of pMON15766. The CryIA(b) B.t. DNA sequence of pMON10948 consists of the modified DNA sequence having nucleotides 1–3473; pMON10949, which encodes a full-length CryIA(b) DNA sequence where the first half of the gene consists of nucleotides 7–1811 of the starting DNA sequence attached to nucleotides 1806–3473 of the modified DNA sequence. pMON10949 was made by inserting the BstBI to EcoRI fragment from pMON10948 into the BstBI-EcoRI site of pMON15768. The sequence of the CryIA(b) DNA sequence in pMON10949 is identified as SEQ ID NO:105 and is shown in FIG. 9. pMON15722 was derived from pMON10948 by excising the entire CryIA(b) modified DNA sequence cassette, including the ECaMV promoter, hsp70 intron and NOS3' polyadenylation site region, as a NotI fragment and inserting it between the NotI sites of pMON19470 (this does not change any of the modified B. t. k. CryIA DNA sequence). pMON15774 was derived from pMON10948 by excising the entire CryIA(b) DNA sequence including the promoter, intron, CryIA(b) coding sequence, and NOS 3' polyadenylation site region as a NotI fragment and inserted between the NotI sites of pMON19470 (this does not change any of the B.t. DNA sequences).

The resulting modified CryIA(b) DNA sequence (SEQ ID NO:1) has a total abundance of 0.25% rare monocotyledonous codons and 3.8% semi-rare monocotyledonous codons. The total abundance of more preferred monocotyledonous codons is 86%. The CG dinucleotide frequency in the resulting modified DNA sequence was 7.5%. The modified CryIA(b) DNA sequence is compared to the wild-type bacterial CryIA(b) DNA sequence in FIG. 13.

EXAMPLE 2

This example illustrates the transient gene expression of the modified B. t. k. CryIA DNA sequence described in Example 1 and the CryIA(b)/CryIA(c) B.t. DNA sequence modified by the Fischoff et al. method in corn leaf protoplasts.

The level of expression of the modified CryIA(b) B.t. DNA sequence in pMON10948 and pMON15772 which contains the B. t. k. CryIA DNA sequence modified in accordance with the method of the present invention, the dicot/modified CryIA(b) B.t. DNA sequence in pMON10949 which has the 5' half of the DNA sequence modified in accordance with the method of Fischoff et al. and the 3' half modified in accordance with the method of the present invention, and the CryIA(b)/CryIA(c) DNA sequence modified by the Fischoff et al. method in pMON19493, were compared in a transient gene expression system in corn leaf protoplasts. The protoplasts were isolated from young corn seedlings. The DNA sequences were transferred into the protoplasts by electroporation and, after allowing time for gene expression, the electroporated samples were harvested and analyzed for gene expression. Samples were performed in duplicate and the ELISA values (performed in triplicate) were averaged for each experiment. The protein levels were measured by ELISA and the values indicated that 9-fold more CryIA(b) protein was produced from the modified B. t. k. CryIA DNA sequence in pMON10948 or pMON15772 than from pMON19493 containing the prior art CryIA(b)/CryIA(c) DNA sequence. The mixed B.t. DNA sequence in pMON10949 was expressed at 7 fold higher levels than pMON19493 indicating that most of the benefit of the modified B.t. DNA sequence of this invention is in the 3' portion of the CryIA(b) DNA sequence. This data is presented in Table 12.

TABLE 12

| Construct tested | Avg. Expt 1 (ng Btk/ml) | Avg. Expt 2 (ng Btk/ml) |
|---|---|---|
| 19493 | 13.6 | 8.3 |
| 10949 | 103 | 57 |
| 10948 | 138 | 66.4 |
| 15722 | nd | 72.7 |

EXAMPLE 3

This Example illustrates the expression of a modified B.t. DNA sequence modified by the method of the present invention in stably transformed corn cells.

Black Mexican Sweet (BMS) suspension cells were stably transformed using the microprojectile bombardment method and the chlorsulfuron EC9 selectable marker. Transgenic calli expressing the DNA sequence were initially identified by their insecticidal activity against tobacco hornworm larvae in a diet assay containing the calli. B.t. protein levels from individual insecticidal transgenic BMS calli were measured by ELISA from 48 calli expressing pMON15772 DNA and 45 calli expressing pMON19493. This comparison found that the average B.t. protein levels produced in pMON15772 calli was 6.5 fold higher than the average B.t. protein levels produced in pMON19493 calli. Western blot analysis confirmed the ELISA results and that the shorter processed forms of the proteins, predominantly the CryIA(b) portion, were in the extracts. These results demonstrate that the B. t. k. CryIA DNA sequence modified according to the method of the present invention functions better than the dicot CryIA(b)/CryIA(c) DNA sequence in stably transformed corn cells.

The ELISA assay used herein is a direct double antibody sandwich that utilizes a single polyclonal rabbit antibody against CryIA(b) as antigen (F137) for the capture and detection of the B. t. k. CryIA protein. Unconjugated antibody is used to coat 96 well polystyrene dishes. Alkaline phosphatase conjugated F137 antibody is added to the antibody coated dishes along with the test extracts or purified standard and allowed to incubate. The amount of B. t. k. CryIA protein present in the sample is directly proportional to the amount of alkaline phosphate-antibody bound. Color development with the p-nitrophenyl phosphate allows for quantitation of the CryIA(b) concentration in the samples using linear regression of the calibration curve prepared with the purified CryIA(b) protein standard.

Because the CryIA(b)/CryIA(c) protein differs from the CryIA(b) protein in the carboxyl terminus region, it needed to be confirmed that the ELISA measurements were accurately quantitating the CryIA(b)/CryIA(c) and CryIA(b) proteins produced from the full length synthetic DNA sequences. A trypsin treatment was used to produce identical amino terminal truncated CryIA(b) proteins in each extract. Bovine pancreatic trypsin (Calbiochem) was prepared as a 5 mg/ml solution in 50 mM sodium carbonate, pH8.5–9 and 3.5 µl of the trypsin solution was added per 100 µl tissue extract, mixed and incubated at 23° C. for 1.5 hours. The reaction was stopped by the addition of 2.5 µl of a 50 mM solution of PMSF in isopropanol, per 100 µl extract.

A Western blot of the trypsin treated and untreated samples demonstrated that adding trypsin did convert the CryIA(b)/CryIA(c) and CryIA(b) proteins into a truncated size identical to the amino terminal portion of trypsin treated bacterial CryIA(b). The abundance of the B.t. proteins of either the untreated or trypsin treated samples was comparable to those found by the ELISA measurements of the protoplast extracts. This confirms that the ELISA assays accurately measure the amount of B.t. protein present, regardless of whether it is CryIA(b)/CryIA(c) or CryIA(b). The Western blot independently confirmed that the CryIA(b) DNA sequence prepared in accordance with the method of the present invention and the mixed prior art/modified CryIA(b) DNA sequence expressed at considerably greater levels than the B.t. full length synthetic DNA sequence of the prior art in pMON19493.

Additionally, the Western blot revealed that in protoplast extracts a considerable portion of the B.t. protein, either CryIA(b)/CryIA(c) or CryIA(b), was present as shorter, processed form of the full-length B.t. protein. Similar processed B.t. protein forms are present in extracts from both transgenic callus and plant tissue. This further explains why the ELISA assay provides accurate results against both the CryIA(b)/CryIA(c) and CryIA(b) proteins from the full-length DNA sequences, as it is effectively measuring the same amino terminal portions of the proteins.

EXAMPLE 4

This Example illustrates the expression of pMON15772 and pMON19493 in transgenic corn plants.

A highly embryogenic, friable Type II callus culture is the preferred tissue for obtaining transgenic, whole corn plants. The age of the embryogenic culture can be from the initial callus formation on the immature embryos, approximately one week after embryo isolation, to older established cultures of 6 months to 2 years old, however, it is preferred to use younger cultures to enhance the potential for recovery of fertile transgenic plants. Type II cultures were initiated from immature HiII embryos on N6 2-100-25 medium containing 10 µM silver nitrate and solidified with 0.2% Phytagel. The most friable Type II calli were picked after about two weeks growth, and transferred onto fresh N6 2-100-25 medium containing 10 uM silver nitrate, in the center of the plate, in preparation for bombardment.

Four days after the calli were picked and transferred, the corn cell were bombarded 2 or 3 times with M10 tungsten particles coated with pMON15772 or pMON19493 mixed with pMON19574 as the selectable marker plasmid, using the particle preparation protocol described below. M10 particles at 100 mg/ml in 50% glycerol are sonicated to resuspend the particles. An aliquot of 12.5 µl is placed into a small microfuge tube and 2.5 µl of the desired DNA at 1 µg/l is added and mixed well by pipetting up and down rapidly several times. A freshly prepared CaCl$_2$/spermidine pre-mix is added in an amount of 17.5 µl and again mixed thoroughly. The particles are allowed to settle undisturbed for about 20 minutes and then 12.5 µl of the supernatant was removed. The particles are ready for use and are used in microprojectile bombardment within one hour of their preparation.

After bombardment, the cells were transferred to fresh N6 2-100-25 medium containing 10 µM silver nitrate for seven days without any selective pressure. The cells were then transferred to N6 1-0-25 media containing 3 mM glyphosate. Two weeks later, the cells were transferred to fresh selective media of the same composition. After a total of 6 or 7 weeks post-bombardment, glyphosate-tolerant calli could be observed growing on the selection media. Occasionally, the cell population would be transferred to fresh selective plates at this time to carry on the selection for 10–12 weeks total time. Glyphosate resistant calli were picked onto fresh N6 1-0-25 media containing 3 mM glyphosate for increasing the amount of callus tissue prior to initiating plant regeneration.

Plant regeneration was initiated by placing the transgenic callus tissue on MS 0.1 D media for two weeks. At two weeks, the tissue was transferred to N6 6% OD media for another two week period. The regenerating tissues are then transferred to MS 0 D media and transferred into lighted growth chambers. After another two weeks in the same media in larger containers, the young plants are hardened off, followed by transfer to the greenhouse where they were maintained in the same manner as normal corn plants. In most instances, the regeneration process was performed with 0.01 mM glyphosate in the regeneration media.

The corn plants were allowed to grow and the level of B. t. k. CryIA protein expressed in the leaves of the plant were measured by ELISA. As is commonly observed in transgenic plants, a large range of expression values were observed and, therefore, a large number of independently derived transgenic plants were examined. The B.t. levels in 44 pMON19493 plants and 86 pMON15722 plants were measured by ELISA assays of leaf material. Each line of plants were derived from embryogenic callus expressing the B.t. DNA sequence as determined by insecticidal activity against tobacco hornworm. Thus, the percentage of transformants that do not express the B.t. DNA sequence, as occurs in the transformation process, are not included in the data set. Western blots demonstrated that the majority of B.t. protein in the leaf extracts was processed to the predominantly CryIA(b) form of the protein, which has been shown to be recognized equivalently by the ELISA antibody assay. These results illustrate that the average level of B.t. expression with pMON15722 plants is at least 5 fold higher than the average level of B.t. expression from pMON19493 plants as shown in Table 13.

TABLE 13

| Gene | B. t. protein (% of total protein) | | | | | |
|---|---|---|---|---|---|---|
| | <0.001 | <0.005 | <0.025 | <0.05 | <0.1 | >0.1 |
| pMON19493 | 37 | 4 | 3 | 0 | 0 | 0 |
| pMON15722 | 25 | 43 | 5 | 4 | 3 | 6 |

This data is presented in graph form in FIG. 10.

EXAMPLE 5

This example illustrates the preparation of another form of a crystal toxin protein from B.t., namely the CryIIB DNA sequence (Widner et al., *J Bact.*, 171: 965-974), according to the method of the present invention and also utilizing the 6mer analysis of the DNA sequence to construct a modified DNA sequence that exhibits enhanced expression in a monocotyledonous plant.

The starting DNA sequence for this Example was the CryIIA synthetic DNA sequence identified by SEQ ID NO:106. The CryIIB synthetic DNA sequence was constructed from SEQ ID NO:106 by a new gene construction process. The CryIIA gene was used as a template for annealing oligonucleotides. These oligonucleotides fit precisely adjacent to each other such that DNA ligase could close the gap to form a covalent linkage. After the ligation reaction, the linked oligonucleotides were amplified by PCR and subcloned. Thus, this process is a form of oligonucleotide mutagenesis that ligates the oligonucleotides into one contiguous fragment of the desired new sequence. Because of the large size of the CryIIA gene, the process was carried out on five smaller fragments designated A, B, C, D and E. A representation of the steps by which the CryIIB synthetic DNA sequence of the present invention was prepared is presented in FIG. 11.

A double stranded plasmid containing the CryIIA synthetic DNA sequence (SEQ ID NO:106) in pBSKS+, referred to hereinafter as the P2syn DNA sequence, was digested and used as an annealing template for the different oligonucleotide combinations. For the A fragment, oligonucleotides A1 through A4, as shown in Table 14, were annealed to linearized pP2syn and ligated with T4 DNA ligase. The new strand of the contiguous oligonucleotides was amplified using primers AP5 and AP3, as shown in Table 14, under standard PCR conditions. The amplified double stranded fragment was digested with the restriction enzymes XbaI and BamHI and cloned into similarly digested pBSKS+ to form pMON19694.

TABLE 14

| OLIGO # | SEQUENCE | ID NO: |
|---|---|---|
| A1 | TCTAGAAGAT CTCCACCATG GACAACTCCG TCCTGAACTC TGGTCGCACC ACCATCT | SEQ ID NO: 107 |
| A2 | GCGACGCCTA CAACGTCGCG GCGCATGATC CATTCAGCTT CCAGCACAAG AGCCTCGACA CTGTTCAGAA | SEQ ID NO: 108 |
| A3 | GGAGTGGACG GAGTGGAAGA AGAACAACCA CAGCCTGTAC CTGGACCCCA TCGTCGGCAC GGTGGCCAGC TTCCT | SEQ ID NO: 109 |
| A4 | TCTCAAGAAG GTCGGCTCTC TCGTCGGGAA GCGCATCCTC TCGGAACTCC GCAACCTGAT CAGGATCC | SEQ ID NO: 110 |
| AP5 | CCATCTAGAA GATCTCCACC | SEQ ID NO: 111 |
| AP3 | TGGGGATCCT GATCAGGTTG | SEQ ID NO: 112 |

For the B fragment, oligonucleotides B1 through B6, were annealed to pP2syn and ligated with T4 DNA ligase. The new strand of the contiguous oligonucleotides was amplified using primers BP5 and BP3, as shown in Table 15, under standard PCR conditions. The amplified double stranded fragment was digested with the restriction enzymes BglII and PstI and cloned into similarly digested pMON19694 to form pMON19700.

TABLE 15

| OLIGO # | SEQUENCE | ID NO: |
|---|---|---|
| B1 | AGATCTTTCC ATCTGGCTCC ACCAACCTCA TGCAAGACAT CCTCAGGGAG ACCGAGAAGT TTCTCAACCA GCGCCTCAAC A | SEQ ID NO: 113 |
| B2 | CTGATACCCT TGCTCGCGTC AACGCTGAGC TGACGGGTCT GCAAGCAAAC GTGGAGGAGT TCAACCGCCA AGTGG | SEQ ID NO: 114 |
| B3 | ACAACTTCCT CAACCCCAAC CGCAATGCGG TGCCTCTGTC CATCA | SEQ ID NO: 115 |
| B4 | CTTCTTCCGT GAACACCATG CAACAACTGT TCCTCAACCG CTTGCCTCAG TTCCAGATGC AAGGC | SEQ ID NO: 116 |
| B5 | TACCAGCTGC TCCTGCTGCC ACTCTTTGCT CAGGCTGCCA ACCTGCACCT CTCCTTCATT CGTGACGTG | SEQ ID NO: 117 |
| B6 | ATCCTCAACG CTGACGAGTG GGGCATCTCT GCAG | SEQ ID NO: 118 |

TABLE 15-continued

| OLIGO # | SEQUENCE | ID NO: |
|---|---|---|
| BP5 | CCAAGATCTT TCCATCTGGC | SEQ ID NO: 119 |
| BP3 | GGTCTGCAGA GATGCCCCAC | SEQ ID NO: 120 |

For the C fragment, oligonucleotides C1 through C7, as shown in Table 16, were annealed to pP2syn and ligated with T4 DNA ligase. The new strand of the contiguous oligonucleotides was amplified using primers CP5 and CP3, as shown in Table 16, under standard PCR conditions. The amplified double stranded fragment was digested with the restriction enzymes PstI and XhoI and cloned into similarly digested pBSKS+ to form pMON19697.

TABLE 16

| OLIGO # | SEQUENCE | ID NO: |
|---|---|---|
| C1 | CTGCAGCCAC GCTGAGGACC TACCGCGACT ACCTGAAGAA CTACACCAGG GACTACTCCA ACTATTG | SEQ ID NO: 121 |
| C2 | CATCAACACC TACCAGTCGG CCTTCAAGGG CCTCAATACG AGGCTTCACG ACATGCTGGA GTTCAGGAC | SEQ ID NO: 122 |
| C3 | CTACATGTTC CTGAACGTGT TCGAGTACGT CAGCATCTGG TCGCTCTTCA AG | SEQ ID NO: 123 |
| C4 | TACCAGAGCC TGCTGGTGTC CAGCGGCGCC AACCTCTACG CCAGCGGCTC TGGTCCCCAA CAAACTCA | SEQ ID NO: 124 |
| C5 | GAGCTTCACC AGCCAGGACT GGCCATTCCT GTATTCGTTG TTCCAAGTCA A | SEQ ID NO: 125 |
| C6 | CTCCAACTAC GTCCTCAACG GCTTCTCTGG TGCTCGCCTC TCCAACACCT TCCCCAA | SEQ ID NO: 126 |
| C7 | CATTGTTGGC CTCCCCGGCT CCACCACAAC TCATGCTCTG CTTGCTGCCA GAGTGAACTA CTCCGGCGGC ATCTCGAG | SEQ ID NO: 127 |
| CP5 | CCACTGCAGC CACGCTGAGG ACC | SEQ ID NO: 128 |
| CP3 | GGTCTCGAGA TGCCGCCGGA | SEQ ID NO: 129 |

For the D fragment, oligonucleotides D1 through D7, as shown in Table 17, were annealed to pP2syn and ligated with T4 DNA ligase. The new strand of the contiguous oligonucleotides was amplified using primers DP5 and DP3, as shown in Table 17, under standard PCR conditions. The amplified double stranded fragment was digested with the restriction enzymes XhoI and KpnI and cloned into similarly digested pBSKS+ to form pMON19702.

TABLE 17

| OLIGO # | SEQUENCE | ID NO: |
|---|---|---|
| D1 | ATTGGTGCAT CGCCGTTCAA CCAGAACTTC AACTGCTCCA CCTTCCTGCC GCCGCTGCTC ACCCCGTTCG TGAGGT | SEQ ID NO: 130 |
| D2 | CCTGGCTCGA CAGCGGCTCC GACCGCGAGG GCGTGGCCAC CGTCACCAAC TGGCAAACC | SEQ ID NO: 131 |
| D3 | GAGTCCTTCG AGACCACCCT TGGCCTCCGG AGCGGCGCCT TCACGGCGCG TGGG | SEQ ID NO: 132 |
| D4 | AATTCTAACT ACTTCCCCGA | SEQ ID NO: 133 |

TABLE 17-continued

| OLIGO # | SEQUENCE | ID NO: |
|---|---|---|
| D5 | CTACTTCATC AGGAACATCT CTGG TGTTCCTCTC GTCGTCCGCA ACGAGGACCT CCGCCGTCCA CTGCACTACA ACGAGATCAG GAA | SEQ ID NO: 134 |
| D6 | CATCGCCTCT CCGTCCGGGA CGCCCGGAGG TGCAAGGGCG TACATGGTGA GCGTCCATAA C | SEQ ID NO: 135 |
| D7 | AGGAAGAACA ACATCCACGC TGTGCATGAG AACGGCTCCA TGAT | SEQ ID NO: 136 |
| DP5 | CCACTCGAGC GGCGACATTG GTGCATCGCC G | SEQ ID NO: 137 |

TABLE 17-continued

| OLIGO # | SEQUENCE | ID NO: |
|---|---|---|
| DP3 | GGTGGTACCT GATCATGGAG CCGTTCTCAT GCA | SEQ ID NO: 138 |

For the E fragment, oligonucleotides E1 through E8, as shown in Table 18, were annealed to pP2syn and ligated with T4 DNA ligase. The new strand of the contiguous oligonucleotides was amplified using primers EP5 and EP3, as shown in Table 18, under standard PCR conditions. The amplified double stranded fragment was digested with the restriction enzymes BamHI and KpnI and cloned into similarly digested pBSKS+ to form pMON19698.

TABLE 18

| OLIGO # | SEQUENCE | ID NO: |
|---|---|---|
| E1 | GGATCCACCT GGCGCCCAAT GATTACACCG GCTTCACCAT CTCTCCAATC CACGCCACCG AAGT | SEQ ID NO: 139 |
| E2 | GAACAACCAG ACACGCACCT TCATCTCCGA GAAGTTCGGC AACCAGGGCG ACTCCCTGAG GT | SEQ ID NO: 140 |
| E3 | TCGAGCAGAA CAACACCACC GCCAGGTACA CCCTGCGCGG CAACGGCAAC AGCTACAACC TGTACCTGCG CGTCAGCTCC A | SEQ ID NO: 141 |
| E4 | TTGGCAACTC CACCATCAGG GTCACCATCA ACGGGAGGGT GTACACAGCC ACCAATGTGA ACACGACGAC CAACAATG | SEQ ID NO: 142 |
| E5 | ATGGCGTCAA CGACAACGGC GCCCGCTTCA GCGACATCAA C | SEQ ID NO: 143 |
| E6 | ATTGGCAACG TGGTGGCCAG CAGCAACTCC GACGTCCCGC TGGACAT | SEQ ID NO: 144 |
| E7 | CAACGTGACC CTGAACTCTG GCACCCAGTT CGACCTCATG AA | SEQ ID NO: 145 |
| E8 | CATCATGCTG GTGCCAACTA ACATCTCGCC GCTGTACTGA TAGGAGCTCT GATCAGGTAC C | SEQ ID NO: 146 |
| EP5 | GGAGGATCCA CCTGGCGCCC A | SEQ ID NO: 147 |
| EP3 | GGTGGTACCT GATCAGAGCT | SEQ ID NO: 148 |

Some sequence errors occurred during the construction process. The repair oligonucleotides A5 and A6 were used to repair fragment A, and oligonucleotides B7–B10, C8–C10, D8–D10, and E9–E11, were used to repair fragments B–E, respectively, using the single stranded oligonucleotide mutagenesis described in Example 1. These oligonucleotides are shown in Table 19.

TABLE 19

| OLIGO # | SEQUENCE | ID NO: |
|---|---|---|
| A5 | CCACCATGGA CAACTCCGTC | SEQ ID NO: 149 |
| A6 | GGAAGAAGAA CAACCACAGC CTGTACCTGG ACCC | SEQ ID NO: 150 |
| B7 | CCACCAACCT CATGCAAGAC | SEQ ID NO: 151 |
| B8 | CTCAACCAGC GCCTCAACAC | SEQ ID NO: 152 |
| B9 | CCGCAATGCG GTGCCTCTGT CCATCACTTC TTCCGTG | SEQ ID NO: 153 |
| B10 | CGTGACGTGA TCCTCAACG | SEQ ID NO: 154 |
| C8 | GGACTGGCCA TTCCTGTAT | SEQ ID NO: 155 |
| C9 | CGCCAGCGGC TCTGGTCCC | SEQ ID NO: 156 |
| C10 | GAAGAACTAC ACCAGGGAC | SEQ ID NO: 157 |
| D8 | GCTCCGACCG CGAGGGCGTG | SEQ ID NO: 158 |
| D9 | CTCCGGAGCG GCGCCTTCAC GGCGCGTGGG AATTC | SEQ ID NO: 159 |
| D10 | CATCTCTGGT GTTCCTCTCG | SEQ ID NO: 160 |
| E9 | GCGGCAACGG CAACAGCTAC | SEQ ID NO: 161 |
| E10 | CTCCACCATC AGGGTCACCA TC | SEQ ID NO: 162 |
| E11 | GAACATCATG CTGGTGCC | SEQ ID NO: 163 | pMON19694 was then restricted at the PstI and XhoI sites in the pBSKS+ polylinker, removing a small oligonucleotide region. The insert from pMON19697 was excised with PstI and XhoI and ligated into the PstI and XhoI digested pMON19694 to form pMON19703. pMON19703 was digested with BclI and PstI, removing a small oligonucleotide region, and the BglII and PstI digested insert from pMON19700 was ligated into pMON19703 to form pMON19705. pMON19705 was digested with XhoI and KpnI and the XhoI to KpnI excised insert of pMON19702 was ligated into pMON19705 to form pMON19706. pMON19706 was digested with BclI and KpnI and the BamHI to KpnI excised insert of pMON19701 was ligated into pMON19706 to form pMON19709. This comprises the final CryIIB sequence and contains the DNA sequence identified as SEQ ID NO: 2. This sequence contains 0.15% rare monocotyledonous codons, 9.7% semi-rare monocotyledonous codons, and has a CG dinucleotide composition of 6.7% The resulting modified CryIIB DNA sequence also has 0.05% of the rarest 284 six-mers, 0.37% of the rarest 484 six-mers, and 0.94% of the rarest 664 six-mers. The bacterial CryIA(b) DNA sequence has 9.13% of the rarest 284 six-mers, 15.5% of the rarest 484 six-mers, and 20.13% of the rarest 664 six-mers. The modified DNA sequence as described in Example 1, the monocotyledonous modified B.t. CryIA(b) contains 0.35% of the rarest 284 six-mers, 1.12% of the rarest 484 six-mers, and 2.1% of the rarest 664 six-mers.

pMON19709 was digested with BglII and BclI and inserted into pMON19470, a plasmid map of which is provided in FIG. 12, to form pMON15785. The starting DNA sequence comprising a synthetic CryIIA DNA sequence prepared by the method of Fischoff et al. was inserted into pMON19470 for use as a control for expression studies in corn.

Corn leaf protoplasts were electroporated with CryIIB plasmid DNA or CryIIA plasmid DNA using the protocol described above. The CryIIB DNA sequence, pMON15785, was compared to the CryIIA DNA sequence, pMON19486, in the same corn gene expression cassette. The protoplast electroporation samples were done in duplicate for Western blot analysis and in triplicate for insect bioactivity assays. The protoplast extracts were assayed by diet incorporation into insect feeding assays for tobacco hornworm (THW) and European corn borer (ECB). The protein produced by the CryIIB DNA sequence in pMON15785 showed excellent insecticidal activity that was superior to the insecticidal activity of the CryIIA DNA sequence in the same vector in pMON19486. This data is presented in Table 20 below.

TABLE 20

| Gene construct | % surviving insects | |
| --- | --- | --- |
| | THW | ECB |
| pMON15785 | 0 | 5 |
| pMON19486 | 33 | 88 |
| Control (no B. t.) | 88 | 88 |

Western blots also demonstrated that more protein was detected from pMON15785 than from pMON19486. The antibody used in the Western was raised against CryIIA, so the detection of more CryIIB is significant. Initial transgenic corn plant studies with the CryIIB DNA sequence modified by the method of the present invention have demonstrated insecticidal activity against the European corn borer when the insect was feeding on leaf discs from the transgenic plant. One of fourteen independent transgenic plants containing the modified CryIIB killed the insect. This confirms the initial transient data that the CryIIB DNA sequence is expressed in the plant and is insecticidal to European corn borer and other Lepidopteran pests.

What is claimed is:

1. A structural gene capable of being expressed in a monocotyledonous plant, the gene comprising a modified nucleotide sequence which encodes an insecticidal protein of *Bacillus thuringiensis* and comprises SEQ ID NO:1.

2. A structural gene capable of being expressed in a monocotyledonous plant, the gene comprising a modified nucleotide sequence which encodes an insecticidal protein of *Bacillus thuringiensis* and comprises SEQ ID NO:2.

3. A monocotyledonous plant containing a gene of claim 1.

4. The monocotyledonous plant of claim 3 where in the plant is maize.

5. The monocotyledonous plant of claim 4 wherein expression of the gene is regulated by a promoter selected from the group consisting of tissue specific promoters, constitutive promoters, and inducible promoters.

6. A monocotyledonous plant containing a gene of claim 2.

7. The monocotyledonous plant of claim 6 wherein the plant is maize.

8. The monocotyledonous plant of claim 7 wherein expression of the gene is regulated by a promoter selected from the group consisting of tissue specific promoters, constitutive promoters, and inducible promoters.

9. The monocotyledonous plant of claim 5 wherein said tissue specific promoter is selected from the group consisting of pith specific promoters and meristematic tissue specific promoters.

10. The monocotyledonous plant of claim 8 wherein said tissue specific promoter is selected from the group consisting of pith specific promoters and meristematic tissue specific promoters.

* * * * *

SEQUENCE LISTING ( 1 ) GENERAL INFORMATION:

( i i i ) NUMBER OF SEQUENCES: 164

( 2 ) INFORMATION FOR SEQ ID NO:1:

( i ) SEQUENCE CHARACTERISTICS:
        ( A ) LENGTH: 3478 base pairs
        ( B ) TYPE: nucleic acid
        ( C ) STRANDEDNESS: double
        ( D ) TOPOLOGY: linear ( i i ) MOLECULE TYPE: DNA (synthetic)

( x i ) SEQUENCE DESCRIPTION: SEQ ID NO:1:

```
CCATGGACAA CAACCCAAAC ATCAACGAGT GCATCCCGTA CAACTGCCTC AGCAACCCTG      60
AGGTCGAGGT GCTCGGCGGT GAGCGCATCG AGACCGGTTA CACCCCCATC GACATCTCCC     120
TCTCCCTCAC GCAGTTCCTG CTCAGCGAGT TCGTGCCAGG CGCTGGCTTC GTCCTGGGCC     180
TCGTGGACAT CATCTGGGGC ATCTTTGGCC CCTCCCAGTG GGACGCCTTC CTGGTGCAAA     240
TCGAGCAGCT CATCAACCAG AGGATCGAGG AGTTCGCCAG GAACCAGGCC ATCAGCCGCC     300
TGGAGGGCCT CAGCAACCTC TACCAAATCT ACGCTGAGAG CTTCCGCGAG TGGGAGGCCG     360
ACCCCACTAA CCCAGCTCTC CGCGAGGAGA TGCGCATCCA GTTCAACGAC ATGAACAGCG     420
CCCTGACCAC CGCCATCCCA CTCTTCGCCG TCCAGAACTA CCAAGTCCCG CTCCTGTCCG     480
TGTACGTCCA GGCCGCCAAC CTGCACCTCA GCGTGCTGAG GGACGTCAGC GTGTTTGGCC     540
AGAGGTGGGG CTTCGACGCC GCCACCATCA ACAGCCGCTA CAACGACCTC ACCAGGCTGA     600
TCGGCAACTA CACCGACCAC GCTGTCCGCT GGTACAACAC TGGCCTGGAG CGCGTCTGGG     660
GCCCTGATTC TAGAGACTGG ATTCGCTACA ACCAGTTCAG GCGCGAGCTG ACCCTCACCG     720
TCCTGGACAT TGTGTCCCTC TTCCCGAACT ACGACTCCCG CACCTACCCG ATCCGCACCG     780
TGTCCCAACT GACCCGCGAA ATCTACACCA ACCCCGTCCT GGAGAACTTC GACGGTAGCT     840
TCAGGGGCAG CGCCCAGGGC ATCGAGGGCT CCATCAGGAG CCCACACCTG ATGGACATCC     900
TCAACAGCAT CACTATCTAC ACCGATGCCC ACCGCGGCGA GTACTACTGG TCCGGCCACC     960
AGATCATGGC CTCCCCGGTC GGCTTCAGCG GCCCCGAGTT TACCTTTCCT CTCTACGGCA    1020
CGATGGGCAA CGCCGCTCCA CAACAACGCA TCGTCGCTCA GCTGGGCCAG GGCGTCTACC    1080
GCACCCTGAG CTCCACCCTG TACCGCAGGC CCTTCAACAT CGGTATCAAC AACCAGCAGC    1140
TGTCCGTCCT GGATGGCACT GAGTTCGCCT ACGGCACCTC CTCCAACCTG CCCTCCGCTG    1200
TCTACCGCAA GAGCGGCACG GTGGATTCCC TGGACGAGAT CCCACCACAG AACAACAATG    1260
TGCCCCCCAG GCAGGGTTTT TCCCACAGGC TCAGCCACGT GTCCATGTTC CGCTCCGGCT    1320
```

-continued

```
TCAGCAACTC GTCCGTGAGC ATCATCAGAG CTCCTATGTT CTCCTGGATT CATCGCAGCG   1380
CGGAGTTCAA CAATATCATT CCGTCCTCCC AAATCACCCA AATCCCCCTC ACCAAGTCCA   1440
CCAACCTGGG CAGCGGCACC TCCGTGGTGA AGGGCCCAGG CTTCACGGGC GGCGACATCC   1500
TGCGCAGGAC CTCCCCGGGC CAGATCAGCA CCCTCCGCGT CAACATCACC GCTCCCCTGT   1560
CCCAGAGGTA CCGCGTCAGG ATTCGCTACG CTAGCACCAC CAACCTGCAA TTCCACACCT   1620
CCATCGACGG CAGGCCGATC AATCAGGGTA ACTTCTCCGC CACCATGTCC AGCGGCAGCA   1680
ACCTCCAATC CGGCAGCTTC CGCACCGTGG GTTTCACCAC CCCCTTCAAC TTCTCCAACG   1740
GCTCCAGCGT TTTCACCCTG AGCGCCCACG TGTTCAATTC CGGCAATGAG GTGTACATTG   1800
ACCGCATTGA GTTCGTGCCA GCCGAGGTCA CCTTCGAAGC CGAGTACGAC CTGGAGAGAG   1860
CCCAGAAGGC TGTCAATGAG CTCTTCACGT CCAGCAATCA GATCGGCCTG AAGACCGACG   1920
TCACTGACTA CCACATCGAC CAAGTCTCCA ACCTCGTGGA GTGCCTCTCC GATGAGTTCT   1980
GCCTCGACGA GAAGAAGGAG CTGTCCGAGA AGGTGAAGCA TGCCAAGCGT CTCAGCGACG   2040
AGAGGAATCT CCTCCAGGAC CCCAATTTCC GCGGCATCAA CAGGCAGCTC GACCGCGGCT   2100
GGCGCGGCAG CACCGACATC ACGATCCAGG GCGGCGACGA TGTGTTCAAG GAGAACTACG   2160
TGACTCTCCT GGGCACTTTC GACGAGTGCT ACCCTACCTA CTTGTACCAG AAGATCGATG   2220
AGTCCAAGCT CAAGGCTTAC ACTCGCTACC AGCTCCGCGG CTACATCGAA GACAGCCAAG   2280
ACCTCGAGAT TTACCTGATC CGCTACAACG CCAAGCACGA GACCGTCAAC GTGCCCGGTA   2340
CTGGTTCCCT CTGGCCGCTG AGCGCCCCCA GCCCGATCGG CAAGTGTGCC CACCACAGCC   2400
ACCACTTCTC CTTGGACATC GATGTGGGCT GCACCGACCT GAACGAGGAC CTCGGAGTCT   2460
GGGTCATCTT CAAGATCAAG ACCCAGGACG GCCACGAGCG CCTGGGCAAC CTGGAGTTCC   2520
TCGAGGGCAG GGCCCCCCTG GTCGGTGAGG CTCTGGCCAG GGTCAAGAGG GCTGAGAAGA   2580
AGTGGAGGGA CAAGCGCGAG AAGCTCGAGT GGGAGACCAA CATCGTTTAC AAGGAGGCCA   2640
AGGAGAGCGT CGACGCCCTG TTCGTGAACT CCCAGTACGA CCGCCTGCAG GCCGACACCA   2700
ACATCGCCAT GATCCACGCT GCCGACAAGA GGGTGCACAG CATTCGCGAG GCCTACCTGC   2760
CTGAGCTGTC CGTGATCCCT GGTGTGAACG CTGCCATCTT TGAGGAGCTG GAGGGCCGCA   2820
TCTTTACCGC ATTCTCCCTG TACGACGCCC GCAACGTGAT CAAGAACGGT GACTTCAACA   2880
ATGGCCTCAG CTGCTGGAAC GTCAAGGGCC ACGTGGACGT CGAGGAACAG AACAACCACC   2940
GCTCCGTCCT GGTCGTCCCA GAGTGGGAGG CTGAGGTCTC CAAGAGGTC CGCGTCTGCC   3000
CAGGCCGCGG CTACATTCTC AGGGTCACCG CTTACAAGGA GGGCTACGGT GAGGGCTGTG   3060
TGACCATCCA CGAGATCGAG AACAACACCG ACGAGCTTAA GTTCTCCAAC TGCGTGGAGG   3120
AGGAGGTGTA CCCAAACAAC ACCGTTACTT GCAACGACTA CACCGCCACC CAGGAGGAGT   3180
ACGAGGGCAC CTACACTTCC AGGAACAGGG CTACGATGG TGCCTACGAG AGCAACAGCA   3240
GCGTTCCTGC TGACTACGCT TCCGCCTACG AGGAGAAGGC CTACACGGAT GGCCGCAGGG   3300
ACAACCCTTG CGAGAGCAAC CGCGGCTACG GCGACTACAC TCCCCTGCCC GCCGGCTACG   3360
TTACCAAGGA GCTGGAGTAC TTCCCGGAGA CTGACAAGGT GTGGATCGAG ATCGGCGAGA   3420
CCGAGGGCAC CTTCATCGTG GACAGCGTGG AGCTGCTCCT GATGGAGGAG TAGAATTC    3478
```

(2) INFORMATION FOR SEQ ID NO:2:

( i ) SEQUENCE CHARACTERISTICS:
        ( A ) LENGTH: 1931 base pairs
        ( B ) TYPE: nucleic acid
        ( C ) STRANDEDNESS: double (D) TOPOLOGY: linear (ii) MOLECULE TYPE: DNA (synthetic)

(xi) SEQUENCE DESCRIPTION: SEQ ID NO:2:

```
AGATCTCCAC CATGGACAAC TCCGTCCTGA ACTCTGGTCG CACCACCATC TGCGACGCCT      60
ACAACGTCGC GGCGCATGAT CCATTCAGCT TCCAGCACAA GAGCCTCGAC ACTGTTCAGA     120
AGGAGTGGAC GGAGTGGAAG AAGAACAACC ACAGCCTGTA CCTGGACCCC ATCGTCGGCA     180
CGGTGGCCAG CTTCCTTCTC AAGAAGGTCG GCTCTCTCGT CGGGAAGCGC ATCCTCTCGG     240
AACTCCGCAA CCTGATCTTT CCATCTGGCT CCACCAACCT CATGCAAGAC ATCCTCAGGG     300
AGACCGAGAA GTTTCTCAAC CAGCGCCTCA ACACTGATAC CCTTGCTCGC GTCAACGCTG     360
AGCTGACGGG TCTGCAAGCA AACGTGGAGG AGTTCAACCG CCAAGTGGAC AACTTCCTCA     420
ACCCCAACCG CAATGCGGTG CCTCTGTCCA TCACTTCTTC CGTGAACACC ATGCAACAAC     480
TGTTCCTCAA CCGCTTGCCT CAGTTCCAGA TGCAAGGCTA CCAGCTGCTC CTGCTGCCAC     540
TCTTTGCTCA GGCTGCCAAC CTGCACCTCT CCTTCATTCG TGACGTGATC CTCAACGCTG     600
ACGAGTGGGG CATCTCTGCA GCCACGCTGA GGACCTACCG CGACTACCTG AAGAACTACA     660
CCAGGGACTA CTCCAACTAT TGCATCAACA CCTACCAGTC GGCCTTCAAG GGCCTCAATA     720
CGAGGCTTCA CGACATGCTG GAGTTCAGGA CCTACATGTT CCTGAACGTG TTCGAGTACG     780
TCAGCATCTG GTCGCTCTTC AAGTACCAGA GCCTGCTGGT GTCCAGCGGC GCCAACCTCT     840
ACGCCAGCGG CTCTGGTCCC CAACAAACTC AGAGCTTCAC CAGCCAGGAC TGGCCATTCC     900
TGTATTCGTT GTTCCAAGTC AACTCCAACT ACGTCCTCAA CGGCTTCTCT GGTGCTCGCC     960
TCTCCAACAC CTTCCCCAAC ATTGTTGGCC TCCCCGGCTC CACCACAACT CATGCTCTGC    1020
TTGCTGCCAG AGTGAACTAC TCCGGCGGCA TCTCGAGCGG CGACATTGGT GCATCGCCGT    1080
TCAACCAGAA CTTCAACTGC TCCACCTTCC TGCCGCCGCT GCTCACCCCG TTCGTGAGGT    1140
CCTGGCTCGA CAGCGGCTCC GACCGCGAGG GCGTGGCCAC CGTCACCAAC TGGCAAACCG    1200
AGTCCTTCGA GACCACCCTT GGCCTCCGGA GCGGCGCCTT CACGGCGCGT GGGAATTCTA    1260
ACTACTTCCC CGACTACTTC ATCAGGAACA TCTCTGGTGT TCCTCTCGTC GTCCGCAACG    1320
AGGACCTCCG CCGTCCACTG CACTACAACG AGATCAGGAA CATCGCCTCT CCGTCCGGGA    1380
CGCCCGGAGG TGCAAGGGCG TACATGGTGA GCGTCCATAA CAGGAAGAAC AACATCCACG    1440
CTGTGCATGA GAACGGCTCC ATGATCCACC TGGCGCCCAA TGATTACACC GGCTTCACCA    1500
TCTCTCCAAT CCACGCCACC CAAGTGAACA ACCAGACACG CACCTTCATC TCCGAGAAGT    1560
TCGGCAACCA GGGCGACTCC CTGAGGTTCG AGCAGAACAA CACCACCGCC AGGTACACCC    1620
TGCGCGGCAA CGGCAACAGC TACAACCTGT ACCTGCGCGT CAGCTCCATT GGCAACTCCA    1680
CCATCAGGGT CACCATCAAC GGGAGGGTGT ACACAGCCAC CAATGTGAAC ACGACGACCA    1740
ACAATGATGG CGTCAACGAC AACGGCGCCC GCTTCAGCGA CATCAACATT GGCAACGTGG    1800
TGGCCAGCAG CAACTCCGAC GTCCCGCTGG ACATCAACGT GACCCTGAAC TCTGGCACCC    1860
AGTTCGACCT CATGAACATC ATGCTGGTGC CAACTAACAT CTCGCCGCTG TACTGATAGG    1920
AGCTCTGATC A                                                         1931
```

(2) INFORMATION FOR SEQ ID NO:3:

(i) SEQUENCE CHARACTERISTICS:
 (A) LENGTH: 3531 base pairs
 (B) TYPE: nucleic acid
 (C) STRANDEDNESS: double
 (D) TOPOLOGY: linear (ii) MOLECULE TYPE: DNA (synthetic)

(xi) SEQUENCE DESCRIPTION: SEQ ID NO:3:

| | | | | | | |
|---|---|---|---|---|---|---|
| ATGGACAACA | ACCCAAACAT | CAACGAATGC | ATTCCATACA | ACTGCTTGAG | TAACCCAGAA | 60 |
| GTTGAAGTAC | TTGGTGGAGA | ACGCATTGAA | ACCGGTTACA | CTCCCATCGA | CATCTCCTTG | 120 |
| TCCTTGACAC | AGTTTCTGCT | CAGCGAGTTC | GTGCCAGGTG | CTGGGTTCGT | TCTCGGACTA | 180 |
| GTTGACATCA | TCTGGGGTAT | CTTTGGTCCA | TCTCAATGGG | ATGCATTCCT | GGTGCAAATT | 240 |
| GAGCAGTTGA | TCAACCAGAG | GATCGAAGAG | TTCGCCAGGA | ACCAGGCCAT | CTCTAGGTTG | 300 |
| GAAGGATTGA | GCAATCTCTA | CCAAATCTAT | GCAGAGAGCT | TCAGAGAGTG | GGAAGCCGAT | 360 |
| CCTACTAACC | CAGCTCTCCG | CGAGGAAATG | CGTATTCAAT | TCAACGACAT | GAACAGCGCC | 420 |
| TTGACCACAG | CTATCCCATT | GTTCGCAGTC | CAGAACTACC | AAGTTCCTCT | CTTGTCCGTG | 480 |
| TACGTTCAAG | CAGCTAATCT | TCACCTCAGC | GTGCTTCGAG | ACGTTAGCGT | GTTTGGGCAA | 540 |
| AGGTGGGGAT | CGATGCTGC | AACCATCAAT | AGCCGTTACA | ACGACCTTAC | TAGGCTGATT | 600 |
| GGAAACTACA | CCGACCACGC | TGTTCGTTGG | TACAACACTG | GCTTGGAGCG | TGTCTGGGGT | 660 |
| CCTGATTCTA | GAGATTGGAT | TAGATACAAC | CAGTTCAGGA | GAGAATTGAC | CCTCACAGTT | 720 |
| TTGGACATTG | TGTCTCTCTT | CCCGAACTAT | GACTCCAGAA | CCTACCCTAT | CCGTACAGTG | 780 |
| TCCCAACTTA | CCAGAGAAAT | CTATACTAAC | CCAGTTCTTG | AGAACTTCGA | CGGTAGCTTC | 840 |
| CGTGGTTCTG | CCCAAGGTAT | CGAAGGCTCC | ATCAGGAGCC | ACACTTGAT | GGACATCTTG | 900 |
| AACAGCATAA | CTATCTACAC | CGATGCTCAC | AGAGGAGAGT | ATTACTGGTC | TGGACACCAG | 960 |
| ATCATGGCCT | CTCCAGTTGG | ATTCAGCGGG | CCCGAGTTTA | CCTTTCCTCT | CTATGGAACT | 1020 |
| ATGGGAAACG | CCGCTCCACA | ACAACGTATC | GTTGCTCAAC | TAGGTCAGGG | TGTCTACAGA | 1080 |
| ACCTTGTCTT | CCACCTTGTA | CAGAAGACCC | TTCAATATCG | GTATCAACAA | CCAGCAACTT | 1140 |
| TCCGTTCTTG | ACGGAACAGA | GTTCGCCTAT | GGAACCTCTT | CTAACTTGCC | ATCCGCTGTT | 1200 |
| TACAGAAAGA | GCGGAACCGT | TGATTCCTTG | GACGAAATCC | CACCACAGAA | CAACAATGTG | 1260 |
| CCACCCAGGC | AAGGATTCTC | CCACAGGTTG | AGCCACGTGT | CCATGTTCCG | TTCCGGATTC | 1320 |
| AGCAACAGTT | CCGTGAGCAT | CATCAGAGCT | CCTATGTTCT | CATGGATTCA | TCGTAGTGCT | 1380 |
| GAGTTCAACA | ATATCATTCC | TTCCTCTCAA | ATCACCCAAA | TCCCATTGAC | CAAGTCTACT | 1440 |
| AACCTTGGAT | CTGGAACTTC | TGTCGTGAAA | GGACCAGGCT | TCACAGGAGG | TGATATTCTT | 1500 |
| AGAAGAACTT | CTCCTGGCCA | GATTAGCACC | CTCAGAGTTA | ACATCACTGC | ACCACTTTCT | 1560 |
| CAAAGATATC | GTGTCAGGAT | TCGTTACGCA | TCTACCACTA | ACTTGCAATT | CCACACCTCC | 1620 |
| ATCGACGGAA | GGCCTATCAA | TCAGGGTAAC | TTCTCCGCAA | CCATGTCAAG | CGGCAGCAAC | 1680 |
| TTGCAATCCG | GCAGCTTCAG | AACCGTCGGT | TTCACTACTC | CTTTCAACTT | CTCTAACGGA | 1740 |
| TCAAGCGTTT | TCACCCTTAG | CGCTCATGTG | TTCAATTCTG | GCAATGAAGT | GTACATTGAC | 1800 |
| CGTATTGAGT | TTGTGCCTGC | CGAAGTTACC | CTCGAGGCTG | AGTACAACCT | TGAGAGAGCC | 1860 |
| CAGAAGGCTG | TGAACGCCCT | CTTTACCTCC | ACCAATCAGC | TTGGCTTGAA | AACTAACGTT | 1920 |
| ACTGACTATC | ACATTGACCA | AGTGTCCAAC | TTGGTCACCT | ACCTTAGCGA | TGAGTTCTGC | 1980 |
| CTCGACGAGA | AGCGTGAACT | CTCCGAGAAA | GTTAAACACG | CCAAGCGTCT | CAGCGACGAG | 2040 |
| AGGAATCTCT | TGCAAGACTC | CAACTTCAAA | GACATCAACA | GGCAGCCAGA | ACGTGGTTGG | 2100 |
| GGTGGAAGCA | CCGGGATCAC | CATCCAAGGA | GGCGACGATG | TGTTCAAGGA | GAACTACGTC | 2160 |
| ACCCTCTCCG | GAACTTTCGA | CGAGTGCTAC | CCTACCTACT | TGTACCAGAA | GATCGATGAG | 2220 |
| TCCAAACTCA | AAGCCTTCAC | CAGGTATCAA | CTTAGAGGCT | ACATCGAAGA | CAGCCAAGAC | 2280 |

-continued

| | | | | | |
|---|---|---|---|---|---|
| CTTGAAATCT | ACTCGATCAG | GTACAATGCC | AAGCACGAGA | CCGTGAATGT | CCCAGGTACT | 2340
| GGTTCCCTCT | GGCCACTTTC | TGCCCAATCT | CCCATTGGGA | AGTGTGGAGA | GCCTAACAGA | 2400
| TGCGCTCCAC | ACCTTGAGTG | GAATCCTGAC | TTGGACTGCT | CCTGCAGGGA | TGGCGAGAAG | 2460
| TGTGCCCACC | ATTCTCATCA | CTTCTCCTTG | GACATCGATG | TGGGATGTAC | TGACCTGAAT | 2520
| GAGGACCTCG | GAGTCTGGGT | CATCTTCAAG | ATCAAGACCC | AAGACGGACA | CGCAAGACTT | 2580
| GGCAACCTTG | AGTTTCTCGA | AGAGAAACCA | TTGGTCGGTG | AAGCTCTCGC | TCGTGTGAAG | 2640
| AGAGCAGAGA | AGAAGTGGAG | GGACAAACGT | GAGAAACTCG | AATGGGAAAC | TAACATCGTT | 2700
| TACAAGGAGG | CCAAGAGTC | CGTGGATGCT | TTGTTCGTGA | ACTCCCAATA | TGATCAGTTG | 2760
| CAAGCCGACA | CCAACATCGC | CATGATCCAC | GCCGCAGACA | AACGTGTGCA | CAGCATTCGT | 2820
| GAGGCTTACT | TGCCTGAGTT | GTCCGTGATC | CCTGGTGTGA | ACGCTGCCAT | CTTCGAGGAA | 2880
| CTTGAGGGAC | GTATCTTTAC | CGCATTCTCC | TTGTACGATG | CCAGAAACGT | CATCAAGAAC | 2940
| GGTGACTTCA | ACAATGGCCT | CAGCTGCTGG | AATGTGAAAG | GTCATGTGGA | CGTGGAGGAA | 3000
| CAGAACAATC | AGCGTTCCGT | CCTGGTTGTG | CCTGAGTGGG | AAGCTGAAGT | GTCCCAAGAG | 3060
| GTTAGAGTCT | GTCCAGGTAG | AGGCTACATT | CTCCGTGTGA | CCGCTTACAA | GGAGGGATAC | 3120
| GGTGAGGGTT | GCGTGACCAT | CCACGAGATC | GAGAACAACA | CCGACGAGCT | TAAGTTCTCC | 3180
| AACTGCGTCG | AGGAAGAAAT | CTATCCCAAC | AACACCGTTA | CTTGCAACGA | CTACACTGTG | 3240
| AATCAGGAAG | AGTACGGAGG | TGCCTACACT | AGCCGTAACA | GAGGTTACAA | CGAAGCTCCT | 3300
| TCCGTTCCTG | CTGACTATGC | CTCCGTGTAC | GAGGAGAAAT | CCTACACAGA | TGGCAGACGT | 3360
| GAGAACCCTT | GCGAGTTCAA | CAGAGGTTAC | AGGGACTACA | CACCACTTCC | AGTTGGCTAT | 3420
| GTTACCAAGG | AGCTTGAGTA | CTTTCCTGAG | ACCGACAAAG | TGTGGATCGA | GATCGGTGAA | 3480
| ACCGAGGGAA | CCTTCATCGT | GGACAGCGTG | GAGCTTCTCT | TGATGGAGGA | A | 3531

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

TCGAGTGATT CGAATGAG                                                              18

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

AATTCTCATT CGAATCAC                                                              18

( 2 ) INFORMATION FOR SEQ ID NO:6:

( i ) SEQUENCE CHARACTERISTICS:
        ( A ) LENGTH: 63 base pairs
        ( B ) TYPE: nucleic acid
        ( C ) STRANDEDNESS: single ( D ) TOPOLOGY: linear ( i i ) MOLECULE TYPE: DNA (synthetic)

( x i ) SEQUENCE DESCRIPTION: SEQ ID NO:6:

TCTAGAGACT GGATTCGCTA CAACCAGTTC AGGCGCGAGC TGACCCTCAC CGTCCTGGAC    60

ATT    63

( 2 ) INFORMATION FOR SEQ ID NO:7:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:7:

ATTGTGTCCC TCTTCCCGAA CTACGACTCC CGCACCTACC C    41

( 2 ) INFORMATION FOR SEQ ID NO:8:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:8:

ACCTACCCGA TCCGCACCGT GTCCCAACTG ACCCGCGAAA TCT    43

( 2 ) INFORMATION FOR SEQ ID NO:9:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:9:

AAATCTACAC CAACCCCGTC CTGGAGAACT TC    32

( 2 ) INFORMATION FOR SEQ ID NO:10:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:10:

AGCTTCAGGG GCAGCGCCCA GGGCATCGAG GGCTCCATC    39

( 2 ) INFORMATION FOR SEQ ID NO:11:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:11:

GCCCACACCT GATGGACATC CTCAACAGCA TCACTATCTA C          41

( 2 ) INFORMATION FOR SEQ ID NO:12:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:12:

TACACCGATG CCCACCGCGG CGAGTACTAC TGGTCCGGCC ACCAGATC          48

( 2 ) INFORMATION FOR SEQ ID NO:13:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:13:

ATGGCCTCCC CGGTCGGCTT CAGCGGCCCC GAGTT          35

( 2 ) INFORMATION FOR SEQ ID NO:14:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:14:

CCTCTCTACG GCACGATGGG CAACGCCGC          29

( 2 ) INFORMATION FOR SEQ ID NO:15:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:15:

CAACAACGCA TCGTCGCTCA GCTGGGCCAG GGTGTCTACA G          41

( 2 ) INFORMATION FOR SEQ ID NO:16:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:16:

GCGTCTACCG CACCCTGAGC TCCACCCTGT ACCGCAGGCC CTTCAACATC GGTATC          56

( 2 ) INFORMATION FOR SEQ ID NO:17:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:17:

AACCAGCAGC TGTCCGTCCT GGATGGCACT GAGTTCGC        38

( 2 ) INFORMATION FOR SEQ ID NO:18:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:18:

TTCGCCTACG GCACCTCCTC CAACCTGCCC TCCGCTGTCT ACCGCAAGAG CGG        53

( 2 ) INFORMATION FOR SEQ ID NO:19:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:19:

AAGAGCGGCA CGGTGGATTC CCTGGACGAG ATCCCACC        38

( 2 ) INFORMATION FOR SEQ ID NO:20:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:20:

AATGTGCCCC CCAGGCAGGG TTTTCCCAC AGGCTCAGCC ACGT        44

( 2 ) INFORMATION FOR SEQ ID NO:21:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:21:

ATGTTCCGCT CCGGCTTCAG CAACTCGTCC GTGAGC        36

( 2 ) INFORMATION FOR SEQ ID NO:22:

( i ) SEQUENCE CHARACTERISTICS:
        ( A ) LENGTH: 33 base pairs ( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:22:

GGGCAGCGCC CAGGGCATCG AGGGCTCCAT CAG 33

( 2 ) INFORMATION FOR SEQ ID NO:23:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:23:

TGCCCACCGC GGCGAGTAC 19

( 2 ) INFORMATION FOR SEQ ID NO:24:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:24:

CCGGTCGGCT TCAGCGGCCC CGAGTTTAC 29

( 2 ) INFORMATION FOR SEQ ID NO:25:

( i ) SEQUENCE CHARACTERISTICS:
( A ) LENGTH: 63 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:25:

GGCCAGGGCG TCTACCGCAC CCTGAGCTCC ACCCTGTACC GCAGGCCCTT CAACATCGGT 60

ATC 63

( 2 ) INFORMATION FOR SEQ ID NO:26:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:26:

CTGTCCGTCC TGGATGGCAC TGAGTTCGC 29

( 2 ) INFORMATION FOR SEQ ID NO:27:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:27:

TCAGCAACTC GTCCGTGAGC 20

( 2 ) INFORMATION FOR SEQ ID NO:28:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:28:

ATGTTCTCCT GGATTCATCG CAGCGCGGAG TTCAAC 36

( 2 ) INFORMATION FOR SEQ ID NO:29:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:29:

TCATTCCGTC CTCCCAAATC ACCCAAATCC CCCTCACCAA GTC 43

( 2 ) INFORMATION FOR SEQ ID NO:30:

( i ) SEQUENCE CHARACTERISTICS:
( A ) LENGTH: 53 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:30:

ACCAAGTCCA CCAACCTGGG CAGCGGCACC TCCGTGGTGA AGGGCCCAGG CTT 53

( 2 ) INFORMATION FOR SEQ ID NO:31:

( i ) SEQUENCE CHARACTERISTICS:
( A ) LENGTH: 56 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:31:

GGCTTCACGG GCGGCGACAT CCTGCGCAGG ACCTCCCCGG GCCAGATCAG CACCCT 56

( 2 ) INFORMATION FOR SEQ ID NO:32:

( i ) SEQUENCE CHARACTERISTICS:
( A ) LENGTH: 59 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:32:

GCACCCTCCG CGTCAACATC ACCGCTCCCC TGTCCCAGAG GTACGTACCG CGTCAGGAT 59

( 2 ) INFORMATION FOR SEQ ID NO:33:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:33:

AGGATTCGCT ACGCTAGCAC CACCAACCTG CAATTC 36

( 2 ) INFORMATION FOR SEQ ID NO:34:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:34:

ATCGACGGCA GGCCGATCAA TCAG 24

( 2 ) INFORMATION FOR SEQ ID NO:35:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:35:

TTCTCCGCCA CCATGTCCAG CGGCAGCAAC CTCCAATCCG G 41

( 2 ) INFORMATION FOR SEQ ID NO:36:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:36:

GCAGCTTCCG CACCGTGGGT TTCACCACCC CCTTCAACTT C 41

( 2 ) INFORMATION FOR SEQ ID NO:37:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:37:

AACTTCTCCA ACGGCTCCAG CGTTTTCACC CTGAGCGCTC A 41

( 2 ) INFORMATION FOR SEQ ID NO:38:

( i ) SEQUENCE CHARACTERISTICS:
    ( A ) LENGTH: 56 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:38:

CTGAGCGCCC ACGTGTTCAA TTCCGGCAAT GAGGTGTACA TTGACCGCAT TGAGTT    56

( 2 ) INFORMATION FOR SEQ ID NO:39:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:39:

ATTGAGTTCG TGCCAGCCGA GGTCACCTTC GAAGGGGGC C    41

( 2 ) INFORMATION FOR SEQ ID NO:40:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:40:

TGAAGGGCCC AGGCTTCACG GGCGGCGACA TCCTGCGCAG GACCTC    46

( 2 ) INFORMATION FOR SEQ ID NO:41:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:41:

CTAGCACCAC CAACCTGCAA TTCCACACCT CCATC    35

( 2 ) INFORMATION FOR SEQ ID NO:42:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:42:

GGGGATCCAC CATGGACAAC    20

( 2 ) INFORMATION FOR SEQ ID NO:43:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:43:

ATCAACGAGT GCATCCCGTA CAACTGCCTC AGCAACCCTG AGGTCGAGGT ACTTGG  56

( 2 ) INFORMATION FOR SEQ ID NO:44:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:44:

GAGGTCGAGG TGCTCGGCGG TGAGCGCATC GAGACCGGTT ACACCCCAT CG  52

( 2 ) INFORMATION FOR SEQ ID NO:45:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:45:

ACATCTCCCT CTCCCTCACG CAGTTCCTGC TCAG  34

( 2 ) INFORMATION FOR SEQ ID NO:46:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:46:

GTGCCAGGCG CTGGCTTCGT CCTGGGCCTC GTGGACATCA TC  42

( 2 ) INFORMATION FOR SEQ ID NO:47:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:47:

ATCTGGGGCA TCTTTGGCCC CTCCCAGTGG GACGCCTTCC TGGT  44

( 2 ) INFORMATION FOR SEQ ID NO:48:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:48:

GTGCAAATCG AGCAGCTCAT CAACCAGAGG ATCGAGGAGT TCGC    44

( 2 ) INFORMATION FOR SEQ ID NO:49:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:49:

AGGCCATCAG CCGCCTGGAG GGCCTCAGCA ACCTCTACCA AATCTACGCT GAGAGCTT    58

( 2 ) INFORMATION FOR SEQ ID NO:50:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:50:

AGAGCTTCCG CGAGTGGGAG GCCGACCCCA CTAACCC    37

( 2 ) INFORMATION FOR SEQ ID NO:51:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:51:

CGCGAGGAGA TGCGCATCCA GTTCAACGAC    30

( 2 ) INFORMATION FOR SEQ ID NO:52:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:52:

ACAGCGCCCT GACCACCGCC ATCCACTCT TCGCCGTCCA GAAC    44

( 2 ) INFORMATION FOR SEQ ID NO:53:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:53:

TACCAAGTCC CGCTCCTGTC CGTGTACGTC CAGGCCGCCA ACCTGCACCT CAG    53

( 2 ) INFORMATION FOR SEQ ID NO:54:

( i ) SEQUENCE CHARACTERISTICS:
   ( A ) LENGTH: 62 base pairs
   ( B ) TYPE: nucleic acid
   ( C ) STRANDEDNESS: single
   ( D ) TOPOLOGY: linear ( i i ) MOLECULE TYPE: DNA (synthetic)

( x i ) SEQUENCE DESCRIPTION: SEQ ID NO:54:

AGCGTGCTGA GGGACGTCAG CGTGTTTGGC CAGAGGTGGG GCTTCGACGC CGCCACCATC    60

AA    62

( 2 ) INFORMATION FOR SEQ ID NO:55:

( i ) SEQUENCE CHARACTERISTICS:
   ( A ) LENGTH: 50 base pairs
   ( B ) TYPE: nucleic acid
   ( C ) STRANDEDNESS: single
   ( D ) TOPOLOGY: linear ( i i ) MOLECULE TYPE: DNA (synthetic)

( x i ) SEQUENCE DESCRIPTION: SEQ ID NO:55:

ACCATCAACA GCCGCTACAA CGACCTCACC AGGCTGATCG GCAACTACAC    50

( 2 ) INFORMATION FOR SEQ ID NO:56:

( i ) SEQUENCE CHARACTERISTICS:
   ( A ) LENGTH: 53 base pairs
   ( B ) TYPE: nucleic acid
   ( C ) STRANDEDNESS: single
   ( D ) TOPOLOGY: linear ( i i ) MOLECULE TYPE: DNA (synthetic)

( x i ) SEQUENCE DESCRIPTION: SEQ ID NO:56:

CACGCTGTCC GCTGGTACAA CACTGGCCTG GAGCGCGTCT GGGGCCCTGA TTC    53

( 2 ) INFORMATION FOR SEQ ID NO:57:

( i ) SEQUENCE CHARACTERISTICS:
   ( A ) LENGTH: 17 base pairs
   ( B ) TYPE: nucleic acid
   ( C ) STRANDEDNESS: single
   ( D ) TOPOLOGY: linear ( i i ) MOLECULE TYPE: DNA (synthetic)

( x i ) SEQUENCE DESCRIPTION: SEQ ID NO:57:

GGCGCTGGCT TCGTCCT    17

( 2 ) INFORMATION FOR SEQ ID NO:58:

( i ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear ( i i ) MOLECULE TYPE: DNA (synthetic)

( x i ) SEQUENCE DESCRIPTION: SEQ ID NO:58:

CAAATCTACG CTGAGAGCTT    20

( 2 ) INFORMATION FOR SEQ ID NO:59:

( i ) SEQUENCE CHARACTERISTICS:
   ( A ) LENGTH: 22 base pairs
   ( B ) TYPE: nucleic acid

```
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:59:

TAACCCAGCT CTCCGCGAGG AG                                                        22

( 2 ) INFORMATION FOR SEQ ID NO:60:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:60:

CTTCGACGCC GCCACCAT                                                             18

( 2 ) INFORMATION FOR SEQ ID NO:61:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:61:

GGGCCCCCCT TCGAAGCCGA GTACGACCTG GAGAGAGC                                       38

( 2 ) INFORMATION FOR SEQ ID NO:62:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:62:

AAGGCTGTCA ATGAGCTCTT CACGTCCAGC AATCAG                                         36

( 2 ) INFORMATION FOR SEQ ID NO:63:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:63:

CAATCAGATC GGCCTGAAGA CCGACGTCAC TGACTA                                         36

( 2 ) INFORMATION FOR SEQ ID NO:64:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (synthetic)
```

( x i ) SEQUENCE DESCRIPTION: SEQ ID NO:64:

ACTGACTACC ACATCGACCA AGTCTCCAAC CTCGTGGAGT GCCTCTCCGA TGAGT 55

( 2 ) INFORMATION FOR SEQ ID NO:65:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:65:

ACGAGAAGAA GGAGCTGTCC GAGAAGGTGA AGCATGCCAA GCG 43

( 2 ) INFORMATION FOR SEQ ID NO:66:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:66:

GGAATCTCCT CCAGGACCCC AATTTCCGCG GCATCAACA 39

( 2 ) INFORMATION FOR SEQ ID NO:67:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:67:

CAGGCAGCTC GACCGCGGCT GGCGCGGCAG CACCG 35

( 2 ) INFORMATION FOR SEQ ID NO:68:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:68:

AGCACCGACA TCACGATCCA GGGCGGCGAC GA 32

( 2 ) INFORMATION FOR SEQ ID NO:69:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:69:

AACTACGTGA CTCTCCTGGG CACTTTCGA 29

( 2 ) INFORMATION FOR SEQ ID NO:70:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:70:

GAGTCCAAGC TCAAGGCTTA CACTCGCTAC CAGCTCCGCG GCTACAT    47

( 2 ) INFORMATION FOR SEQ ID NO:71:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:71:

CAAGACCTCG AGATTTACCT GATCCGCTAC AACGCCAAGC A    41

( 2 ) INFORMATION FOR SEQ ID NO:72:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:72:

GAGACCGTCA ACGTGCCCGG TACTGG    26

( 2 ) INFORMATION FOR SEQ ID NO:73:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:73:

CTCTGGCCGC TGAGCGCCCC CAGCCCGATC GGCAAGTGTG    40

( 2 ) INFORMATION FOR SEQ ID NO:74:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:74:

CCCACCACAG CCACCACTTC TC    22

( 2 ) INFORMATION FOR SEQ ID NO:75:

( i ) SEQUENCE CHARACTERISTICS:
        ( A ) LENGTH: 32 base pairs
        ( B ) TYPE: nucleic acid

```
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:75:
```

GATGTGGGCT GCACCGACCT GAACGAGGAC CT                32

( 2 ) INFORMATION FOR SEQ ID NO:76:

```
    ( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:76:
```

AAGACCCAGG ACGGCACGA GCGCCTGGGC AACCT              35

( 2 ) INFORMATION FOR SEQ ID NO:77:

```
    ( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:77:
```

GGCAACCTGG AGTTCCTCGA GGGCAGGGCC CCCCTGGTCG GT      42

( 2 ) INFORMATION FOR SEQ ID NO:78:

```
    ( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:78:
```

GTCGGTGAGG CTCTGGCCAG GGTCAAGAGG GCTGAGAAGA A       41

( 2 ) INFORMATION FOR SEQ ID NO:79:

```
    ( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:79:
```

AGGGACAAGC GCGAGAAGCT CGAGTGGGAG ACCAACATCG T       41

( 2 ) INFORMATION FOR SEQ ID NO:80:

```
    ( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)
```

( x i ) SEQUENCE DESCRIPTION: SEQ ID NO:80:

GAGGCCAAGG AGAGCGTCGA CGCCCTGTTC GTG    33

( 2 ) INFORMATION FOR SEQ ID NO:81:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:81:

AACTCCCAGT ACGACCGCCT GCAGGCCGAC AC    32

( 2 ) INFORMATION FOR SEQ ID NO:82:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:82:

ATCCACGCTG CCGACAAGAG GGTGCACA    28

( 2 ) INFORMATION FOR SEQ ID NO:83:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:83:

GCATTCGCGA GGCCTACCTG CCTGAGCTGT CCGTG    35

( 2 ) INFORMATION FOR SEQ ID NO:84:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:84:

GCCATCTTTG AGGAGCTGGA GGGCCGCATC TTTAC    35

( 2 ) INFORMATION FOR SEQ ID NO:85:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:85:

CATTCTCCCT GTACGACGCC CGCAACGTGA TCAAGAA    37

( 2 ) INFORMATION FOR SEQ ID NO:86:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:86:

GGCCTCAGCT GGAATTCCTG                                                                   20

( 2 ) INFORMATION FOR SEQ ID NO:87:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:87:

CAAGAGGGCT GAGAAGAAGT GGAGGGACAA G                                      31

( 2 ) INFORMATION FOR SEQ ID NO:88:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:88:

TACTGGTTCC CTCTGGCCGC TGAGCGCCCC CAGCCCGATC GGCAAGTGTG CCCACCACA       59

( 2 ) INFORMATION FOR SEQ ID NO:89:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:89:

ATAAGCTTCA GCTGCTGGAA CGTCAAGGGC CACGTGGACG TCGAGGAAC                 49

( 2 ) INFORMATION FOR SEQ ID NO:90:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:90:

AGAACAACCA CCGCTCCGTC CTGGTCGTCC CAGAGTGGGA                          40

( 2 ) INFORMATION FOR SEQ ID NO:91:

( i ) SEQUENCE CHARACTERISTICS:
        ( A ) LENGTH: 26 base pairs
        ( B ) TYPE: nucleic acid (C) STRANDEDNESS: single
(D) TOPOLOGY: linear (ii) MOLECULE TYPE: DNA (synthetic)

(xi) SEQUENCE DESCRIPTION: SEQ ID NO:91:

GAGTGGGAGG CTGAGGTCTC CCAAGA    26

(2) INFORMATION FOR SEQ ID NO:92:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:92:

CAAGAGGTCC GCGTCTGCCC AGGCCGCGGC TACATTCTCA GGGTCACCGC TTA    53

(2) INFORMATION FOR SEQ ID NO:93:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:93:

AAGGAGGGCT ACGGTGAGGG CTGTGTGACC AT    32

(2) INFORMATION FOR SEQ ID NO:94:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:94:

AACTGCGTGG AGGAGGAGGT GTACCCAAAC AACAC    35

(2) INFORMATION FOR SEQ ID NO:95:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:95:

GACTACACCG CCACCCAGGA GGAGTACGAG GGCACCTACA CT    42

(2) INFORMATION FOR SEQ ID NO:96:

(i) SEQUENCE CHARACTERISTICS:
(A) LENGTH: 60 base pairs
(B) TYPE: nucleic acid
(C) STRANDEDNESS: single
(D) TOPOLOGY: linear (ii) MOLECULE TYPE: DNA (synthetic)

( x i ) SEQUENCE DESCRIPTION: SEQ ID NO:96:

CCTACACTTC CAGGAACAGG GGCTACGATG GTGCCTACGA GAGCAACAGC AGCGTTCCTG    60

( 2 ) INFORMATION FOR SEQ ID NO:97:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:97:

CTGACTACGC TTCCGCCTAC GAGGAGAAGG CCTACAC    37

( 2 ) INFORMATION FOR SEQ ID NO:98:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:98:

CCTACACGGA TGGCCGCAGG GACAACCCTT G    31

( 2 ) INFORMATION FOR SEQ ID NO:99:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:99:

CTTGCGAGAG CAACCGCGGC TACGGCGACT ACAC    34

( 2 ) INFORMATION FOR SEQ ID NO:100:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:100:

GACTACACTC CCCTGCCCGC CGGCTACGTT ACCA    34

( 2 ) INFORMATION FOR SEQ ID NO:101:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:101:

AGGAGCTGGA GTACTTCCCG GAGACTGACA AGGTGTGGA    39

( 2 ) INFORMATION FOR SEQ ID NO:102:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:102:

```
TCGAGATCGG CGAGACCGAG GGCACCTTCA T                                    31
```

( 2 ) INFORMATION FOR SEQ ID NO:103:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:103:

```
GTGGAGCTGC TCCTGATGGA GGAGTAGAAT TCCTCTAAGC T                         41
```

( 2 ) INFORMATION FOR SEQ ID NO:104:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:104:

```
CTGGTCGTCC CAGAGTGGGA GGCTGAGGTC TCCCAAGAGG TCCGCGTCTG CCCAGGCCG      59
```

( 2 ) INFORMATION FOR SEQ ID NO:105:

( i ) SEQUENCE CHARACTERISTICS:
        ( A ) LENGTH: 3484 base pairs
        ( B ) TYPE: nucleic acid
        ( C ) STRANDEDNESS: double
        ( D ) TOPOLOGY: linear ( i i ) MOLECULE TYPE: DNA (synthetic)

( x i ) SEQUENCE DESCRIPTION: SEQ ID NO:105:

```
AGATCTCCAT GGACAACAAC CCAAACATCA ACGAATGCAT TCCATACAAC TGCTTGAGTA     60
ACCCAGAAGT TGAAGTACTT GGTGGAGAAC GCATTGAAAC CGGTTACACT CCCATCGACA    120
TCTCCTTGTC CTTGACACAG TTTCTGCTCA GCGAGTTCGT GCCAGGTGCT GGGTTCGTTC    180
TCGGACTAGT TGACATCATC TGGGGTATCT TTGGTCCATC TCAATGGGAT GCATTCCTGG    240
TGCAAATTGA GCAGTTGATC AACCAGAGGA TCGAAGAGTT CGCCAGGAAC CAGGCCATCT    300
CTAGGTTGGA AGGATTGAGC AATCTCTACC AAATCTATGC AGAGAGCTTC AGAGAGTGGG    360
AAGCCGATCC TACTAACCCA GCTCTCCGCG AGGAAATGCG TATTCAATTC AACGACATGA    420
ACAGCGCCTT GACCACAGCT ATCCCATTGT TCGCAGTCCA GAACTACCAA GTTCCTCTCT    480
TGTCCGTGTA CGTTCAAGCA GCTAATCTTC ACCTCAGCGT GCTTCGAGAC GTTAGCGTGT    540
TTGGGCAAAG GTGGGGATTC GATGCTGCAA CCATCAATAG CCGTTACAAC GACCTTACTA    600
GGCTGATTGG AAACTACACC GACCACGCTG TTCGTTGGTA CAACACTGGC TTGGAGCGTG    660
TCTGGGGTCC TGATTCTAGA GATTGGATTA GATACAACCA GTTCAGGAGA GAATTGACCC    720
```

| | | | | | |
|---|---|---|---|---|---|
| TCACAGTTTT | GGACATTGTG | TCTCTCTTCC | CGAACTATGA | CTCCAGAACC | TACCCTATCC | 780
| GTACAGTGTC | CCAACTTACC | AGAGAAATCT | ATACTAACCC | AGTTCTTGAG | AACTTCGACG | 840
| GTAGCTTCCG | TGGTTCTGCC | CAAGGTATCG | AAGGCTCCAT | CAGGAGCCCA | CACTTGATGG | 900
| ACATCTTGAA | CAGCATAACT | ATCTACACCG | ATGCTCACAG | AGGAGAGTAT | TACTGGTCTG | 960
| GACACCAGAT | CATGGCCTCT | CCAGTTGGAT | TCAGCGGGCC | CGAGTTTACC | TTTCCTCTCT | 1020
| ATGGAACTAT | GGGAAACGCC | GCTCCACAAC | AACGTATCGT | TGCTCAACTA | GGTCAGGGTG | 1080
| TCTACAGAAC | CTTGTCTTCC | ACCTTGTACA | GAAGACCCTT | CAATATCGGT | ATCAACAACC | 1140
| AGCAACTTTC | CGTTCTTGAC | GGAACAGAGT | TCGCCTATGG | AACCTCTTCT | AACTTGCCAT | 1200
| CCGCTGTTTA | CAGAAAGAGC | GGAACCGTTG | ATTCCTTGGA | CGAAATCCCA | CCACAGAACA | 1260
| ACAATGTGCC | ACCCAGGCAA | GGATTCTCCC | ACAGGTTGAG | CCACGTGTCC | ATGTTCCGTT | 1320
| CCGGATTCAG | CAACAGTTCC | GTGAGCATCA | TCAGAGCTCC | TATGTTCTCA | TGGATTCATC | 1380
| GTAGTGCTGA | GTTCAACAAT | ATCATTCCTT | CCTCTCAAAT | CACCCAAATC | CCATTGACCA | 1440
| AGTCTACTAA | CCTTGGATCT | GGAACTTCTG | TCGTGAAAGG | ACCAGGCTTC | ACAGGAGGTG | 1500
| ATATTCTTAG | AAGAACTTCT | CCTGGCCAGA | TTAGCACCCT | CAGAGTTAAC | ATCACTGCAC | 1560
| CACTTTCTCA | AAGATATCGT | GTCAGGATTC | GTTACGCATC | TACCACTAAC | TTGCAATTCC | 1620
| ACACCTCCAT | CGACGGAAGG | CCTATCAATC | AGGGTAACTT | CTCCGCAACC | ATGTCAAGCG | 1680
| GCAGCAACTT | GCAATCCGGC | AGCTTCAGAA | CCGTCGGTTT | CACTACTCCT | TTCAACTTCT | 1740
| CTAACGGATC | AAGCGTTTTC | ACCCTTAGCG | CTCATGTGTT | CAATTCTGGC | AATGAAGTGT | 1800
| ACATTGACCG | TATTGAGTTT | GTGCCTGCCG | AAGTTACCTT | CGAAGCCGAG | TACGACCTGG | 1860
| AGAGAGCCCA | GAAGGCTGTC | AATGAGCTCT | TCACGTCCAG | CAATCAGATC | GGCCTGAAGA | 1920
| CCGACGTCAC | TGACTACCAC | ATCGACCAAG | TCTCCAACCT | CGTGGAGTGC | CTCTCCGATG | 1980
| AGTTCTGCCT | CGACGAGAAG | AAGGAGCTGT | CCGAGAAGGT | GAAGCATGCC | AAGCGTCTCA | 2040
| GCGACGAGAG | GAATCTCCTC | CAGGACCCCA | ATTTCCGCGG | CATCAACAGG | CAGCTCGACC | 2100
| GCGGCTGGCG | CGGCAGCACC | GACATCACGA | TCCAGGGCGG | CGACGATGTG | TTCAAGGAGA | 2160
| ACTACGTGAC | TCTCCTGGGC | ACTTTCGACG | AGTGCTACCC | TACCTACTTG | TACCAGAAGA | 2220
| TCGATGAGTC | CAAGCTCAAG | GCTTACACTC | GCTACCAGCT | CCGCGGCTAC | ATCGAAGACA | 2280
| GCCAAGACCT | CGAGATTTAC | CTGATCCGCT | ACAACGCCAA | GCACGAGACC | GTCAACGTGC | 2340
| CCGGTACTGG | TTCCCTCTGG | CCGCTGAGCG | CCCCCAGCCC | GATCGGCAAG | TGTGCCCACC | 2400
| ACAGCCACCA | CTTCTCCTTG | GACATCGATG | TGGGCTGCAC | CGACCTGAAC | GAGGACCTCG | 2460
| GAGTCTGGGT | CATCTTCAAG | ATCAAGACCC | AGGACGGCCA | CGAGCGCCTG | GGCAACCTGG | 2520
| AGTTCCTCGA | GGGCAGGGCC | CCCCTGGTCG | GTGAGGCTCT | GGCCAGGGTC | AAGAGGGCTG | 2580
| AGAAGAAGTG | GAGGGACAAG | CGCGAGAAGC | TCGAGTGGGA | GACCAACATC | GTTTACAAGG | 2640
| AGGCCAAGGA | GAGCGTCGAC | GCCCTGTTCG | TGAACTCCCA | GTACGACCGC | CTGCAGGCCG | 2700
| ACACCAACAT | CGCCATGATC | CACGCTGCCG | ACAAGAGGGT | GCACAGCATT | CGCGAGGCCT | 2760
| ACCTGCCTGA | GCTGTCCGTG | ATCCCTGGTG | TGAACGCTGC | CATCTTTGAG | GAGCTGGAGG | 2820
| GCCGCATCTT | TACCGCATTC | TCCCTGTACG | ACGCCCGCAA | CGTGATCAAG | AACGGTGACT | 2880
| TCAACAATGG | CCTCAGCTGC | TGGAACGTCA | AGGGCCACGT | GGACGTCGAG | GAACAGAACA | 2940
| ACCACCGCTC | CGTCCTGGTC | GTCCCAGAGT | GGGAGGCTGA | GGTCTCCCAA | GAGGTCCGCG | 3000
| TCTGCCCAGG | CCGCGGCTAC | ATTCTCAGGG | TCACCGCTTA | CAAGGAGGGC | TACGGTGAGG | 3060
| GCTGTGTGAC | CATCCACGAG | ATCGAGAACA | ACACCGACGA | GCTTAAGTTC | TCCAACTGCG | 3120

| | | | | | |
|---|---|---|---|---|---|
| TGGAGGAGGA | GGTGTACCCA | AACAACACCG | TTACTTGCAA | CGACTACACC | GCCACCCAGG | 3180
| AGGAGTACGA | GGGCACCTAC | ACTTCCAGGA | ACAGGGGCTA | CGATGGTGCC | TACGAGAGCA | 3240
| ACAGCAGCGT | TCCTGCTGAC | TACGCTTCCG | CCTACGAGGA | GAAGGCCTAC | ACGGATGGCC | 3300
| GCAGGGACAA | CCCTTGCGAG | AGCAACCGCG | GCTACGGCGA | CTACACTCCC | CTGCCCGCCG | 3360
| GCTACGTTAC | CAAGGAGCTG | GAGTACTTCC | CGGAGACTGA | CAAGGTGTGG | ATCGAGATCG | 3420
| GCGAGACCGA | GGGCACCTTC | ATCGTGGACA | GCGTGGAGCT | GCTCCTGATG | GAGGAGTAGA | 3480
| ATTC | | | | | | 3484

(2) INFORMATION FOR SEQ ID NO:106:

(i) SEQUENCE CHARACTERISTICS:
    (A) LENGTH: 1919 base pairs
    (B) TYPE: nucleic acid
    (C) STRANDEDNESS: double
    (D) TOPOLOGY: linear (ii) MOLECULE TYPE: DNA (synthetic)

(xi) SEQUENCE DESCRIPTION: SEQ ID NO:106:

| | | | | | |
|---|---|---|---|---|---|
| ATGGACAACA | ACGTCTTGAA | CTCTGGTAGA | ACAACCATCT | GCGACGCATA | CAACGTCGTG | 60
| GCTCACGATC | CATTCAGCTT | CGAACACAAG | AGCCTCGACA | CTATTCAGAA | GGAGTGGATG | 120
| GAATGGAAAC | GTACTGACCA | CTCTCTCTAC | GTCGCACCTG | TGGTTGGAAC | AGTGTCCAGC | 180
| TTCCTTCTCA | AGAAGGTCGG | CTCTCTCATC | GGAAAACGTA | TCTTGTCCGA | ACTCTGGGGT | 240
| ATCATCTTTC | CATCTGGGTC | CACTAATCTC | ATGCAAGACA | TCTTGAGGGA | GACCGAACAG | 300
| TTTCTCAACC | AGCGTCTCAA | CACTGATACC | TTGGCTAGAG | TCAACGCTGA | GTTGATCGGT | 360
| CTCCAAGCAA | ACATTCGTGA | GTTCAACCAG | CAAGTGGACA | ACTTCTTGAA | TCCAACTCAG | 420
| AATCCTGTGC | CTCTTTCCAT | CACTTCTTCC | GTGAACACTA | TGCAGCAACT | CTTCCTCAAC | 480
| AGATTGCCTC | AGTTTCAGAT | TCAAGGCTAC | CAGTTGCTCC | TTCTTCCACT | CTTTGCTCAG | 540
| GCTGCCAACA | TGCACTTGTC | CTTCATACGT | GACGTGATCC | TCAACGCTGA | CGAATGGGGA | 600
| ATCTCTGCAG | CCACTCTTAG | GACATACAGA | GACTACTTGA | GGAACTACAC | TCGTGATTAC | 660
| TCCAACTATT | GCATCAACAC | TTATCAGACT | GCCTTTCGTG | GACTCAATAC | TAGGCTTCAC | 720
| GACATGCTTG | AGTTCAGGAC | CTACATGTTC | CTTAACGTGT | TGAGTACGT | CAGCATTTGG | 780
| AGTCTCTTCA | AGTACCAGAG | CTTGATGGTG | TCCTCTGGAG | CCAATCTCTA | CGCCTCTGGC | 840
| AGTGGACCAC | AGCAAACTCA | GAGCTTCACA | GCTCAGAACT | GGCCATTCTT | GTATAGCTTG | 900
| TTCCAAGTCA | ACTCCAACTA | CATTCTCAGT | GGTATCTCTG | GACCAGACT | CTCCATAACC | 960
| TTTCCCAACA | TTGGTGGACT | TCCAGGCTCC | ACTACAACCC | ATAGCCTTAA | CTCTGCCAGA | 1020
| GTGAACTACA | GTGGAGGTGT | CAGCTCTGGA | TTGATTGGTG | CAACTAACTT | GAACCACAAC | 1080
| TTCAATTGCT | CCACCGTCTT | GCCACCTCTG | AGCACACCGT | TTGTGAGGTC | CTGGCTTGAC | 1140
| AGCGGTACTG | ATCGCGAAGG | AGTTGCTACC | TCTACAAACT | GGCAAACCGA | GTCCTTCCAA | 1200
| ACCACTCTTA | GCCTTCGGTG | TGGAGCTTTC | TCTGCACGTG | GGAATTCAAA | CTACTTTCCA | 1260
| GACTACTTCA | TTAGGAACAT | CTCTGGTGTT | CCTCTCGTCA | TCAGGAATGA | AGACCTCACC | 1320
| CGTCCACTTC | ATTACAACCA | GATTAGGAAC | ATCGAGTCTC | CATCCGGTAC | TCCAGGAGGT | 1380
| GCAAGAGCTT | ACCTCGTGTC | TGTCCATAAC | AGGAAGAACA | ACATCTACGC | TGCCAACGAG | 1440
| AATGGCACCA | TGATTCACCT | TGCACCAGAA | GATTACACTG | GATTCACCAT | CTCTCCAATC | 1500
| CATGCTACCC | AAGTGAACAA | TCAGACACGC | ACCTTCATCT | CCGAAAAGTT | CGGAAATCAA | 1560

| | | | | | | |
|---|---|---|---|---|---|---|
| GGTGACTCCT | TGAGGTTCGA | GCAATCCAAC | ACTACCGCTA | GGTACACTTT | GAGAGGCAAT | 1620 |
| GGAAACAGCT | ACAACCTTTA | CTTGAGAGTT | AGCTCCATTG | GTAACTCCAC | CATCCGTGTT | 1680 |
| ACCATCAACG | GACGTGTTTA | CACAGTCTCT | AATGTGAACA | CTACAACGAA | CAATGATGGC | 1740 |
| GTTAACGACA | ACGGAGCCAG | ATTCAGCGAC | ATCAACATTG | GCAACATCGT | GGCCTCTGAC | 1800 |
| AACACTAACG | TTACTTTGGA | CATCAATGTG | ACCCTCAATT | CTGGAACTCC | ATTTGATCTC | 1860 |
| ATGAACATCA | TGTTTGTGCC | AACTAACCTC | CCTCCATTGT | ACTAATGAGA | TCTAAGCTT | 1919 |

( 2 ) INFORMATION FOR SEQ ID NO:107:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:107:

| | | | | | |
|---|---|---|---|---|---|
| TCTAGAAGAT | CTCCACCATG | GACAACTCCG | TCCTGAACTC | TGGTCGCACC | ACCATCT | 57 |

( 2 ) INFORMATION FOR SEQ ID NO:108:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:108:

| | | | | | |
|---|---|---|---|---|---|
| GCGACGCCTA | CAACGTCGCG | GCGCATGATC | CATTCAGCTT | CCAGCACAAG | AGCCTCGACA | 60 |
| CTGTTCAGAA | | | | | | 70 |

( 2 ) INFORMATION FOR SEQ ID NO:109:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:109:

| | | | | | |
|---|---|---|---|---|---|
| GGAGTGGACG | GAGTGGAAGA | AGAACAACCA | CAGCCTGTAC | CTGGACCCCA | TCGTCGGCAC | 60 |
| GGTGGCCAGC | TTCCT | | | | | 75 |

( 2 ) INFORMATION FOR SEQ ID NO:110:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:110:

| | | | | | |
|---|---|---|---|---|---|
| TCTCAAGAAG | GTCGGCTCTC | TCGTCGGGAA | GCGCATCCTC | TCGGAACTCC | GCAACCTGAT | 60 |
| CAGGATCC | | | | | | 68 |

( 2 ) INFORMATION FOR SEQ ID NO:111:

(  i  ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear (  i i  ) MOLECULE TYPE: DNA (synthetic)

(  x i  ) SEQUENCE DESCRIPTION: SEQ ID NO:111:

CCATCTAGAA GATCTCCACC                   20

( 2 ) INFORMATION FOR SEQ ID NO:112:

(  i  ) SEQUENCE CHARACTERISTICS:
   ( A ) LENGTH: 20 base pairs
   ( B ) TYPE: nucleic acid
   ( C ) STRANDEDNESS: single
   ( D ) TOPOLOGY: linear (  i i  ) MOLECULE TYPE: DNA (synthetic)

(  x i  ) SEQUENCE DESCRIPTION: SEQ ID NO:112:

TGGGGATCCT GATCAGGTTG                   20

( 2 ) INFORMATION FOR SEQ ID NO:113:

(  i  ) SEQUENCE CHARACTERISTICS:
   ( A ) LENGTH: 81 base pairs
   ( B ) TYPE: nucleic acid
   ( C ) STRANDEDNESS: single
   ( D ) TOPOLOGY: linear (  i i  ) MOLECULE TYPE: DNA (synthetic)

(  x i  ) SEQUENCE DESCRIPTION: SEQ ID NO:113:

AGATCTTTCC ATCTGGCTCC ACCAACCTCA TGCAAGACAT CCTCAGGGAG ACCGAGAAGT    60

TTCTCAACCA GCGCCTCAAC A                  81

( 2 ) INFORMATION FOR SEQ ID NO:114:

(  i  ) SEQUENCE CHARACTERISTICS:
   ( A ) LENGTH: 75 base pairs
   ( B ) TYPE: nucleic acid
   ( C ) STRANDEDNESS: single
   ( D ) TOPOLOGY: linear (  i i  ) MOLECULE TYPE: DNA (synthetic)

(  x i  ) SEQUENCE DESCRIPTION: SEQ ID NO:114:

CTGATACCCT TGCTCGCGTC AACGCTGAGC TGACGGGTCT GCAAGCAAAC GTGGAGGAGT    60

TCAACCGCCA AGTGG                     75

( 2 ) INFORMATION FOR SEQ ID NO:115:

(  i  ) SEQUENCE CHARACTERISTICS:
   ( A ) LENGTH: 45 base pairs
   ( B ) TYPE: nucleic acid
   ( C ) STRANDEDNESS: single
   ( D ) TOPOLOGY: linear (  i i  ) MOLECULE TYPE: DNA (synthetic)

(  x i  ) SEQUENCE DESCRIPTION: SEQ ID NO:115:

ACAACTTCCT CAACCCCAAC CGCAATGCGG TGCCTCTGTC CATCA          45

( 2 ) INFORMATION FOR SEQ ID NO:116:

( i ) SEQUENCE CHARACTERISTICS:
    ( A ) LENGTH: 65 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:116:

CTTCTTCCGT GAACACCATG CAACAACTGT TCCTCAACCG CTTGCCTCAG TTCCAGATGC    60

AAGGC    65

( 2 ) INFORMATION FOR SEQ ID NO:117:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:117:

TACCAGCTGC TCCTGCTGCC ACTCTTTGCT CAGGCTGCCA ACCTGCACCT CTCCTTCATT    60

CGTGACGTG    69

( 2 ) INFORMATION FOR SEQ ID NO:118:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:118:

ATCCTCAACG CTGACGAGTG GGGCATCTCT GCAG    34

( 2 ) INFORMATION FOR SEQ ID NO:119:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:119:

CCAAGATCTT TCCATCTGGC    20

( 2 ) INFORMATION FOR SEQ ID NO:120:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:120:

GGTCTGCAGA GATGCCCCAC    20

( 2 ) INFORMATION FOR SEQ ID NO:121:

( i ) SEQUENCE CHARACTERISTICS:

( A ) LENGTH: 67 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:121:

```
CTGCAGCCAC GCTGAGGACC TACCGCGACT ACCTGAAGAA CTACACCAGG GACTACTCCA        60
ACTATTG                                                                  67
```

( 2 ) INFORMATION FOR SEQ ID NO:122:

( i ) SEQUENCE CHARACTERISTICS:
( A ) LENGTH: 69 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:122:

```
CATCAACACC TACCAGTCGG CCTTCAAGGG CCTCAATACG AGGCTTCACG ACATGCTGGA        60
GTTCAGGAC                                                                69
```

( 2 ) INFORMATION FOR SEQ ID NO:123:

( i ) SEQUENCE CHARACTERISTICS:
( A ) LENGTH: 52 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:123:

```
CTACATGTTC CTGAACGTGT TCGAGTACGT CAGCATCTGG TCGCTCTTCA AG                52
```

( 2 ) INFORMATION FOR SEQ ID NO:124:

( i ) SEQUENCE CHARACTERISTICS:
( A ) LENGTH: 68 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:124:

```
TACCAGAGCC TGCTGGTGTC CAGCGGCGCC AACCTCTACG CCAGCGGCTC TGGTCCCCAA        60
CAAACTCA                                                                 68
```

( 2 ) INFORMATION FOR SEQ ID NO:125:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:125:

```
GAGCTTCACC AGCCAGGACT GGCCATTCCT GTATTCGTTG TTCCAAGTCA A                 51
```

( 2 ) INFORMATION FOR SEQ ID NO:126:

( i ) SEQUENCE CHARACTERISTICS:
 ( A ) LENGTH: 57 base pairs
 ( B ) TYPE: nucleic acid
 ( C ) STRANDEDNESS: single
 ( D ) TOPOLOGY: linear ( i i ) MOLECULE TYPE: DNA (synthetic)

( x i ) SEQUENCE DESCRIPTION: SEQ ID NO:126:

CTCCAACTAC GTCCTCAACG GCTTCTCTGG TGCTCGCCTC TCCAACACCT TCCCCAA 57

( 2 ) INFORMATION FOR SEQ ID NO:127:

( i ) SEQUENCE CHARACTERISTICS:
 ( A ) LENGTH: 78 base pairs
 ( B ) TYPE: nucleic acid
 ( C ) STRANDEDNESS: single
 ( D ) TOPOLOGY: linear ( i i ) MOLECULE TYPE: DNA (synthetic)

( x i ) SEQUENCE DESCRIPTION: SEQ ID NO:127:

CATTGTTGGC CTCCCCGGCT CCACCACAAC TCATGCTCTG CTTGCTGCCA GAGTGAACTA 60

CTCCGGCGGC ATCTCGAG 78

( 2 ) INFORMATION FOR SEQ ID NO:128:

( i ) SEQUENCE CHARACTERISTICS:
 ( A ) LENGTH: 23 base pairs
 ( B ) TYPE: nucleic acid
 ( C ) STRANDEDNESS: single
 ( D ) TOPOLOGY: linear ( i i ) MOLECULE TYPE: DNA (synthetic)

( x i ) SEQUENCE DESCRIPTION: SEQ ID NO:128:

CCACTGCAGC CACGCTGAGG ACC 23

( 2 ) INFORMATION FOR SEQ ID NO:129:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: DNA (synthetic)

( x i ) SEQUENCE DESCRIPTION: SEQ ID NO:129:

GGTCTCGAGA TGCCGCCGGA 20

( 2 ) INFORMATION FOR SEQ ID NO:130:

( i ) SEQUENCE CHARACTERISTICS:
 ( A ) LENGTH: 76 base pairs
 ( B ) TYPE: nucleic acid
 ( C ) STRANDEDNESS: single
 ( D ) TOPOLOGY: linear ( i i ) MOLECULE TYPE: DNA (synthetic)

( x i ) SEQUENCE DESCRIPTION: SEQ ID NO:130:

ATTGGTGCAT CGCCGTTCAA CCAGAACTTC AACTGCTCCA CCTTCCTGCC GCCGCTGCTC 60

ACCCCGTTCG TGAGGT 76

( 2 ) INFORMATION FOR SEQ ID NO:131:

( i ) SEQUENCE CHARACTERISTICS:

(A) LENGTH: 59 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:131:

CCTGGCTCGA CAGCGGCTCC GACCGCGAGG GCGTGGCCAC CGTCACCAAC TGGCAAACC    59

(2) INFORMATION FOR SEQ ID NO:132:

(i) SEQUENCE CHARACTERISTICS:
(A) LENGTH: 54 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:132:

GAGTCCTTCG AGACCACCCT TGGCCTCCGG AGCGGCGCCT TCACGGCGCG TGGG    54

(2) INFORMATION FOR SEQ ID NO:133:

(i) SEQUENCE CHARACTERISTICS:
(A) LENGTH: 44 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:133:

AATTCTAACT ACTTCCCGA CTACTTCATC AGGAACATCT CTGG    44

(2) INFORMATION FOR SEQ ID NO:134:

(i) SEQUENCE CHARACTERISTICS:
(A) LENGTH: 63 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:134:

TGTTCCTCTC GTCGTCCGCA ACGAGGACCT CCGCCGTCCA CTGCACTACA ACGAGATCAG    60
GAA    63

(2) INFORMATION FOR SEQ ID NO:135:

(i) SEQUENCE CHARACTERISTICS:
(A) LENGTH: 61 base pairs
(B) TYPE: nucleic acid
(C) STRANDEDNESS: single
(D) TOPOLOGY: linear (i i) MOLECULE TYPE: DNA (synthetic)

(x i) SEQUENCE DESCRIPTION: SEQ ID NO:135:

CATCGCCTCT CCGTCCGGGA CGCCCGGAGG TGCAAGGGCG TACATGGTGA GCGTCCATAA    60
C    61

(2) INFORMATION FOR SEQ ID NO:136:

(i) SEQUENCE CHARACTERISTICS:
(A) LENGTH: 44 base pairs ( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:136:

AGGAAGAACA ACATCCACGC TGTGCATGAG AACGGCTCCA TGAT    44

( 2 ) INFORMATION FOR SEQ ID NO:137:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:137:

CCACTCGAGC GGCGACATTG GTGCATCGCC G    31

( 2 ) INFORMATION FOR SEQ ID NO:138:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:138:

GGTGGTACCT GATCATGGAG CCGTTCTCAT GCA    33

( 2 ) INFORMATION FOR SEQ ID NO:139:

( i ) SEQUENCE CHARACTERISTICS:
( A ) LENGTH: 64 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:139:

GGATCCACCT GGCGCCCAAT GATTACACCG GCTTCACCAT CTCTCCAATC CACGCCACCC    60
AAGT    64

( 2 ) INFORMATION FOR SEQ ID NO:140:

( i ) SEQUENCE CHARACTERISTICS:
( A ) LENGTH: 62 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:140:

GAACAACCAG ACACGCACCT TCATCTCCGA GAAGTTCGGC AACCAGGGCG ACTCCCTGAG    60
GT    62

( 2 ) INFORMATION FOR SEQ ID NO:141:

( i ) SEQUENCE CHARACTERISTICS:
( A ) LENGTH: 81 base pairs
( B ) TYPE: nucleic acid ( C ) STRANDEDNESS: single
( D ) TOPOLOGY: linear ( i i ) MOLECULE TYPE: DNA (synthetic)

( x i ) SEQUENCE DESCRIPTION: SEQ ID NO:141:

TCGAGCAGAA CAACACCACC GCCAGGTACA CCCTGCGCGG CAACGGCAAC AGCTACAACC    60

TGTACCTGCG CGTCAGCTCC A    81

( 2 ) INFORMATION FOR SEQ ID NO:142:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:142:

TTGGCAACTC CACCATCAGG GTCACCATCA ACGGGAGGGT GTACACAGCC ACCAATGTGA    60

ACACGACGAC CAACAATG    78

( 2 ) INFORMATION FOR SEQ ID NO:143:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:143:

ATGGCGTCAA CGACAACGGC GCCCGCTTCA GCGACATCAA C    41

( 2 ) INFORMATION FOR SEQ ID NO:144:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:144:

ATTGGCAACG TGGTGGCCAG CAGCAACTCC GACGTCCCGC TGGACAT    47

( 2 ) INFORMATION FOR SEQ ID NO:145:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:145:

CAACGTGACC CTGAACTCTG GCACCCAGTT CGACCTCATG AA    42

( 2 ) INFORMATION FOR SEQ ID NO:146:

( i ) SEQUENCE CHARACTERISTICS:
        ( A ) LENGTH: 61 base pairs
        ( B ) TYPE: nucleic acid
        ( C ) STRANDEDNESS: single ( D ) TOPOLOGY: linear ( i i ) MOLECULE TYPE: DNA (synthetic)

( x i ) SEQUENCE DESCRIPTION: SEQ ID NO:146:

CATCATGCTG GTGCCAACTA ACATCTCGCC GCTGTACTGA TAGGAGCTCT GATCAGGTAC  60

C  61

( 2 ) INFORMATION FOR SEQ ID NO:147:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:147:

GGAGGATCCA CCTGGCGCCC A  21

( 2 ) INFORMATION FOR SEQ ID NO:148:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:148:

GGTGGTACCT GATCAGAGCT  20

( 2 ) INFORMATION FOR SEQ ID NO:149:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:149:

CCACCATGGA CAACTCCGTC  20

( 2 ) INFORMATION FOR SEQ ID NO:150:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:150:

GGAAGAAGAA CAACCACAGC CTGTACCTGG ACCC  34

( 2 ) INFORMATION FOR SEQ ID NO:151:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:151:

CCACCAACCT CATGCAAGAC                                                    20

( 2 ) INFORMATION FOR SEQ ID NO:152:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:152:

CTCAACCAGC GCCTCAACAC                                                    20

( 2 ) INFORMATION FOR SEQ ID NO:153:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:153:

CCGCAATGCG GTGCCTCTGT CCATCACTTC TTCCGTG                                 37

( 2 ) INFORMATION FOR SEQ ID NO:154:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:154:

CGTGACGTGA TCCTCAACG                                                     19

( 2 ) INFORMATION FOR SEQ ID NO:155:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:155:

GGACTGGCCA TTCCTGTAT                                                     19

( 2 ) INFORMATION FOR SEQ ID NO:156:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:156:

CGCCAGCGGC TCTGGTCCC                                                     19

( 2 ) INFORMATION FOR SEQ ID NO:157:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:157:

GAAGAACTAC ACCAGGGAC                                                                                   19

( 2 ) INFORMATION FOR SEQ ID NO:158:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:158:

GCTCCGACCG CGAGGGCGTG                                                             20

( 2 ) INFORMATION FOR SEQ ID NO:159:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:159:

CTCCGGAGCG GCGCCTTCAC GGCGCGTGGG AATTC                             35

( 2 ) INFORMATION FOR SEQ ID NO:160:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:160:

CATCTCTGGT GTTCCTCTCG                                                             20

( 2 ) INFORMATION FOR SEQ ID NO:161:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:161:

GCGGCAACGG CAACAGCTAC                                                             20

( 2 ) INFORMATION FOR SEQ ID NO:162:

( i ) SEQUENCE CHARACTERISTICS:
        ( A ) LENGTH: 22 base pairs 103 104
-continued ( B ) TYPE: nucleic acid
   ( C ) STRANDEDNESS: single
   ( D ) TOPOLOGY: linear ( i i ) MOLECULE TYPE: DNA (synthetic)

( x i ) SEQUENCE DESCRIPTION: SEQ ID NO:162:

CTCCACCATC AGGGTCACCA TC    22

( 2 ) INFORMATION FOR SEQ ID NO:163:

( i ) SEQUENCE CHARACTERISTICS:
       ( A ) LENGTH: 18 base pairs
       ( B ) TYPE: nucleic acid
       ( C ) STRANDEDNESS: single
       ( D ) TOPOLOGY: linear ( i i ) MOLECULE TYPE: DNA (synthetic)

( x i ) SEQUENCE DESCRIPTION: SEQ ID NO:163:

GAACATCATG CTGGTGCC    18

( 2 ) INFORMATION FOR SEQ ID NO:164:

( i ) SEQUENCE CHARACTERISTICS:
       ( A ) LENGTH: 3471 base pairs
       ( B ) TYPE: nucleic acid
       ( C ) STRANDEDNESS: double
       ( D ) TOPOLOGY: linear ( i i ) MOLECULE TYPE: DNA (genomic)

( x i ) SEQUENCE DESCRIPTION: SEQ ID NO:164:

ATGGATAACA ATCCGAACAT CAATGAATGC ATTCCTTATA ATTGTTTAAG TAACCCTGAA    60
GTAGAAGTAT TAGGTGGAGA AAGAATAGAA ACTGGTTACA CCCCAATCGA TATTTCCTTG    120
TCGCTAACGC AATTTCTTTT GAGTGAATTT GTTCCGGTG CTGGATTTGT GTTAGGACTA    180
GTTGATATAA TATGGGGAAT TTTTGGTCCC TCTCAATGGG ACGCATTTCT TGTACAAATT    240
GAACAGTTAA TTAACCAAAG AATAGAAGAA TTCGCTAGGA ACCAAGCCAT TTCTAGATTA    300
GAAGGACTAA GCAATCTTTA TCAAATTTAC GCAGAATCTT TTAGAGAGTG GAAGCAGAT    360
CCTACTAATC CAGCATTAAG AGAAGAGATG CGTATTCAAT TCAATGACAT GAACAGTGCC    420
CTTACAACCG CTATTCCTCT TTTTGCAGTT CAAAATTATC AAGTTCCTCT TTTATCAGTA    480
TATGTTCAAG CTGCAAATTT ACATTTATCA GTTTTGAGAG ATGTTCAGT GTTTGGACAA    540
AGGTGGGGAT TGATGCCGC GACTATCAAT AGTCGTTATA ATGATTTAAC TAGGCTTATT    600
GGCAACTATA CAGATCATGC TGTACGCTGG TACAATACGG GATTAGAGCG TGTATGGGGA    660
CCGGATTCTA GAGATTGGAT AAGATATAAT CAATTTAGAA GAGAATTAAC ACTAACTGTA    720
TTAGATATCG TTTCTCTATT TCCGAACTAT GATAGTAGAA CGTATCCAAT CGAACAGTT    780
TCCCAATTAA CAAGAGAAAT TTATACAAAC CCAGTATTAG AAAATTTGA TGGTAGTTTT    840
CGAGGCTCGG CTCAGGGCAT AGAAGGAAGT ATTAGGAGTC CACATTGAT GGATATACTT    900
AATAGTATAA CCATCTATAC GGATGCTCAT AGAGGAGAAT ATTATTGGTC AGGGCATCAA    960
ATAATGGCTT CTCCTGTAGG GTTTTCGGGG CCAGAATTCA CTTTTCCGCT ATATGGAACT    1020
ATGGGAAATG CAGCTCCACA ACAACGTATT GTTGCTCAAC TAGGTCAGGG CGTGTATAGA    1080
ACATTATCGT CCACCTTATA TAGAAGACCT TTTAATATAG GATAAATAA TCAACAACTA    1140
TCTGTTCTTG ACGGGACAGA ATTTGCTTAT GGAACCTCCT CAAATTTGCC ATCCGCTGTA    1200
TACAGAAAAA GCGGAACGGT AGATTCGCTG GATGAAATAC CGCCACAGAA TAACAACGTG    1260

-continued

| | | | | | |
|---|---|---|---|---|---|
| CCACCTAGGC | AAGGATTTAG | TCATCGATTA | AGCCATGTTT | CAATGTTTCG | TTCAGGCTTT | 1320 |
| AGTAATAGTA | GTGTAAGTAT | AATAAGAGCT | CCTATGTTCT | CTTGGATACA | TCGTAGTGCT | 1380 |
| GAATTTAATA | ATATAATTCC | TTCATCACAA | ATTACACAAA | TACCTTTAAC | AAAATCTACT | 1440 |
| AATCTTGGCT | CTGGAACTTC | TGTCGTTAAA | GGACCAGGAT | TTACAGGAGG | AGATATTCTT | 1500 |
| CGAAGAACTT | CACCTGGCCA | GATTTCAACC | TTAAGAGTAA | ATATTACTGC | ACCATTATCA | 1560 |
| CAAAGATATC | GGGTAAGAAT | TCGCTACGCT | TCTACCACAA | ATTACAATT | CCATACATCA | 1620 |
| ATTGACGGAA | GACCTATTAA | TCAGGGGAAT | TTTTCAGCAA | CTATGAGTAG | TGGGAGTAAT | 1680 |
| TTACAGTCCG | GAAGCTTTAG | GACTGTAGGT | TTTACTACTC | CGTTAACTT | TTCAAATGGA | 1740 |
| TCAAGTGTAT | TTACGTTAAG | TGCTCATGTC | TTCAATTCAG | GCAATGAAGT | TTATATAGAT | 1800 |
| CGAATTGAAT | TTGTTCCGGC | AGAAGTAACC | TTTGAGGCAG | AATATGATTT | AGAAAGAGCA | 1860 |
| CAAAAGGCGG | TGAATGAGCT | GTTTACTTCT | TCCAATCAAA | TCGGGTTAAA | AACAGATGTG | 1920 |
| ACGGATTATC | ATATTGATCA | AGTATCCAAT | TTAGTTGAGT | GTTTATCTGA | TGAATTTTGT | 1980 |
| CTGGATGAAA | AAAAAGAATT | GTCCGAGAAA | GTCAAACATG | CGAAGCGACT | TAGTGATGAG | 2040 |
| CGGAATTTAC | TTCAAGATCC | AAACTTTAGA | GGGATCAATA | GACAACTAGA | CCGTGGCTGG | 2100 |
| AGAGGAAGTA | CGGATATTAC | CATCCAAGGA | GGCGATGACG | TATTCAAAGA | GAATTACGTT | 2160 |
| ACGCTATTGG | GTACCTTTGA | TGAGTGCTAT | CCAACGTATT | TATATCAAAA | AATAGATGAG | 2220 |
| TCGAAATTAA | AAGCCTATAC | CCGTTACCAA | TTAAGAGGGT | ATATCGAAGA | TAGTCAAGAC | 2280 |
| TTAGAAATCT | ATTTAATTCG | CTACAATGCC | AAACACGAAA | CAGTAAATGT | GCCAGGTACG | 2340 |
| GGTTCCTTAT | GGCCGCTTTC | AGCCCCAAGT | CCAATCGGAA | AATGTGCCCA | TCATTCCCAT | 2400 |
| CATTTCTCCT | TGGACATTGA | TGTTGGATGT | ACAGACTTAA | ATGAGGACTT | AGGTGTATGG | 2460 |
| GTGATATTCA | AGATTAAGAC | GCAAGATGGC | CATGAAAGAC | TAGGAAATCT | AGAATTTCTC | 2520 |
| GAAGGAAGAG | CACCATTAGT | AGGAGAAGCA | CTAGCTCGTG | TGAAAAGAGC | GGAGAAAAAA | 2580 |
| TGGAGAGACA | AACGTGAAAA | ATTGGAATGG | GAAACAAATA | TTGTTTATAA | AGAGGCAAAA | 2640 |
| GAATCTGTAG | ATGCTTTATT | TGTAAACTCT | CAATATGATA | GATTACAAGC | GGATACCAAC | 2700 |
| ATCGCGATGA | TTCATGCGGC | AGATAAACGC | GTTCATAGCA | TTCGAGAAGC | TTATCTGCCT | 2760 |
| GAGCTGTCTG | TGATTCCGGG | TGTCAATGCG | GCTATTTTTG | AAGAATTAGA | AGGGCGTATT | 2820 |
| TTCACTGCAT | TCTCCCTATA | TGATGCGAGA | AATGTCATTA | AAAATGGTGA | TTTTAATAAT | 2880 |
| GGCTTATCCT | GCTGGAACGT | GAAAGGGCAT | GTAGATGTAG | AAGAACAAAA | CAACCACCGT | 2940 |
| TCGGTCCTTG | TTGTTCCGGA | ATGGGAAGCA | GAAGTGTCAC | AAGAAGTTCG | TGTCTGTCCG | 3000 |
| GGTCGTGGCT | ATATCCTTCG | TGTCACAGCG | TACAAGGAGG | GATATGGAGA | AGGTTGCGTA | 3060 |
| ACCATTCATG | AGATCGAGAA | CAATACAGAC | GAACTGAAGT | TTAGCAACTG | TGTAGAAGAG | 3120 |
| GAAGTATATC | CAAACAACAC | GGTAACGTGT | AATGATTATA | CTGCGACTCA | AGAAGAATAT | 3180 |
| GAGGGTACGT | ACACTTCTCG | TAATCGAGGA | TATGACGGAG | CCTATGAAAG | CAATTCTTCT | 3240 |
| GTACCAGCTG | ATTATGCATC | AGCCTATGAA | GAAAAGCAT | ATACAGATGG | ACGAAGAGAC | 3300 |
| AATCCTTGTG | AATCTAACAG | AGGATATGGG | GATTACACAC | CACTACCAGC | TGGCTATGTG | 3360 |
| ACAAAAGAAT | TAGAGTACTT | CCCAGAAACC | GATAAGGTAT | GGATTGAGAT | CGGAGAAACG | 3420 |
| GAAGGAACAT | TCATCGTGGA | CAGCGTGGAA | TTACTTCTTA | TGGAGGAATA | A | 3471 |